US010982274B2

(12) United States Patent
Berka et al.

(10) Patent No.: US 10,982,274 B2
(45) Date of Patent: *Apr. 20, 2021

(54) BEAD EMULSION NUCLEIC ACID AMPLIFICATION

(71) Applicant: Roche Molecular Systems, Inc., Pleasanton, CA (US)

(72) Inventors: Jan Berka, New Haven, CT (US); Yi-Ju Chen, New Haven, CT (US); John H. Leamon, Guilford, CT (US); Steven Lefkowitz, Branford, CT (US); Kenton L. Lohman, Guilford, CT (US); Vinod B. Makhijani, Guilford, CT (US); Jonathan M. Rothberg, Guilford, CT (US); Gary J. Sarkis, Guilford, CT (US); Maithreyan Srinivasan, Branford, CT (US); Michael P. Weiner, Guilford, CT (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 16/249,681

(22) Filed: Jan. 16, 2019

(65) Prior Publication Data
US 2019/0203263 A1    Jul. 4, 2019

Related U.S. Application Data

(63) Continuation of application No. 15/190,886, filed on Jun. 23, 2016, now Pat. No. 10,240,192, which is a continuation of application No. 14/518,700, filed on Oct. 20, 2014, now abandoned, which is a continuation of application No. 14/036,398, filed on Sep. 25, 2013, now abandoned, which is a continuation of application No. 13/618,334, filed on Sep. 14, 2012, now Pat. No. 8,765,380, which is a continuation of application No. 13/033,240, filed on Feb. 23, 2011, now Pat. No. 8,748,102, which is a continuation of application No. 11/982,095, filed on Oct. 31, 2007, now Pat. No. 8,012,690, which is a continuation of application No. 10/767,899, filed on Jan. 28, 2004, now Pat. No. 7,842,457.

(Continued)

(51) Int. Cl.
C12Q 1/68        (2018.01)
B01L 3/00        (2006.01)
C07H 21/00       (2006.01)
C12N 15/10       (2006.01)
G01N 21/25       (2006.01)
G01N 21/64       (2006.01)
G01R 33/12       (2006.01)
C12Q 1/686       (2018.01)
C12Q 1/6834      (2018.01)
C12Q 1/6844      (2018.01)
C12Q 1/6865      (2018.01)
C12Q 1/6867      (2018.01)
C12Q 1/6869      (2018.01)
C12Q 1/6874      (2018.01)
C12Q 1/6806      (2018.01)
B01L 7/00        (2006.01)

(52) U.S. Cl.
CPC ........ *C12Q 1/686* (2013.01); *B01L 3/502707* (2013.01); *B01L 3/502715* (2013.01); *C07H 21/00* (2013.01); *C12N 15/1075* (2013.01); *C12N 15/1093* (2013.01); *C12Q 1/6806* (2013.01); *C12Q 1/6834* (2013.01); *C12Q 1/6844* (2013.01); *C12Q 1/6865* (2013.01); *C12Q 1/6867* (2013.01); *C12Q 1/6869* (2013.01); *C12Q 1/6874* (2013.01); *G01N 21/253* (2013.01); *G01N 21/6428* (2013.01); *G01N 21/6452* (2013.01); *G01R 33/1269* (2013.01); *B01L 3/5027* (2013.01); *B01L 3/5085* (2013.01); *B01L 7/52* (2013.01); *B01L 2300/0636* (2013.01); *B01L 2300/0819* (2013.01); *B01L 2300/0877* (2013.01); *G01N 21/6458* (2013.01); *G01N 2021/6484* (2013.01); *Y02P 20/582* (2015.11); *Y10T 436/143333* (2015.01)

(58) Field of Classification Search
CPC ................ C12Q 1/6806; C12Q 1/6834; C12Q 2563/149; C12Q 2563/159
See application file for complete search history.

(56) References Cited

U.S. PATENT DOCUMENTS 4,175,054 A    11/1979    Tait et al.
4,801,529 A    1/1989     Perlman
(Continued)

FOREIGN PATENT DOCUMENTS

DE    19646372 C1    6/1997
EP    0392546 A2    10/1990
(Continued)

OTHER PUBLICATIONS

U.S. Appl. No. 60/443,471, filed Jan. 29, 2003, Weiner et al.
(Continued)

Primary Examiner — David C Thomas
(74) Attorney, Agent, or Firm — Cooley LLP; Ivor R. Elrifi; Matthew Pavao

(57) ABSTRACT

Disclosed are methods for nucleic acid amplification wherein nucleic acid templates, beads, and amplification reaction solution are emulsified and the nucleic acid templates are amplified to provide clonal copies of the nucleic acid templates attached to the beads. Also disclosed are kits and apparatuses for performing the methods of the invention.

9 Claims, 9 Drawing Sheets

Specification includes a Sequence Listing.

Related U.S. Application Data

(60) Provisional application No. 60/497,985, filed on Aug. 25, 2003, provisional application No. 60/476,592, filed on Jun. 6, 2003, provisional application No. 60/476,602, filed on Jun. 6, 2003, provisional application No. 60/476,504, filed on Jun. 6, 2003, provisional application No. 60/476,313, filed on Jun. 6, 2003, provisional application No. 60/465,071, filed on Apr. 23, 2003, provisional application No. 60/443,471, filed on Jan. 29, 2003.

(56) References Cited

U.S. PATENT DOCUMENTS

| | | |
|---|---|---|
| 4,938,876 A | 7/1990 | Ohsol |
| 5,225,332 A | 7/1993 | Weaver et al. |
| 5,405,746 A | 4/1995 | Uhlen |
| 5,503,851 A | 4/1996 | Mank et al. |
| 5,616,478 A | 4/1997 | Chetverin et al. |
| 5,674,743 A | 10/1997 | Ulmer |
| 5,714,320 A | 2/1998 | Kool |
| 5,891,477 A | 4/1999 | Lanza et al. |
| 5,989,892 A | 11/1999 | Nishimaki et al. |
| 6,023,540 A | 2/2000 | Walt et al. |
| 6,124,092 A | 9/2000 | O'Neill et al. |
| 6,143,496 A | 11/2000 | Brown et al. |
| 6,184,012 B1 | 2/2001 | Neri et al. |
| 6,210,891 B1 | 4/2001 | Nyren et al. |
| 6,258,568 B1 | 7/2001 | Nyren |
| 6,258,858 B1 | 7/2001 | Nakajima et al. |
| 6,266,459 B1 | 7/2001 | Walt et al. |
| 6,274,320 B1 | 8/2001 | Rothberg et al. |
| 6,274,351 B1 | 8/2001 | Peponnet |
| 6,303,309 B1 | 10/2001 | Jurinke et al. |
| 6,310,354 B1 | 10/2001 | Hanninen et al. |
| 6,340,589 B1 | 1/2002 | Turner et al. |
| 6,378,527 B1 | 4/2002 | Hungerford et al. |
| 6,475,722 B1 | 11/2002 | Henck |
| 6,489,103 B1 | 12/2002 | Griffiths et al. |
| 6,902,921 B2 | 6/2005 | Srinivasan et al. |
| 6,956,114 B2 | 10/2005 | Srinivasan et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,323,305 B2 | 1/2008 | Leamon et al. |
| 7,335,762 B2 | 2/2008 | Rothberg et al. |
| 7,585,865 B2 | 8/2009 | Leamon et al. |
| 7,601,499 B2 | 10/2009 | Berka et al. |
| 7,682,816 B2 | 3/2010 | Kim et al. |
| 7,785,862 B2 | 8/2010 | Kim et al. |
| 7,842,457 B2 | 11/2010 | Berka et al. |
| 7,927,797 B2 | 4/2011 | Nobile et al. |
| 8,012,690 B2 | 9/2011 | Berka et al. |
| 8,158,359 B2 | 4/2012 | Leamon et al. |
| 8,301,394 B2 | 10/2012 | Chen et al. |
| 8,364,417 B2 | 1/2013 | Chen et al. |
| 8,617,816 B2 | 12/2013 | Simen et al. |
| 8,748,102 B2 | 6/2014 | Berka et al. |
| 8,765,380 B2 | 7/2014 | Berka et al. |
| 8,790,876 B2 | 7/2014 | Leamon et al. |
| 9,317,654 B2 | 4/2016 | Chen et al. |
| 10,240,192 B2 | 3/2019 | Berka et al. |
| 2001/0020011 A1 | 9/2001 | Mathiowitz et al. |
| 2001/0036632 A1 | 11/2001 | Yu et al. |
| 2002/0001675 A1 | 1/2002 | Tisone |
| 2002/0022038 A1 | 2/2002 | Biatry et al. |
| 2002/0119459 A1 | 8/2002 | Griffiths |
| 2002/0155080 A1 | 10/2002 | Glenn et al. |
| 2002/0168279 A1 | 11/2002 | Yamamoto et al. |
| 2002/0172965 A1 | 11/2002 | Kamb et al. |
| 2002/0172980 A1 | 11/2002 | Phan et al. |
| 2003/0108900 A1 | 6/2003 | Oliphant et al. |
| 2003/0124586 A1 | 7/2003 | Griffiths et al. |
| 2004/0005594 A1 | 1/2004 | Holliger et al. |
| 2004/0053254 A1 | 3/2004 | Wangh et al. |
| 2004/0185484 A1 | 9/2004 | Costa et al. |
| 2004/0253731 A1 | 12/2004 | Holliger et al. |
| 2005/0037392 A1 | 2/2005 | Griffiths et al. |
| 2005/0042648 A1 | 2/2005 | Griffiths et al. |
| 2005/0064460 A1 | 3/2005 | Holliger et al. |
| 2005/0069920 A1 | 3/2005 | Griffiths et al. |
| 2005/0079510 A1 | 4/2005 | Berka et al. |
| 2005/0164239 A1 | 7/2005 | Griffiths et al. |
| 2008/0132693 A1 | 6/2008 | Berka et al. |
| 2011/0177587 A1 | 7/2011 | Nobile et al. |
| 2014/0162885 A1 | 6/2014 | Berka et al. |
| 2015/0099672 A1 | 4/2015 | Berka et al. |

FOREIGN PATENT DOCUMENTS

| | | |
|---|---|---|
| EP | 0329822 B1 | 6/1994 |
| EP | 0579347 B1 | 4/1996 |
| EP | 1522582 A2 | 4/2005 |
| EP | 1590477 B1 | 11/2005 |
| EP | 1522582 B1 | 7/2007 |
| EP | 1482036 B1 | 10/2007 |
| EP | 1594980 B1 | 11/2009 |
| EP | 1522581 B1 | 3/2012 |
| JP | 2000316561 A | 11/2000 |
| WO | WO-8810315 A1 | 12/1988 |
| WO | WO-8906700 A1 | 7/1989 |
| WO | WO-8910566 A1 | 11/1989 |
| WO | WO-9105058 A1 | 4/1991 |
| WO | WO-9303151 A1 | 2/1993 |
| WO | WO-9308278 A1 | 4/1993 |
| WO | WO-9321340 A1 | 10/1993 |
| WO | WO-9416332 A1 | 7/1994 |
| WO | WO-9423738 A1 | 10/1994 |
| WO | WO-9424314 A1 | 10/1994 |
| WO | WO-9426766 A1 | 11/1994 |
| WO | WO-9511922 A1 | 5/1995 |
| WO | WO-9524929 A3 | 12/1995 |
| WO | WO-9634112 A1 | 10/1996 |
| WO | WO-9640723 A1 | 12/1996 |
| WO | WO-9740141 A2 | 10/1997 |
| WO | WO-9747763 A1 | 12/1997 |
| WO | WO-9813502 A3 | 7/1998 |
| WO | WO-9823733 A3 | 7/1998 |
| WO | WO-9831700 A1 | 7/1998 |
| WO | WO-9834120 A1 | 8/1998 |
| WO | WO-9835012 A2 | 8/1998 |
| WO | WO-9837186 A1 | 8/1998 |
| WO | WO-9841869 A1 | 9/1998 |
| WO | WO-9844151 A1 | 10/1998 |
| WO | WO-9844152 A1 | 10/1998 |
| WO | WO-9850782 A2 | 11/1998 |
| WO | WO-9902671 A1 | 1/1999 |
| WO | WO-9930823 | 6/1999 |
| WO | WO-9932654 | 7/1999 |
| WO | WO-0004139 A1 | 1/2000 |
| WO | WO-0015842 A1 | 3/2000 |
| WO | WO-0018957 A1 | 4/2000 |
| WO | WO-0040712 A1 | 7/2000 |
| WO | WO-0060114 A2 | 7/2000 |
| WO | WO-0063437 A2 | 10/2000 |
| WO | WO-0075373 A2 | 12/2000 |
| WO | WO-0118244 A2 | 3/2001 |
| WO | WO-0120039 A2 | 3/2001 |
| WO | WO-0146471 A1 | 6/2001 |
| WO | WO-0153532 A2 | 7/2001 |
| WO | WO-0157268 A2 | 8/2001 |
| WO | WO-0212897 A9 | 2/2002 |
| WO | WO-0220836 A2 | 3/2002 |
| WO | WO-0220837 A2 | 3/2002 |
| WO | WO-0222869 A2 | 3/2002 |
| WO | WO-02077287 A1 | 10/2002 |
| WO | WO-02103363 A2 | 12/2002 |
| WO | WO-03004690 A2 | 1/2003 |
| WO | WO-03044187 A2 | 5/2003 |
| WO | WO-03054142 A2 | 7/2003 |
| WO | WO-02103011 A3 | 3/2004 |
| WO | WO-03045310 A9 | 7/2004 |
| WO | WO-04083443 A1 | 9/2004 |

(56) References Cited

FOREIGN PATENT DOCUMENTS

| WO | WO-05010145 A3 | 8/2005 |
|---|---|---|
| WO | WO-04069849 A8 | 4/2007 |
| WO | WO-2007149432 A2 | 12/2007 |

OTHER PUBLICATIONS

U.S. Appl. No. 60/465,071, filed Apr. 23, 2003, Lohman.
U.S. Appl. No. 60/476,313, filed Jun. 6, 2003, Chen et al.
U.S. Appl. No. 60/476,504, filed Jun. 6, 2003, Berka et al.
U.S. Appl. No. 60/476,592, filed Jun. 6, 2003, Leamon et al.
U.S. Appl. No. 60/476,602, filed Jun. 6, 2003, Costa et al.
U.S. Appl. No. 60/497,985, filed Aug. 25, 2003, Leamon et al.
Advisory Action issued in U.S. Appl. No. 10/767,899 dated Aug. 29, 2007.
Anarbaev et al. "Klenow Fragment and DNA Polymerase ☐-Primase Fromserva Calf Thymus in Water-in-Oil Microemulsions." *Biochim. Biophys. Acta*. 1384(1998):315-324.
Andras et al. "Strategies for Signal Amplification in Nucleic Acid Detection." *Mol. Biotechnol*. 19.1(2001):29-44.
Andreadis et al. "Use of Immobilized PCR Primers to Generate Covalently Immobilized DNAs for in vitro Transcription/Translation Reactions." *Nucleic Acids Res*. 28.2(2000):e5, i-viii.
Atwell et al. "Selection for Improved Subtiligases by Phage Display." *PNAS*. 96(1999):9497-9502.
Bans et al. "A Novel Method for Nucleic Acid Sequence Determination." *J. Theor. Biol*. 135.3(1988):303-307.
Bass et al. "Hormone Phage: An Enrichment Method for Variant Proteins With Altered Binding Properties." *Proteins: Structure, Function, and Genetics*. 8(1990):309-314.
Brody et al. "A Self-Assembled Microlensing Rotational Probe." *Appl. Phys. Lett*. 74(1999):144-146.
Bruckner-Lea et al. "Renewable Microcolumns for Automated DNA Purification and Flow-Through Amplification: From Sediment Samples Through Polymerase Chain Reaction." *Anal. Chim. Acta*. 21616(2000): 1-12.
Bruno et al. "Development of an Immunomagnetic Assay System for Rapid Detection of Bacteria and Leukocytes in Body Fluids." *J. Mol. Recog*. 9(1996):474-479.
Buck et al. "Design Strategies and Performance of Custome DNA Sequencing Primers." *BioTech*. 27(1999):528-536.
Chakrabarti et al. "Production of RNA by a Polymerase Protein Encapsulated Within Phopholipid Vesicles." *J. Mol. Evol*. 39(1994):555-559.
Chandler et al. "Effect of PCR Template Concentration on the Composition and Distribution of Total Community 16s rDNA Clone Libraries." *Mol. Ecol*. 6.5(1997):475-482.
Chapman et al. "in vitro Selection of Catalytic RNAs." *Struct. Biol*. 4(1994):618-622.
Chiou et al. "A Closed-Cycle Capillary Polymerase Chain Reaction Machine." *Anal. Chem*. 73.9(2001):2018-2021.
Clackson et al. "in vitro Slection From Protein and Peptide Libraries." *Trends Biotechnol*. 12(1994):173-184.
Claims Listing from European Application No. 1522582 B1.
Commencement of Proceedings before the Board of Appeal for European Patent Application No. 04706051.2 (European U.S. Pat. Patent No. 1594980) dated Jan. 10, 2012.
Communication and Terminal Disclaimers filed in U.S. Appl. No. 13/033,240 dated Sep. 16, 2011.
Communication pursuant to Article 94(3) EPC issued in European Patent Application No. 10184602.02403 dated Oct. 18, 2012.
Communication pursuant to Article 94(3) EPC issued in European Application No. 04706051.2 dated Apr. 9, 2008.
Communication pursuant to Article 94(3) EPC issued in European Application No. 04706051.2 dated Nov. 27, 2008.
Communication Pursuant to Article 94(3) EPC issued in European Patent Application No. 07019329.72403, dated Mar. 7, 2012.
Communication Pursuant to Article 94(3) EPC issued in European Patent Application No. 09166658.6 dated Jan. 26, 2012.
Communication pursuant to Article 96(2) EPC issued in European Application No. 04706051.2 dated Jul. 11, 2007.
Communication under Rule 71(3) EPC issued in European Patent Application No. 07019329.7-2403 dated Sep. 3, 2012.
Communication under Rule 71(3) EPC issued in European Application No. 04706051.2 dated May 25, 2009.
Communication under Rule 71(3) EPC issued in European Application No. 09175588.4 dated Oct. 21, 2011.
Communication under Rule 71(3) EPC issued in European Patent Application No. 07013020.8-2403 dated Mar. 7, 2012.
Communication under Rule 71(3) EPC issued in European Patent Application No. 10179652.2 dated Mar. 5, 2012.
Cull et al. "Screening for Receptor Ligands Using Large Libraries of Peptides Linked to the C Terminus of the lac Repressor." *PNAS*. 89(1992):1865-1869.
Decision to Grant a European Patent Pursuant to Article 97(1) EPC issued in European Patent Application No. 09175588.4-2403, dated Jan. 26, 2012.
Decision to Grant a European Patent Pursuant to Article 97(1) EPC issued in European Patent Application No. 07019329.7-2403 dated Nov. 29, 2012.
Decision to Grant a European Patent Pursuant to Article 97(1) EPC issued in European Patent Application No. 09166658.6-2403 dated Aug. 30, 2012.
Decision to Grant a European Patent Pursuant to Article 97(1) EPC issued in European Patent Application No. 10179652.2-2403 dated Jul. 27, 2012.
Decision to grant a European Patent Pursuant to Article 97(1) EPC issued in European Application No. 04706051.2 dated Oct. 15, 2009.
Deiman et al. "Characteristics and Applications of Nucleic Acid Sequence-Based Amplification (NASBA)." *Mol. Biotechnol*. 20.2(2000):163-179.
Demartis et al. "A Strategy for the Isolation of Catalytic Activities From Repertoires of Enzymes Displayed on Phage." *J. Mol. Biol*. 286(1999):617-633.
Dramanac et al. "Sequencing of Megabase Plus DNA by Hybridization: Theory of the Method." *Genomics*. 4.2(1989): 114-128.
Dressman et al. "Transforming Single DNA Molecules Into Fluorescent Magnetic Particles for Detection and Enumeration of Genetic Variations." *PNAS*. 100.15(2003):8817-8822.
Drmanc et al. "Prospects for a Miniaturized, Simplified and Frugal Human Genome Project." *Scientia Yugoslavica*. 16.1-2(1990):97-107.
Eigen et al. "Hypercycles and Compartments." *J. Theor. Biol*. 85(1980):407-411.
Eigen et al. "The Hypercycle." *Biochem*. 30.46(1991):11005-11018.
Eigen. "Wie entsteht Information? Prinzipien der Selbstorganisation in der Biologie." *Berichte der Bunsen-Gesellschaft fur Physikalische Chemie*. 80.11(1976): 1059-1081.
Ellington et al. "In vitro Selection of RNA Molecules That Bind Specific Ligands." *Nature*. 346(1990): 818-822.
Erlich, ed. *PCR Technology: Principles and Applications for DNA Amplification*. New York: M Stockton Press. (1989):50-53.
Extended European Search Report issued in European Application No. 09175588.4 dated Mar. 1, 2011.
Extended Search Report issued in European Patent Application No. 10184602.0-2403 dated Feb. 21, 2012.
Fan et al. "Dynamic DNA Hybridization on a Chip Using Paramagnetic Beads." *Anal. Chem*. 71.21(1999):4851-4859.
Final Office Action issued in U.S. Appl. No. 10/767,899 dated May 10, 2007.
Final Office Action issued in U.S. Appl. No. 10/767,899 dated Mar. 3, 2009.
Final Office Action issued in U.S. Appl. No. 13/045,210 dated May 11, 2012.
Final Written Submissions by Life Technologies Corporation in Opposition to European Patent No. 1594980, mailed Jul. 21, 2011.
Fry et al. "A New Approach to Template Purification for Sequencing Appliations Using Paramagnetic Particles." *BioTechniques*. 13.1(1992):124.
Gašperlin et al. "The Tructure Elucidation of Semisolid w/o Emulsion Systems." *Int. J. Pharm*. 107.1(1994):51-56.

(56) References Cited

OTHER PUBLICATIONS

Gašperlin et al. "Viscosity Prediction of Lipophilic Semisolid Emulsion Systems by Neural Network Modelling." *Int. J. Pharm.* 196(2000):37-50.
Ghadessy et al. "Directed Evolution of Polymerase Function by Compartmentalized Self-Replication." *PNAS.* 98.8(2001):4552-4557.
Gold et al. "Diversity of Oligonucleotide Functions." *Annu. Rev. Biochem.* 64(1995):763-797.
Green et al. "Selection of a Ribozyme That Functions as a Superior Template in a Self-Copying Reaction." *Science.* 258(1992):1910-1915.
Griffiths et al. "Directed Evolution of an Extremely Fast Phosphotriesterase by in vitro Compartmentalization." *EMBO J.* 22.1(2003):24-35.
Hanes et al. "In vitro Selection and Evolution of Functional Proteins by Using Ribosome Display." *Natl. Acad. Sci.* 94(1997):4937-4942.
Hawkins et al. "Whole Genome Amplification—Applications and Advances." *Curr. Opin. Biotechnol.* 13.1(2002):65-67.
Hsu et al. "Comparison of Process Parameters for Microencapsulation of Plasmid DNA in Poly(D,L-lactic-co-glycolic) Acid Microspheres." *J. Drug Target.* 7.4(1999):313-323.
Hultman et al. "Direct Solid Phase Sequencing of Genomic and Plasmid DNA Using Magnetic Beads as Solid Support." *Nucl. Acids Res.* 17.13(1989):4937-4946.
Information Disclosure Statement filed in U.S. Appl. No. 13/045,210, filed Sep. 25, 2012.
Interlocutory Decision in Opposition Proceedings (Art. 101(3)(a) and 106(2) EPC) in Opposition to European Patent No. 194980, mailed Oct. 27, 2011.
International Search Report issued in International Application No. PCT/US2004/02484 dated Feb. 15, 2005.
Janda et al. "Chemical Selection for Catalysis in Combinatorial Antibody Libraries." *Science.* 275(1997):945-948.
Jestin et al. "A Method for the Selection of Catalytic Activity Using Phage Display and Proximity Coupling." *Angew. Chem. Int. Ed.* 38.8(1999):1124-1127.
Joyce et al. "In vitro Evolution of Nucleic Acids." *Struct. Biol.* 4(1994):331-336.
Katsura et al. "Indirect Micromanipulation of Single Molecules in Water-in-Oil Emulsion." *Electrophoresis.* 22(2001):289-293.
Kawakatsu et al. "Regular-Sized Cell Creation in Microchannel Emulsification by Visual Microprocessing Method." *J. Am. Oil Chem. Soc.* 74(1997):317-321.
Keij et al. "High-Speed Photodamage Cell Sorting: An Evaluation of the ZAPPER Prototype." *Meth. Cell Biol.* 42(1994):371-386.
Khrapko et al. "An Oligonucleotide Hybridization Approach to DNA Sequencing." *FEBS Lett.* 256.1-2(1989):118-122.
Kopp et al. "Chemical Amplification: Continuous-Flow PCR on a Chip." *Science.* 280(1998):1046-1048.
Kwoh et al. "Transcription-Based Amplification System and Detection of Amplified Human Immunodeficiency Virus Type 1 With a Bead-Based Sandwich Hybridization Format." *PNAS.* 86.4(1989):1173-1177.
Letter From Charles A. Holland to Michelle A. Iwamoto dated May 10, 2011 and Declaration of Devin Dressman, et al., filed on Mar. 17, 2010 Under Rule 131 With Exhibits A-K, Executed on Mar. 15, 2010 and Mar. 16, 2010 (Two Counterparts) in U.S. Appl. No. 12/361,690.
Lund et al. "Assessment of Methods for Covalent Binding of Nucleic Acids to Magnetic Beads, Dynabeads™, and the Characteristics of the Bound Nucleic Acids in Hybridization Reactions." *Nucl. Acids Res.* 16.22(1998): 10861-10880.
Lundeberg et al. "Solid-Phase Technology: Magnetic Beads to Improved Nucleic Acid Detection and Analysis." *Biotechnol. Annu. Rev.* 1(1995):373-401.
Lysov et al. "Determination of the Nucleotide Sequencing of DNA Using Hybridization With Oligonucleotides." *Dkl Akad Nauk SSSR.* 303.6(1988):1508-1511. (No English Translation Available).

Margulies et al. "Genome Sequencing in Microfabricated High-Density Picolitre Reactors." *Nature.* 437(2005):376-380.
Margulies et al. "Supplementary Methods for the Article 'Genome Sequencing in Microfabricated High-Density Picolitre Reactors.'" *Nature.* 437.7057(2005):1-34. (including supplementary tables and figures).
Mattheakis et al. "An in vitro Polysome Display System for Identifying Ligands From Very Large Peptide Libraries." *PNAS.* 91(1994):9022-9026.
Maxam et al. "A New Method for Sequencing DNA." *PNAS.* 74.2(1977):560-564.
McCafferty et al. "Phage Antibodies: Filamentous Phage Displaying Antibody Variable Domains." *Nature.* 348(1990):552-554.
Merrifield. "Solid-Phase Peptide Synthesis." *Biochem.* 3.9(1964):1385-1390.
Moore. "Exploration by Lamp Light." *Nature.* 374(1995):766-767.
Nagai et al. "Development of a Microchamber Array for Picoliter PCR." *Anal. Chem.* 73.5(2001):1043-1047.
Nakano et al. "High Speed Polymerase Chain Reaction in Constant Flow." *Biosci. Biotechnol. Biochem.* 58.2(1994):349-352.
Nakano et al. "Single-Molecule PCR Using Water-in-Oil Emulsion." *J. Biotechnol.* 102.2(2003):117-124.
Nemoto et al. "In vitro Virus: Bonding of mRNA Bearing Puromycin at the 3'-Terminal End to the C-Terminal End of its Encoded Protein on the Ribosome in vitro." *Fed. Eur. Biochem. Soc.* 414.2(1997):405-408.
Nisisako et al. "Rapid Preparation of Monodispersed Droplets With Confluent Laminar Flows." *IEEE.* (2003):331-334.
Non-Final Office Action issued in U.S. Appl. No. 10/767,899 dated Dec. 11, 2007.
Non-Final Office Action issued in U.S. Appl. No. 10/767,899 dated Jul. 30, 2008.
Non-Final Office Action issued in U.S. Appl. No. 10/767,899 dated Nov. 20, 2006.
Non-Final Office Action issued in U.S. Appl. No. 10/767,899 dated Nov. 5, 2009.
Notice of Appeal for European Patent Application No. 04706051.2 (European Patent No. 1594980), dated Jan. 3, 2012.
Notice of Opposition to a European Patent No. 1594980 mailed Aug. 9, 2010.
Obeid et al. "Microfabricated Device for DNA and RNA Amplification by Continuous-Flow Polymerase Chain Reaction and Reverse Transcriptio-Polymerase Chain Reaction With Cycle Number Selection." *Anal. Chem.* 86(2003):288-295.
Oberholzer et al. "Enzymatic RNA Replication in Self-Reproducing Vesicles: An Approach to a Minimal Cell." *Biochem. Biophys. Res. Commun.* 207(1995):250-257.
Oberholzer et al. "Polymerase Chain Reaction in Liposomes." *Chem. Biol.* 2.10(1995):677-682.
Office Action issued in Australian Application No. 2004209001 dated Jul. 20, 2006.
Office Action issued in Australian Application No. 2008200151 dated Aug. 25, 2010.
Office Action issued in Australian Application No. 2008200151 dated May 13, 2010.
Office Action issued in Canadian Application No. 2,513,535 dated Aug. 17, 2010.
Office Action issued in Canadian Application No. 2,513,535 dated May 9, 2011.
Office Action issued in Japanese Application No. 2006-503133 dated Feb. 19, 2009. (English Translation and Japanese Original).
Office Action issued in Japanese Application No. 2006-503133 dated Nov. 17, 2010. (English Translation and Japanese Original).
Office Action issued in Japanese Application No. 2006-503133 dated Sep. 10, 2009. (English Translation and Japanese Original).
Office Action issued in Japanese Application No. 2010-053827 dated Aug. 29, 2012. (Japanese Original and English Translation).
Ohara et al. "One-Sided Polymerase Chain Reaction: The Amplification of cDNA." *PNAS.* 86(1989):5673-5677.
Park et al. "Cylindrical Compact Thermal-Cycling Device for Continuous-Flow Polymerase Chain Reaction." *Anal. Chem.* 75(2003):6029-6033.

(56) References Cited

OTHER PUBLICATIONS

Patentee's Observations on the Opposition Filed Against EP 1594980 B1 mailed Jan. 17, 2011.
Patentee's Response to Communication from Opposition Division Relating to EP 1594980 (European Patent Application No. 04706051.2), mailed Jul. 20, 2011.
Pedersen et al. "A Method for Directed Evolution and Functional Cloning of Enzymes." *PNAS.* 95(1998):10523-10528.
Pelletier et al. "An in vivo Library-Versus-Library Selection of Optimized Protein-Protein Interactions." *Nat. Biotechnol.* 17(1999):683-690.
Pevzner. "1-Tuple DNA Sequencing: Computer Analysis." *J. Biomol. Struct. Dyn.* 7.1(1989):63-73.
Polz et al. "Bias in Template-to-Product Ratios in Multitemplate PCR." *Appl. Environ. Microbiol.* 64(1998):37424-3730.
Provision of the Minutes in Accordance With Rule 124(4) EPC in Opposition to European Patent No. EP 1594980, mailed Oct. 27, 2011.
Reply to Communication Under Rule 71(3) filed in European Patent Application No. 09175588.4 dated Dec. 16, 2011.
Request for Continued Examination filed in U.S. Appl. No. 13/045,210 dated Aug. 28, 2012.
Response to Communication Pursuant to Article 94(3) EPC issued in European Patent Application No. 07019329.7-2403 dated Jul. 2, 2012.
Response to Communication Pursuant to R.69 EPC and Invitation Pursuant to R.70a(1) issued in European Patent Application No. 10184602.0 dated Sep. 18, 2012.
Response to Communication under EPCr.71(3) issued in European Patent Application No. 07019329.7-2403 dated Nov. 13, 2012.
Response to Communication under Rule 71(3) EPC issued in European Patent Application No. 07013020.8-2403 dated Jun. 26, 2012.
Response to Communication under Rule 71(3) EPC issued in European Patent Application No. 09166658.6 dated Aug. 17, 2012.
Response to Communication Under Rule 71(3) EPC issued in European Patent Application No. 10179652.2-2403 dated Jun. 26, 2012.
Response to Statement of Grounds of Appeal filed by Life Technologies Corporation issued in European Patent No. EP1594980 dated Jul. 12, 2012.
Roberts et al. "RNA-Peptide Fusions for the in vitro Selection of Peptides and Proteins." *PNAS.* 94(1997):12297-12302.
Ronaghi et al. "A Sequencing Method Based on Real-Time Pyrophosphate." *Science.* 281(1998):363-365.
Rubin et al. "A Mathematical Model and a Computerized Simulation of PCR Using Complex Templates." *Nucl. Acids Res.* 24.18(1996):3538-3545.
Russom et al. "Single-Nucleotide Polymorphism Anlysis by Allele-Specific Extension of Fluorescently Labeled Nucleotides in a Microfluidic Flow-Through Device." *Electrophoresis.* 24(2003):158-161.
Ruzicka et al. "Lab-on-Valve: Universal Microflow Analyzer Based on Sequential and Bead Injection." *Analyst.* 125(2000):1053-1060.
Sanger et al. "DNA Sequencing With Chain-Terminating Inhibitors." *PNAS.* 74.12(1977):5463-5467.
Schneegass et al. "Flow-Through Polymerase Chain Reactions in Chip Thermocyclers." *Rev. Mol. Biotechnol.* 82(2001):101-121.
Schneegass et al. "Miniaturized Flow-Through PCR With Different Template Types in a Silicon Chip Thermocycler." *Lab on a Chip.* 1(2001):42-49.
Sepp et al. "Microbead Display by in vitro Compartmentalization: Selection for Binding Using Flow Cytometry." *FEBS Lett.* 532.3(2002):455-458.
Smith. "Filamentous Fusion Phage: Novel Expression Vectors That Display Cloned Antigens on the Virion Surface." *Science.* 228(1985):1315-1317.
Soumillion. "Selection of □-Lactamase on Filmentous Bacteriophage by Catalytic Activity." *J. Mol. Biol.* 237(1994):415-422.
Southern et al. "Analyzing and Comparing Nucleic Acid Sequences by Hybridization to Arrays of Oligonucleotides: Evaluation Using Experimental Models." *Genomics.* 13(1992):1008-1017.
Statement of Grounds of Appeal on Behalf of the Opponent Life Technologies Corporation, Appeal No. T0014/12-3.3.08 (European Patent No. EP-B-1594980; European Patent Application No. 04706051.2), dated Mar. 6, 2012.
Strizhkov et al. "PCR Amplification on a Microarray of Gel-Immobilized Oligonucleotides: Detection of Bacterial Toxin- and Drug-Resistant Genes and Their Mutations." *BioTechniques.* 29.4(2000):844-857.
Summons to Attend Oral Proceedings Pursuant to Rule 115(1) EPC and Preliminary Opinion of the EPO Opposition Division in the Opposition Filed Against EP 1594980 dated Mar. 24, 2011.
Supplemental Information Disclosure Statement filed in U.S. Appl. No. 13/033,240, on Sep. 9, 2011.
Supplementary Search Report issued in European Application No. 04706051 dated Mar. 22, 2007.
Suzuki et al. "Bias Caused by Template Annealing in the Amplification of Mixtures of 16S rRNA Genes by PCR." *Appl. Environ. Microbiol.* 62.2(1996):625-630.
Suzuki et al. "Random Mutagenesis of *Thermus aquaticus* DNA Polymerase I: COncordance of Immutable Sites in vitro With the Crystal Structure." *PNAS.* 93(1996):9670-9675.
Tawfik et al. "Efficient and Selective p-Nitrophenyl-Ester-Hydrolyzing Antibodies Elicited by a p-Nitrobenzyl Phosphonate Hapten." *Eur. J. Biochem.* 244(1997):619-626.
Tawfik et al. "Man-Made Cell-Like Compartments for Molecular Evolution." *Nat. Biotechnol.* 16(1998):652-656.
Tuerk et al. "Systemic Evolution of Ligands by Exponential Enrichment: RNA Ligands to Bacteriophage T4 DNA Polymerase." *Science.* 249(1990):505-510.
United States Patent and Trademark Office Board of Patent Appeals and Interferences, 454 Annotated Copy of Claims in Patent Interference No. 105,857 (Nov. 10, 2011).
United States Patent and Trademark Office Board of Patent Appeals and Interferences, 454 Clean Copy of Claims in Patent Interference No. 105,857 (Oct. 27, 2011).
United States Patent and Trademark Office Board of Patent Appeals and Interferences, 454 Contingent Motion 3 in Patent Interference No. 105,857 dated Mar. 14, 2012.
United States Patent and Trademark Office Board of Patent Appeals and Interferences, 454 Contingent Reply 3 (to add a claim to the 454 application) in Patent Interference No. 105,857 dated Jul. 16, 2012.
United States Patent and Trademark Office Board of Patent Appeals and Interferences, 454 Corrected Demonstrative Exhibits (for Sep. 11, 2012 Oral Argument) in Patent Interference No. 105,857 dated Sep. 10, 2012.
United States Patent and Trademark Office Board of Patent Appeals and Interferences, 454 Demonstrative Exhibits (for Sep. 11, 2012 Oral Argument) in Patent Interference No. 105,857 dated Sep. 4, 2012.
United States Patent and Trademark Office Board of Patent Appeals and Interferences, 454 Designation of Lead and Backup Counsel in Patent Interference No. 105,857 (Oct. 27, 2011).
United States Patent and Trademark Office Board of Patent Appeals and Interferences, 454 Exhibit List in Patent Interference No. 105,857 dated Aug. 10, 2012.
United States Patent and Trademark Office Board of Patent Appeals and Interferences, 454 Identification of Real Party in Interest in Patent Interference No. 105,857 (Oct. 27, 2011).
United States Patent and Trademark Office Board of Patent Appeals and Interferences, 454 Life Sciences Request to File Motion to Add Application (motion to add Johns Hopkins University Application No. 1/311,120) in Patent Interference No. 105,857 (Dec. 15, 2011).
United States Patent and Trademark Office Board of Patent Appeals and Interferences, 454 List of Proposed Motions in Patent Interference No. 105,857 (Dec. 5, 2011).
United States Patent and Trademark Office Board of Patent Appeals and Interferences, 454 Motion 1 for Benefit in Patent Interference No. 105,857 dated Feb. 22, 2012.

(56) References Cited

OTHER PUBLICATIONS

United States Patent and Trademark Office Board of Patent Appeals and Interferences, 454 Motion 2 for Judgment of Unpatentability in Patent Interference No. 105,857 dated Feb. 22, 2012.

United States Patent and Trademark Office Board of Patent Appeals and Interferences, 454 Notice of Change of Address of Lead and Backup Counsel in Patent Interference No. 105,857 dated Feb. 21, 2012.

United States Patent and Trademark Office Board of Patent Appeals and Interferences, 454 Notice of Filing Priority Statement in Patent Interference No. 105,857 dated Feb. 22, 2012.

United States Patent and Trademark Office Board of Patent Appeals and Interferences, 454 Notice of Intent to Video-Record the Cross-Examination of Jay A. Shendure, M.D., Ph.D. in Patent Interference No. 105,857 dated Jun. 7, 2012.

United States Patent and Trademark Office Board of Patent Appeals and Interferences, 454 Notice of Intent to Video-Record the Cross-Examination of Jay A. Shendure, M.D., Ph.D. in Patent Interference No. 105,857 dated Mar. 28, 2012.

United States Patent and Trademark Office Board of Patent Appeals and Interferences, 454 Notice of Related Proceedings in Patent Interference No. 105,857 (Oct. 27, 2011).

United States Patent and Trademark Office Board of Patent Appeals and Interferences, 454 Notice of Submission of Record in Patent Interference No. 105,857 dated Aug. 10, 2012.

United States Patent and Trademark Office Board of Patent Appeals and Interferences, 454 Opposition 1 (Responsive to motion attacking benefit accorded 454) in Patent Interference No. 105,857 dated May 21, 2012.

United States Patent and Trademark Office Board of Patent Appeals and Interferences, 454 Opposition 2 (Responsive to motion for judgment based on 35 U.S.C. §135(b)(2)) in Patent Interference No. 105,857 dated May 21, 2012.

United States Patent and Trademark Office Board of Patent Appeals and Interferences, 454 Priority Statement in Patent Interference No. 105,857 (Feb. 22, 2012).

United States Patent and Trademark Office Board of Patent Appeals and Interferences, 454 Reply 1 for Benefit in Patent Interference No. 105,857 dated Jul. 16, 2012.

United States Patent and Trademark Office Board of Patent Appeals and Interferences, 454 Request for Oral Argument in Patent Interference No. 105,857 dated Jul. 20, 2012.

United States Patent and Trademark Office Board of Patent Appeals and Interferences, 454 Updated Notice of Related Proceedings in Patent Interference No. 105,857 (Dec. 14, 2011).

United States Patent and Trademark Office Board of Patent Appeals and Interferences, Appearance Record in Interference No. 105,857 dated Sep. 11, 2012.

United States Patent and Trademark Office Board of Patent Appeals and Interferences, Decision on Motions—Bd.R. 125(a) in Interference No. 105,857 dated Sep. 24, 2012.

United States Patent and Trademark Office Board of Patent Appeals and Interferences, Declaration in Patent Interference No. 105,857 dated Oct. 13, 2011.

United States Patent and Trademark Office Board of Patent Appeals and Interferences, JHU Opposition 1 in Patent Interference No. 105,857 dated May 21, 2012).

United States Patent and Trademark Office Board of Patent Appeals and Interferences, JHU Opposition 2 in Patent Interference No. 105,857 dated May 21, 2012.

United States Patent and Trademark Office Board of Patent Appeals and Interferences, JHU Opposition 3 in Patent Interference No. 105,857 dated May 21, 2012.

United States Patent and Trademark Office Board of Patent Appeals and Interferences, Johns Hopkins Annotated Copy of Claims in Patent Interference No. 105,857 (Nov. 10, 2011).

United States Patent and Trademark Office Board of Patent Appeals and Interferences, Johns Hopkins Brief on Pertinence of Spina-Agilent-Philips Line of Cases in Patent Interference No. 105,857 dated Dec. 14, 2011.

United States Patent and Trademark Office Board of Patent Appeals and Interferences, Johns Hopkins Clean Copy of Claims in Patent Interference No. 105,857 (Oct. 27, 2011).

United States Patent and Trademark Office Board of Patent Appeals and Interferences, Johns Hopkins Filing of Attachment to Priority Statement in Patent Interference No. 105,857 dated Feb. 28, 2012.

United States Patent and Trademark Office Board of Patent Appeals and Interferences, Johns Hopkins Identification of Lead and Backup Counsel in Patent Interference No. 105,857 (Oct. 27, 2011).

United States Patent and Trademark Office Board of Patent Appeals and Interferences, Johns Hopkins List of Proposed Motions in Patent Interference No. 105,857 (Dec. 5, 2011).

United States Patent and Trademark Office Board of Patent Appeals and Interferences, Johns Hopkins Miscellaneous Motion No. 1 (requesting substitution of exhibit) in Interference No. 105,857 (Dec. 11, 2012).

United States Patent and Trademark Office Board of Patent Appeals and Interferences, Johns Hopkins Motion 1 in Patent Interference No. 105,857 dated Feb. 21, 2012.

United States Patent and Trademark Office Board of Patent Appeals and Interferences, Johns Hopkins Motion 3 (for judgment based on priority) in Interference No. 105,857 (Dec. 11, 2012).

United States Patent and Trademark Office Board of Patent Appeals and Interferences, Johns Hopkins Notice of Filing Priority Statement in Patent Interference No. 105,857 dated Feb. 21, 2012.

United States Patent and Trademark Office Board of Patent Appeals and Interferences, Johns Hopkins Notice of Real Party in Interest in Patent Interference No. 105,857 (Oct. 27, 2011).

United States Patent and Trademark Office Board of Patent Appeals and Interferences, Johns Hopkins Notice of Related Proceedings in Patent Interference No. 105,857 (Oct. 27, 2011).

United States Patent and Trademark Office Board of Patent Appeals and Interferences, Johns Hopkins Priority Statement in Patent Interference No. 105,857 (Feb. 21, 2012).

United States Patent and Trademark Office Board of Patent Appeals and Interferences, Johns Hopkins Reply 1 (attacking benefit accorded 454) in Patent Interference No. 105,857 dated Jul. 13, 2012.

United States Patent and Trademark Office Board of Patent Appeals and Interferences, Johns Hopkins Reply 2 (for judgment based on 35 U.S.C. §135(b)(2)) in Patent Interference No. 105,857 dated Jul. 11, 2012.

United States Patent and Trademark Office Board of Patent Appeals and Interferences, Johns Hopkins Request for File Copies in Patent Interference No. 105,857 (Oct. 27, 2011).

United States Patent and Trademark Office Board of Patent Appeals and Interferences, Johns Hopkins Request for Oral Argument in Patent Interference No. 105,857 dated Jul. 20, 2012.

United States Patent and Trademark Office Board of Patent Appeals and Interferences, Johns Hopkins Substantive Motion 2 in Patent Interference No. 105,857 dated Feb. 21, 2012.

United States Patent and Trademark Office Board of Patent Appeals and Interferences, Johns Hopkins University Exhibit List in Patent Interference No. 105,857 (Jul. 23, 2012).

United States Patent and Trademark Office Board of Patent Appeals and Interferences, Johns Hopkins Updated Notice of Related Proceedings in Patent Interference No. 105,857 (Dec. 5, 2011).

United States Patent and Trademark Office Board of Patent Appeals and Interferences, Johns Hopkins' Service of Corrected Demonstrative Exhibit in Patent Interference No. 105,857 dated Sep. 7, 2012.

United States Patent and Trademark Office Board of Patent Appeals and Interferences, Johns Hopkins' Service of Demonstrative Exhibits in Patent Interference No. 105,857 dated Sep. 4, 2012.

United States Patent and Trademark Office Board of Patent Appeals and Interferences, Johns Hopkins' Submission of Record in Patent Interference No. 105,857 dated Aug. 11, 2012.

United States Patent and Trademark Office Board of Patent Appeals and Interferences, Johns Hopkins' Updated Notice of Real Party in Interest in Patent Interference No. 105,857 (Jan. 6, 2012).

United States Patent and Trademark Office Board of Patent Appeals and Interferences, Joint Statement Regarding Settlement Discussions in Patent Interference No. 105,857 (Jan. 13, 2012).

(56) References Cited

OTHER PUBLICATIONS

United States Patent and Trademark Office Board of Patent Appeals and Interferences, Joint Statement Regarding Settlement Discussions in Patent Interference No. 105,857 (Nov. 21, 2012).
United States Patent and Trademark Office Board of Patent Appeals and Interferences, Joint Stipulation Regarding Time Period 1 in Patent Interference No. 105,857 dated Feb. 21, 2012.
United States Patent and Trademark Office Board of Patent Appeals and Interferences, Joint Stipulation Regarding Time Period 1 in Patent Interference No. 105,857 dated Jan. 26, 2012.
United States Patent and Trademark Office Board of Patent Appeals and Interferences, Joint Stipulation Regarding Time Period 11 in Patent Interference No. 105,857 (Nov. 9, 2012).
United States Patent and Trademark Office Board of Patent Appeals and Interferences, Joint Stipulation Regarding Time Period 12 in Interference No. 105,857 (Dec. 21, 2012).
United States Patent and Trademark Office Board of Patent Appeals and Interferences, Joint Stipulation Regarding Time Period 2 in Patent Interference No. 105,857 dated Feb. 28, 2012.
United States Patent and Trademark Office Board of Patent Appeals and Interferences, Joint Stipulation Regarding Time Period 2 in Patent Interference No. 105,857 dated Mar. 13, 2012.
United States Patent and Trademark Office Board of Patent Appeals and Interferences, Joint Stipulation Regarding Time Period 3 in Patent Interference No. 105,857 dated Apr. 25, 2012.
United States Patent and Trademark Office Board of Patent Appeals and Interferences, Joint Stipulation Regarding Time Period 4 in Patent Interference No. 105,857 dated May 29, 2012.
United States Patent and Trademark Office Board of Patent Appeals and Interferences, Joint Stipulation Regarding Time Periods 1-4 in Patent Interference No. 105,857 dated Feb. 10, 2012.
United States Patent and Trademark Office Board of Patent Appeals and Interferences, Joint Stipulation Regarding Time Periods 12-14 in Interference No. 105,857 (Jan. 17, 2013).
United States Patent and Trademark Office Board of Patent Appeals and Interferences, Joint Stipulation Regarding Time Periods 4 and 5 in Patent Interference No. 105,857 dated Jun. 21, 2012.
United States Patent and Trademark Office Board of Patent Appeals and Interferences, Joint Stipulation Regarding Time Periods 4-6 in Patent Interference No. 105,857 dated Jul. 3, 2012.
United States Patent and Trademark Office Board of Patent Appeals and Interferences, Minutes of September 11, 2012 Hearing in Interference No. 105,857 dated Oct. 4, 2012.
United States Patent and Trademark Office Board of Patent Appeals and Interferences, Opinion in Patent Interference No. 105,857 dated Dec. 6, 2011.
United States Patent and Trademark Office Board of Patent Appeals and Interferences, Order (Bd. R. 104(a)) in Patent Interference No. 105,857 dated Feb. 16, 2012.
United States Patent and Trademark Office Board of Patent Appeals and Interferences, Order (Bd. R. 121) in Patent Interference No. 105,857 dated Mar. 9, 2012.
United States Patent and Trademark Office Board of Patent Appeals and Interferences, Order (Bd. R. 124 Oral Argument) in Patent Interference No. 105,857 dated Aug. 15, 2012.
United States Patent and Trademark Office Board of Patent Appeals and Interferences, Order (Bd.R. 104 Dismissing 454 Motion 2 Moving Time Period 4) in Patent Interference No. 105,857 dated Jul. 3, 2012.
United States Patent and Trademark Office Board of Patent Appeals and Interferences, Order (Bd. R. 104 dismissing request for guidance) in Patent Interference No. 105,857 dated Mar. 27, 2012.
United States Patent and Trademark Office Board of Patent Appeals and Interferences, Order (Bd. R. 104(a)) in Patent Interference No. 105,857 dated Mar. 5, 2012.
United States Patent and Trademark Office Board of Patent Appeals and Interferences, Order (Bd. R. 124 transferring interference) in Patent Interference No. 105,857 dated Jul. 24, 2012.
United States Patent and Trademark Office Board of Patent Appeals and Interferences, Order Bd. R. 104 (regarding notice of real party-in-interest) in Patent Interference No. 105,857 (Dec. 12, 2011).
United States Patent and Trademark Office Board of Patent Appeals and Interferences, Order Bd. R. 109(b) (authorizing copies of office records) in Patent Interference No. 105,857 (Oct. 28, 2011).
United States Patent and Trademark Office Board of Patent Appeals and Interferences, Order Bd. R. 121 (regarding proposed motion to add an application) in Patent Interference No. 105,857 (Dec. 16, 2011).
United States Patent and Trademark Office Board of Patent Appeals and Interferences, Order Bd. R. 121(a) (authorizing motions) and Bd. R. 104(c) (setting motion times) in Patent Interference No. 105,857 (Dec. 8, 2011).
United States Patent and Trademark Office Board of Patent Appeals and Interferences, Order in Interference No. 105,857 dated Oct. 11, 2012.
United States Patent and Trademark Office Board of Patent Appeals and Interferences, Order in Patent Interference No. 105,857 dated Dec. 20, 2011.
Vainshtein et al. "Peptide Research of an N-Terminal Truncation of the Stoffel Fragment of Taq DNA Polymerase." *Protein Science*. 5(1996):1785-1792.
Vogelstein et al. "Digital PCR." *PNAS*. 96(1999):9236-9241.
Walde et al. "Oparin's Reactions Revisited: Enzymatic Synthesis of Poly(adenylic acid) in Micelles and Self-Reproducing Vesicles." *J. Am. Chem. Soc*. 116(1994):7541-7547.
Walker et al. "Isothermal in vitro Amplification of DNA by a Restriction Enzyme/DNA Polymerase System." *PNAS*. 89(1992):392-396.
Warburton. "Microcapsules From Multiple Emulsions." *Royal Soc. Chem*. 138(1993):35-51.
Wick. "Enzyme-Containing Liposomes can Endogenously Produce Membrane-Constituting Lipids." *Chem. Biol*. 3(1996):277-285.
Widersten et al. "Glutathion Transferases With Novel Active Sites Isolated by Phage Display From a Library of Random Mutants." *J. Mol. Biol*. 250(1995):115-122.
Yang et al. "Covalent Immobilization of Oligonucleotides on Modified Glass/Silicon Surfaces for Solid-Phase DNA Hybridization and Amplification." *Chem. Lett*. 27.3(1998):257-258.
Office Communication dated Jul. 30, 2014 in U.S. Appl. No. 95/001,765.
Third Party Requester's Request for Oral Hearing Under 37 CFR 41.73 filed Jul. 21, 2014 in U.S. Appl. No. 95/001,765.
Third Party Requester's Rebuttal Brief filed Jun. 23, 2014 in U.S. Appl. No. 95/001,765.
Patent Owner's Rebuttal Brief Under 37 CFR 41.71 filed Jun. 23, 2014 in U.S. Appl. No. 95/001,765.
Patent Owner's (Appellant's) Request for Oral Hearing filed Jun. 23, 2014 in U.S. Appl. No. 95/001,765.
Inter Partes Reexamination Examiner's Answer mailed May 21, 2014 in U.S. Appl. No. 95/001,765.
Patent Owner's Respondent's Brief under 37 CFR 41.68 filed Jan. 9, 2014 in U.S. Appl. No. 95/001,765.
Third Party Requester's Respondent Brief filed Jan. 9, 2014 in U.S. Appl. No. 95/001,765.
Patent Owner's (Appellant's) Brief under 37 CFR 41.67 filed Dec. 9, 2013 in U.S. Appl. No. 95/001,765.
Information Disclosure Statement filed Dec. 9, 2013 in U.S. Appl. No. 95/001,765.
Third Party Requester's Appellant Brief filed Dec. 9, 2013 in U.S. Appl. No. 95/001,765.
Notice of Cross-Appeal filed Oct. 7, 2013 in U.S. Appl. No. 95/001,765.
Notice of Appeal under 37 CFR 41.61(a)(1) filed Sep. 24, 2013 in U.S. Appl. No. 95/001,765.
Right of Appeal Notice (37 CFR 1.953) mailed Aug. 26, 2013 in U.S. Appl. No. 95/001,765.
Information Disclosure Statement filed Feb. 5, 2013 in U.S. Appl. No. 95/001,765.

(56) References Cited

OTHER PUBLICATIONS

Comments by Third Party Requester to Patentee's Amendment and Response to Office Action in Inter Partes Reexamination under 37 C.F.R. 1.947 filed Nov. 16, 2012 in U.S. Appl. No. 95/001,765.
Response filed Oct. 19, 2012 in U.S. Appl. No. 95/001,765.
Information Disclosure Statement filed Oct. 19, 2012 in U.S. Appl. No. 95/001,765.
Information Disclosure Statement filed Sep. 26, 2012 in U.S. Appl. No. 95/001,765.
Action Closing Prosecution (37 CFR 1.949) mailed Sep. 21, 2012 in U.S. Appl. No. 95/001,765.
Information Disclosure Statement filed Apr. 24, 2012 in U.S. Appl. No. 95/001,765.
Information Disclosure Statement filed Apr. 2, 2012 in U.S. Appl. No. 95/001,765.
Response filed Jan. 19, 2012 in U.S. Appl. No. 95/001,765.
Information Disclosure Statement filed Jan. 19, 2012 in U.S. Appl. No. 95/001,765.
Office Action in Inter Partes Reexamination dated Nov. 19, 2011 in U.S. Appl. No. 95/001,765.
Request for Inter Partes Reexamination mailed Sep. 15, 2011 in U.S. Pat. No. 8,012,690.
"Attach." Merriam-Webster. Web. Jul. 11, 2013. www.merriam-dictionary.com/dictionary/attach.
"Bind." Merriam-Webster. Web. Jul. 11, 2013. www.merriam-dictionary.com/dictionary/bind.
"Couple." Merriam-Webster. Web. Jul. 11, 2013. www.merriam-dictionary.com/dictionary/couple.
"Disposed." Merriam-Webster. Web. Aug. 2, 2013. http://1828.mshaffer.com/d/word/disposed.
Bauer. "Advances in Cell Separation: Recent Developments in Counterflow Centrifugal Elutriation and Continuous Flow Cell Separation." J. Chromatog. B. 722.1-2(1999):55-69.
Communication under Rule 71(3) EPC issued in European Application No. 05712801.9-1404 dated Feb. 12, 2013.
Decision to grant a European patent pursuant to Article 97(1) EPC issued in European Application No. 05712801.9-1404 dated Jun. 27, 2013.
Higuchi. "Using PCR to Engineer DNA." PCR Technology: Principles and Applications for DNA Amplification. Erlich, ed. New York: Stockton Press. Chapter 6(1989):61-63.
Notice of opposition to a European patent for European Patent No. EP1908832 dated Sep. 19, 2013.
Office Action issued in Chinese Application No. 201110079989.6 dated Jan. 21, 2013. (Chinese Original and English Translation).
Office Action issued in U.S. Appl. No. 11/788,838 dated Aug. 27, 2013.
Office Action issued in U.S. Appl. No. 12/317,213 dated Jun. 21, 2013.
Office Action issued in U.S. Appl. No. 13/419,241 dated Jan. 30, 2013.
Office Action issued in U.S. Appl. No. 13/618,334 dated Sep. 16, 2013.
Reply to communication under rule 71(3) EPC for European Application No. 05712801.9-1404 dated Jun. 10, 2013.
Response to communication pursuant to a.94(3) EPC for European Application No. 10184602.0 dated Apr. 8, 2013.
Rosenthal et al. "Capture PCR: An Efficient Method for Walking Along Chromosomal DNA and cDNA." PCR: The Polymerase Chain Reaction. Mullis et al., eds. Boston: Birkhauser. Chapter 19(1994):222-229.
U.S. Department of Commerce, U.S. Patent and Trademark Office, Patent Trial and Appeal Board, Appearance Record in Patent Interference No. 105,857 (Aug. 7, 2013).
United States Patent and Trademark Office Before the Patent Trial and Appeal Board, 454 Reply 3 (for judgment based on priority) in Patent Interference No. 105,857 (Jun. 3, 2013).
United States Patent and Trademark Office Before the Patent Trial and Appeal Board, Decision on Motions—Bd.R. 125(a) in Patent Interference No. 105,857 (Sep. 6, 2013).
United States Patent and Trademark Office Before the Patent Trial and Appeal Board, Joint Stipulation Regarding Time Period 12 in Patent Interference No. 105,857 (Feb. 21, 2013).
United States Patent and Trademark Office Before the Patent Trial and Appeal Board, Joint Stipulation Regarding Time Periods 12-16 in Patent Interference No. 105,857 (Feb. 7, 2013).
United States Patent and Trademark Office Before the Patent Trial and Appeal Board, Joint Stipulation Regarding Time Periods 14 and 15 in Patent Interference No. 105,857 (May 8, 2013).
United States Patent and Trademark Office Before the Patent Trial and Appeal Board, Judgment—37 CFR § 41.127 in Patent Interference No. 105,857 (Sep. 6, 2013).
United States Patent and Trademark Office Before the Patent Trial and Appeal Board, Order—Oral Argument—Bd.R. 124 in Patent Interference No. 105,857 (Jul. 12, 2013).
United States Patent and Trademark Office Before the Patent Trial and Appeal Board, Post Conference Call Order in Patent Interference No. 105,857 (Mar. 7, 2013).
United States Patent and Trademark Office Board of Patent Appeals and Interferences, Johns Hopkins Notices Pursuant to 37 C.F.R. § 41.8(b) and 90.2(c) in Patent Interference No. 105,857 (Nov. 7, 2013).
United States Patent and Trademark Office Board of Patent Appeals and Interferences, Johns Hopkins Request for Oral Argument in Patent Interference No. 105,857 (Jun. 5, 2013).
United States Patent and Trademark Office Board of Patent Appeals and Interferences, Johns Hopkins University Exhibit List in Patent Interference No. 105,857 (Jun. 21, 2013).
United States Patent and Trademark Office Board of Patent Appeals and Interferences, Johns Hopkins University Exhibit List in Patent Interference No. 105,857 (Jun. 3, 2013).
United States Patent and Trademark Office Board of Patent Appeals and Interferences, Johns Hopkins' Service of Demonstrative Exhibit in Patent Interference No. 105,857 (Jul. 31, 2013).
United States Patent and Trademark Office Board of Patent Appeals and Interferences, Johns Hopkins' Submission of Record in Patent Interference No. 105,857 (Jun. 21, 2013).
United States Patent and Trademark Office Board of Patent Appeals and Interferences, Joint Stipulation Regarding Time Period 13 in Patent Interference No. 105,857 (Mar. 19, 2013).
United States Patent and Trademark Office Patent Trial and Appeal Board, 454 Exhibit List (as of Apr. 26, 2013) in Patent Interference No. 105,857 (Apr. 26, 2013).
United States Patent and Trademark Office Patent Trial and Appeal Board, 454 Exhibit List in Patent Interference No. 105,857 (Feb. 27, 2013).
United States Patent and Trademark Office Patent Trial and Appeal Board, 454 Exhibit List in Patent Interference No. 105,857 (Jun. 21, 2013).
United States Patent and Trademark Office Patent Trial and Appeal Board, 454 Motion 3 (for judgment based on priority) in Patent Interference No. 105,857 (Feb. 27, 2013).
United States Patent and Trademark Office Patent Trial and Appeal Board, 454 Notice of Intent to Video-Record the Cross-Examination of Jay A. Shendure, M.D., Ph.D. in Patent Interference No. 105,857 (May 20, 2013).
United States Patent and Trademark Office Patent Trial and Appeal Board, 454 Notice of Submission of Record in Patent Interference No. 105,857 (Jun. 21, 2013).
United States Patent and Trademark Office Patent Trial and Appeal Board, 454 Opposition 3 (opposing JHU Motion 3 for judgment based on priority) in Patent Interference No. 105,857 (Apr. 26, 2013).
United States Patent and Trademark Office Patent Trial and Appeal Board, 454 Request for Oral Argument in Patent Interference No. 105,857 (Jun. 5, 2013).
United States Patent and Trademark Office Patent Trial and Appeal Board, Johns Hopkins Miscellaneous Motion No. 2 (requesting dismissal of non-compliant motion) in Patent Interference No. 105,857 (Mar. 7, 2013).
United States Patent and Trademark Office Patent Trial and Appeal Board, Johns Hopkins Opposition 3 in Patent Interference No. 105,857 (Apr. 26, 2013).

(56) References Cited

OTHER PUBLICATIONS

United States Patent and Trademark Office Patent Trial and Appeal Board, Johns Hopkins Reply 3 (for judgment based on priority) in Patent Interference No. 105,857 (Jun. 3, 2013).
Wahlberg et al. "Solid Phase Sequencing of PCR Products." *PCR 2: A Practical Approach*. McPherson et al., eds. New York: Oxford University Press. Chapter 5(1995):71-87.
"454 Life Sciences' Genome Sequencer 20(TM) Wins R&D 100 Award", Press Release, Roche, Aug. 31, 2006.
"454 Life Sciences Receives Gold Award from the Wall Street Journal in Global Technology Innovation Competition", Press Release, Roche, Oct. 25, 2005.
"2006 R & D 100 Award Winners", R & D Magazine, 12 pages.
"2006 R&D 100 Winner; Faster genome sequencing", Published on Research & Development (http://www.rdmag.com), Originally published in R&D Magazine, Sep. 2006.
"The 454 Genome Sequencer System Accelerates the Pace of Discovery in Diverse Fields of Biology", 250 Peer-Reviewed Publication Documents the Success of 454 Sequencing, Business Wire, Sep. 23, 2008, 3 pages.
"454 Life Sciences Named to 2006 Scientific American 50", Evaluate, Press Release, Nov. 20, 2006, 2 pages.
"454 Life Sciences—Genome Sequencer 20 System First to the Finish", Roche Diagnostics, 40 pages.
Assignment Recordation History, U.S. Pat. No. 8,748,102.
Andreasson H. et al. "Mitochondrial Sequence Analysis for Forensic Identification Using Pyrosequencing Technology", BioTechniques, vol. 32, No. 1 (2002), p. 124-133.
Atak, Z. et al. "High Accuracy Mutation Detection in Leukemia on a Selected Panel of Cancer Genes", PLoSONE, Jun. 2012, vol. 7, Issue 6, p. e38463.
Baker et al. "Male Mice Defective in the DNA Mismatch Repair Gene PMS2 Exhibit Abnormal Chromosome Synapsis in Meiosis", Cell, vol. 82, 309-319, 1995.
Bernard, P. et al. "Real-Time PCR Technology for Cancer Diagnostics", Clinical Chemistry 48:8, p. 1178-1185 (2002).
"Roche acquires 454 Life Sciences to strengthen presence in ultra-fast gene sequencing", F. Hoffmann-La Roche Ltd, Mar. 29, 2007, 4 pages.
Besaratinia, A. et al. "A high-throughput next-generation sequencing-based method for detecting the mutational fingerprint of carcinogens", Nucleic Acids Research, 2012, vol. 40, No. 15, p. e116.
"Breakthrough of the Year", Science (Special Section) www.sciencemag.org, vol. 322, 2008, p. 1768-1773.
Brenner S. et al. "In vitro cloning of complex mixtures of DNA on microbeads: Physical separation of differentially expressed cDNAs", PNAS, vol. 97, No. 4, 2000, p. 1665-1670.
Briggs, A. et al. "Patterns of damage in genomic DNA sequences from a Neandertal", PNAS, 2007, vol. 104, No. 37, p. 14616-14621.
Bubendorf, L. et al. "Survey of Gene Amplifications during Prostate Cancer Progression by High-Throughput Fluorescence in Situ Hybridization on Tissue Microarrays", Cancer Research 59, 803-806, Feb. 15, 1999.
Chang, H. et al. "Exome Sequencing Reveals Comprehensive Genomic Alterations Across Eight Cancer Cell Lines", PLoSONE, Jun. 2011, vol. 6, Issue 6, p. e21097.
Collins, F. et al. "Implications of the Human Genome Project for MedicalScience", Opportunities Medical Research, JAMA. 2001, vol. 285, p. 540-544.
Collins, F. et al. "New Goals for the U.S. Human Genome Project: 1998-2003", Science, 1998, vol. 282, p. 682-689.
Cox-Foster, D. et al. "A Metagenomic Survey of Microbes in Honey Bee Colony Collapse Disorder", Science, 2007, vol. 318, p. 283-287.
Curriculum Vitae—Paul H. Dear, 7 pages.
Dalloul, R. et al. "Multi-Platform Next-Generation Sequencing of the Domestic Turkey (*Meleagris gallopavo*): Genome Assembly and Analysis", PLoS Biology, 2010, vol. 8, Issue 9, p. e1000475.
Davies, K. "Roche Shuts Down Third-Generation NGS Research Programs", Bio IT World, Apr. 23, 2013, 2 pages.

Dear, P. "One by one: Single molecule tools for genomics", Briefings in Functional Genomics and Proteomics, 2003, vol. 1, No. 4, p. 397-416.
Dearlove A. "High throughput genotyping Technologies", Briefings in Functional Genomics and Proteomics, 2002, vol. 1, No. 2, p. 139-150.
Deggerdal et al. "Rapid Isolation of PCR-Ready DNA from Blood, Bone Marrow and Cultured Cells, Based on Paramagnetic Beads", BioTechniques 22:554-557 (1997).
Dressman, D. et al. "Transforming single DNA molecules into fluorescent magnetic particles for detection and enumeration of genetic variations", PNAS, 2003, vol. 100, No. 15, p. 8817-8822.
Dudley, D. et al. "Low-Cost Ultra-Wide Genotyping Using Roche/454 Pyrosequencing for Surveillance of HIV Drug Resistance", PLoSONE, 2012, vol. 7, Issue 5, p. e36494.
Elnifro, E. et al. "Multiplex PCR: Optimization and Application in Diagnostic Virology", Clinical Microbilogy Reviews, 2000, vol. 13, No. 4, p. 559-570.
Erlich. H.A. et al. "HLA DNA Typing and Transplantation", Immunity, vol. 14, 2001, p. 347-356.
Franca, L. et al. "A review of DNA sequencing techniques", Quarterly Reviews of Biophysics 35, 2 (2002), pp. 169-200.
Frangeul L. et al. "Cloning and assembly strategies in microbial genome projects", Microbiology (1999), 145, p. 2625-2634.
Gall, A. et al. "Universal Amplification, Next-Generation Sequencing, and Assembly of HIV-1 Genomes", Journal of Clinical Microbiology, Dec. 2012, vol. 50, No. 12, p. 3838-3844.
Germer S. "High-Throughput SNP Allele-Frequency Determination in Pooled DNA Samples by Kinetic PCR", Genome Research, 2000, 10:258-266.
Ghadessy, F. et al. "Directed evolution of polymerase function by compartmentalized self-replication", PNAS, 2001, vol. 98, No. 8, p. 4552-4557.
Gonzalez, M. et al. "Extremely high thermal stability of streptavidin and avidin upon biotin binding", Biomolecular Engineering 16 (1999) 67-72.
Green, R. et al. "Analysis of one million base pairs of Neanderthal DNA", Nature, vol. 444, 2006, p. 330-336.
Green P. "Against a Whole-Genome Shotgun", Genome Research, 7:410-417, 1997.
Ideker et al. "Anew Approach to Decoding Life: Systems Biology", Annu. Rev. Genomics Hum. Genet. 2001, 2:343-72.
ION Torrent, "Amplicon Sequencing", Life Technologies, 5 pages.
Katsura, S. et al. "Indirect micromanipulation of single molecules in water-in-oil emulsion", Electrophoresis, 2001, 22, p. 289-293.
Kobayashi I. et al. "Silicon Array of Elongated Through-Holes for Monodisperse Emulsion Droplets", AIChE Journal, 2002 vol. 48, No. 8, p. 1639-1644.
Kohsaka, H. et al. "Solid-Phase Polymerase Chain Reaction", Journal of Clinical Laboratory Analysis 8:452-455 (1994).
Lata, P. et al. "Flocculation of oil-in-water emulsions by detergents", Progr. Colloid & Polymer Sci., 1978, vol. 63, p. 65-67.
Lawrence et al. "Surface Effect and Structure of Single Crystal Wires", Chem. and Indust., 615 (1949), 1 page.
Leuders et al. "Archaeal Population Dynamics during Sequential Reduction Processes in Rice Field Soil", Applied and Environmental Microbiology, 2000, vol. 66, No. 7, p. 2732-2742.
Lien, S. et al. "Single-Sperm Typing", Current Protocols in Human Genetics (2002) 1.6.1-1.6.18, Supplement 32, 18 pages.
Lindqvist, C. et al. "Complete mitochondrial genome of a Pleistocene jawbone unveils the origin of polar bear", PNAS, 2010, vol. 107, No. 13, 14 pages.
Lizardi, P. et al. "Mutation detection and single-molecule counting using isothermal rolling-circle amplification", Nature Genetics, 1998, vol. 19, p. 225-232.
Luo, G. et al. "Rapid Identification of Pathogenic Fungi Directly from Cultures by Using Multiplex PCR", Journal of Clinical Microbiology, 2002, vol. 40, No. 8, p. 2860-2865.
Malovannaya, A. et al. Correction for "Streamlined analysis schema for high-throughput identification of endogenous protein complexes," Proc Natl Acad Sci USA, 2010, 107:2431-2436.
Mardis, E. "The impact of next-generation sequencing technology on genetics", Trends in Genetics vol. 24 No. 3, p. 133-141.

(56) References Cited

OTHER PUBLICATIONS

Margulies, M. et al. "Genome Sequencing in Open Microfabricated High Density Picoliter Reactors", Nature, 2005, vol. 437, No. 7057, p. 376-380.
Margulies, Reference Citations, Web of Science via Documents Delivered, Ex. 2013.
Mitra, R. et al. "In situ localized amplification and contact replication of many individual DNA molecules", Nucleic Acids Research, 1999, vol. 27, No. 24, e34, 6 pages.
Mullis, K. et al. "Specific Enzymatic Amplification of DNA in Vitro: The Polymerase Chain Reaction", Cold Spring Harbor Symposia on Quantitative Biology, vol. LI, 1986, p. 263-273.
Nallur, G. et al. "Signal amplification by rolling circle amplification on DNA microarrays", Nucleic Acids Research, 2001, vol. 29, No. 23, p. e118.
Nisisako, T. et al. "Formation of Droplets Using Branch Channels in a Microfluidic Circuit", SICE, Aug. 5-7, 2002, p. 957-959.
Nyren, Pal, "The History of Pyrosequencing", Methods in Molecular Biology, vol. 373, Pyrosequencing Protocols, 13 pages.
Oliphant, A. et al. "BeadArray Technology: Enabling an Accurate, Cost-Effective Approach to High-Throughput Genotyping", BioTechniques Jun. 2002, vol. 32, p. S56-S61.
IPR2016-00316 U.S. Pat. No. 8,748,102, Petitioners' Power of Attorney, Dec. 30, 2015, 4 pages.
IPR2016-00316 U.S. Pat. No. 8,748,102, Petition for Inter Partes Review of U.S. Pat. No. 8,748,102 Under 35 U.S.C. §§ 311-319 and 37 C.F.R. §§ 42.1-.80, 42.100-.123, Dec. 30, 2015, 64 pages.
IPR2016-00316, U.S. Pat. No. 8,748,102, Petitioners' Exhibit List Dec. 30, 2015, 10 pages.
IPR2016-00316, U.S. Pat. No. 8,748,102, Notice of Filing Date Accorded to Petition and Time for Filing Patent Owner Preliminary Response, Jan. 7, 2016, 5 pages.
IPR2016-00316, U.S. Pat. No. 8,748,102, Mandatory Notices, Jan. 19, 2016, 5 pages.
IPR2016-00316, U.S. Pat. No. 8,748,102, Motion for Ellen Scordino to Appear Pro Hac Vice on Behalf of 454 Life Sciences Corporation, Jan. 27, 2016, 6 pages.
IPR2016-00316, U.S. Pat. No. 8,748,102, Patent Owner'S Exhibit List, Jan. 27, 2016, 3 pages.
IPR2016-00316, U.S. Pat. No. 8,748,102, Motion for Susan Krumplitsch to Appear Pro Hac Vice on Behalf of 454 Life Sciences Corporation, Jan. 27, 2016, 6 pages.
IPR2016-00316, U.S. Pat. No. 8,748,102, Patent Owner'S Preliminary Response, Apr. 7, 2016, 57 pages.
IPR2016-00316, U.S. Pat. No. 8,748,102, Patent Owner'S Exhibit List, Apr. 7, 2016, 5 pages.
IPR2016-00316, U.S. Pat. No. 8,748,102, Decision, Institution of Inter Partes Review 37 C.F.R. § 42.108, Jul. 6, 2016, 43 pages.
IPR2016-00316 U.S. Pat. No. 8,748,102 B2; IPR2016-00319 U.S. Pat. No. 8,765,380 B2; IPR2016-00321 U.S. Pat. No. 7,323,305 B2; Scheduling Order, Jul. 6, 2016, 8 pages.
IPR2016-00316 U.S. Pat. No. 8,748,102, Thermo Fisher'S Objections to Evidence Under 37 C.F.R. § 42.64(b), Jul. 20, 2016, 22 pages.
IPR2016-00316 U.S. Pat. No. 8,748,102 B2; IPR2016-00319 U.S. Pat. No. 8,765,380 B2; IPR2016-00321 U.S. Pat. No. 7,323,305 B2; Decision Patent Owner's Motion for Pro Hac Vice Admission of Ellen Scordino 37 C.F.R. § 42.10(c), Sep. 7, 2016, 3 pages.
IPR2016-00316 U.S. Pat. No. 8,748,102 B2; IPR2016-00319 U.S. Pat. No. 8,765,380 B2; IPR2016-00321 U.S. Pat. No. 7,323,305 B2; Decision Patent Owner's Motion for Pro Hac Vice Admission of Susan Krumplitsch 37 C.F.R. § 42.10(c), Sep. 7, 2016, 3 pages.
IPR2016-00316 U.S. Pat. No. 8,748,102, Notice of Deposition of Paul H. Dear, D. Phil. 37 C.F.R. § 42.53(d), Sep. 9, 2016, 3 pages.
IPR2016-00316 U.S. Pat. No. 8,748,102, Patent Owner'S Response 37 C.F.R. § 42.107, dated Oct. 3, 2016, 82 pages.
IPR2016-00316 U.S. Pat. No. 8,748,102, Patent Owner'S Exhibit List, Oct. 3, 2016, 7 pages.
IPR2016-00316 U.S. Pat. No. 8,748,102, Thermo Fisher'S Objections to Evidence Under 37 C.F.R. § 42.64(b), Oct. 11, 2016, 21 pages.
IPR2016-00316 U.S. Pat. No. 8,748,102, Declaration of Christina K. Stock in Support of 454 Life Sciences Corporation's Response to Thermo Fisher's Objections to Evidence 37 C.F.R. § 42.64(b)(2), Oct. 25, 2016, 140 pages.
IPR2016-00316 U.S. Pat. No. 8,748,102 B2; IPR2016-00319 U.S. Pat. No. 8,765,380 B2; IPR2016-00321 U.S. Pat. No. 7,323,305 B2; Notice of Depostion of David I. Smith, Ph.D., Nov. 4, 2016, 3 pages.
IPR2016-00316 U.S. Pat. No. 8,748,102 B2, Declaration of David I. Smith, Ph.D. In Support of Patent Owner's Response, Oct. 3, 2016, 159 pages.
IPR2016-00316 U.S. Pat. No. 8,748,102 B2, Declaration of Kevin A. Marks, Esq. in support of Patent Owner's Response, Oct. 3, 2016, 43 pages.
IPR2016-00316 U.S. Pat. No. 8,748,102, Declaration of Christina K. Stock in Support of 454 Life Sciences Corporation's Response to Thermo Fisher's Objections to Evidence 37 C.F.R. § 42.64(b)(2), Aug. 10, 2016, 36 pages.
IPR2016-00316 U.S. Pat. No. 8,748,102, Declaration of Zachary Kerns in Support of 454 Life Sciences Corporation's Response to Thermo Fisher's Objections to Evidence 37 C.F.R. § 42.64(b)(2), Aug. 10, 2016, 364 pages.
IPR2016-00316 U.S. Pat. No. 8,748,102, Declaration of Paul H. Dear, D. Phil, Dec. 30, 2015, 212 pages.
IPR2016-00316 U.S. Pat. No. 8,748,102—Thermo Fisher Scientific Inc., Life Technologies Corp., and Ion Torrent Systems, Inc.'s Exhibit List, Jan. 3, 2017, 14 pages.
IPR2016-00316 U.S. Pat. No. 8,748,102—Thermo Fisher's Reply to Patent Owner's Response to the Petition, Jan. 3, 2017, 33 pages.
IPR2016-00316 U.S. Pat. No. 8,748,102—Patent Owner's Objections to Petitioner's Evidence, Jan. 10, 2017, 21 pages.
IPR2016-00316 U.S. Pat. No. 8,748,102—Notice of Deposition of Paul H. Dear, D. Phil, Jan. 23, 2017, 3 pages.
IPR2016-00316 U.S. Pat. No. 8,748,102—Patent Owner's Motion for Observations Regarding Cross-Examination Testimony of Petitioners' Reply Witnesses, Feb. 24, 2017, 5 pages.
IPR2016-00316 U.S. Pat. No. 8,748,102—Patent Owner's Exhibit List, Feb. 24, 2017, 7 pages.
IPR2016-00316 U.S. Pat. No. 8,748,102—Patent Owner's Request for Oral Argument, Feb. 24, 2017, 4 pages.
IPR2016-00316 U.S. Pat. No. 8,748,102—Patent Owner's Motion to Exclude, Feb. 24, 2017, 20 pages.
IPR2016-00316 U.S. Pat. No. 8,748,102—Petitioner's Request for Oral Argument, Feb. 24, 2017, 3 pages.
IPR2016-00316 U.S. Pat. No. 8,748,102—Petitioner's Motion to Exclude Evidence Under 37 C.F.R. § 42.64(c), Feb. 24, 2017, 17 pages.
IPR2016-00316 U.S. Pat. No. 8,748,102 B2; IPR2016-00319 U.S. Pat. No. 8,765,380 B2; IPR2016-00321 U.S. Pat. No. 7,323,305 B2—Order Trial Hearing, Mar. 8, 2017, 5 pages.
IPR2016-00316 U.S. Pat. No. 8,748,102—Patent Owner's Opposition to Petitioner's Motion to Exclude Evidence Under 37 C.F.R. § 42.64(c), Mar. 10, 2017, 11 pages.
IPR2016-00316 U.S. Pat. No. 8,748,102—Petitioner's Opposition to Patent Owner's Motion to Exclude Evidence, Mar. 10, 2017, 17 pages.
IPR2016-00316 U.S. Pat. No. 8,748,102—Petitioner's Response to Patent Owner's Motion for Observations on Cross-Examination of Petitioner's Reply Witnesses, Mar. 10, 2017, 5 pages.
IPR2016-00316 U.S. Pat. No. 8,748,102—Patent Owner's Reply to Petitioner's Opposition to Patent Owner's Motion to Exclude, Mar. 17, 2017, 8 pages.
IPR2016-00316 U.S. Pat. No. 8,748,102—Petitioner's Reply to Patent Owner's Opposition to Motion to Exclude Evidence, Mar. 17, 2017, 7 pages.
IPR2016-00316 U.S. Pat. No. 8,748,102—Petitioner's Updated Exhibit List, Mar. 21, 2017, 14 pages.
IPR2016-00316 U.S. Pat. No. 8,748,102—Petitioner's Transmittal Letter Accompanying Exhibit 1144, Mar. 21, 2017, 3 pages.

(56) References Cited

OTHER PUBLICATIONS

IPR2016-00316 U.S. Pat. No. 8,748,102 B2; IPR2016-00319 U.S. Pat. No. 8,765,380 B2; IPR2016-00321 U.S. Pat. No. 7,323,305 B2 Telephonic Hearing, Mar. 10, 2017, 7 pages.

IPR2016-00316 U.S. Pat. No. 8,748,102—Patent Owner's Exhibit List, Mar. 23, 2017, 7 pages.

IPR2016-00316 U.S. Pat. No. 8,748,102 B2; IPR2016-00319 U.S. Pat. No. 8,765,380 B2; IPR2016-00321 U.S. Pat. No. 7,323,305 B2—Order Conduct of the Proceedings—Potential Settlement and Rescheduling Oral Hearing 37 C.F.R. § 42.5, Mar. 29, 2017, 4 pages.

IPR2016-00316 U.S. Pat. No. 8,748,102—Joint Motion to Terminate Pursuant to 35 U.S.C.. § 317, Apr. 5, 2017, 5 pages.

IPR2016-00316 U.S. Pat. No. 8,748,102—Joint Request to Treat Settlement Agreement As Business Confidential Information, Apr. 5, 2017, 3 pages.

IPR2016-00316 U.S. Pat. No. 8,748,102—Petitioner's Updated Exhibit List, Apr. 5, 2017, 14 pages.

IPR2016-00316 U.S. Pat. No. 8,748,102—Second Declaration of Paul H. Dear, D. Phil, Jan. 2, 2017, 108 pages.

IPR2016-00316 U.S. Pat. No. 8,748,102—Declaration of Ivan T. Hofmann, CPA/CFF, CLP, Jan. 3, 2017, 42 pages.

IPR2016-00319 U.S. Pat. No. 8,765,380—Second Declaration of Paul H. Dear, D. Phil., Jan. 2, 2017, 97 pages.

IPR2016-00319 U.S. Pat. No. 8,765,380—Declaration of Ivan T. Hofmann, CPA/CFF, CLP, Jan. 3, 2017, 42 pages.

IPR2016-00316 U.S. Pat. No. 8,748,102 B2; IPR2016-00319 U.S. Pat. No. 8,765,380 B2; IPR2016-00321 U.S. Pat. No. 7,323,305 B2—Judgment Granting Joint Motion to Terminate Due to Settlement After Institution and Granting Request to Treat Agreements as Business Confidential Information 35 U.S.C. § 317 and 37 C.F.R. §§ 42.72, 42.74, Apr. 6, 2017, 4 pages.

IPR2016-00319 U.S. Pat. No. 8,765,380—Petitioners' Power of Attorney, Dec. 30, 2015, 4 pages.

IPR2016-00319 U.S. Pat. No. 8,765,380—Petition for Inter Partes Review of U.S. Pat. No. 8,765,380 Under 35 U.S.C. §§ 311-319 and 37 C.F.R. §§ 42.1-.80, 42.100-.123, Dec. 30, 2015, 62 pages.

IPR2016-00319 U.S. Pat. No. 8,765,380—Petitioners' Exhibit List, Dec. 30, 2015, 10 pages.

IPR2016-00319 U.S. Pat. No. 8,765,380—Notice of Filing Date Accorded to Petition and Time for Filing Patent Owner Preliminary Response, dated Jan. 7, 2016, 5 pages.

IPR2016-00319 U.S. Pat. No. 8,765,380—Mandatory Notices 37 C.F.R. § 42.8, Jan. 19, 2016, 5 pages.

IPR2016-00319 U.S. Pat. No. 8,765,380—Motion for Ellen Scordino to Appear Pro Hac Vice on Behalf of 454 Life Sciences Corporation, Jan. 27, 2016, 6 pages.

IPR2016-00319 U.S. Pat. No. 8,765,380—Patent Owner's Exhibit List, Jan. 27, 2016, 3 pages.

IPR2016-00319 U.S. Pat. No. 8,765,380—Motion for Susan Krumplitsch to Appear Pro Hac Vice on Behalf of 454 Life Sciences Corporation, Jan. 27, 2016, 6 pages.

IPR2016-00319 U.S. Pat. No. 8,765,380—Patent Owner's Preliminary Response 37 C.F.R. § 42.107, dated Apr. 7, 2016, 44 pages.

IPR2016-00319 U.S. Pat. No. 8,765,380—Patent Owner'S Exhibit List, Apr. 7, 2016, 6 pages.

IPR2016-00319 U.S. Pat. No. 8,765,380—Decision, Institution of Inter Partes Review 37 C.F.R. § 42.108, Jul. 6, 2016, 34 pages.

IPR2016-00319 U.S. Pat. No. 8,765,380—Thermo Fisher's Objections to Evidence Under 37 C.F.R. § 42.64(b), Jul. 20, 2016, 21 pages.

IPR2016-00319 U.S. Pat. No. 8,765,380—Notice of Deposition of Paul H. Dear, D. Phil. 37 C.F.R. § 42.53(d), Jan. 23, 2016, 3 pages.

IPR2016-00319 U.S. Pat. No. 8,765,380—Patent Owner's Response 37 C.F.R. § 42.107, dated Oct. 3, 2016, 73 pages.

IPR2016-00319 U.S. Pat. No. 8,765,380—Patent Owner's Exhibit List, Oct. 3, 2016, 7 pages.

IPR2016-00319 U.S. Pat. No. 8,765,380—Thermo Fisher's Objections to Evidence Under 37 C.F.R. § 42.64(b), Oct. 11, 2016, 21 pages.

IPR2016-00319 U.S. Pat. No. 8,765,380—Declaration of Christina K. Stock in Support of 454 Life Sciences Corporation's Response to Thermo Fisher's Objections to Evidence 37 C.F.R. § 42.64(b)(2), Oct. 25, 2016, 140 pages.

IPR2016-00319 U.S. Pat. No. 8,765,380—Thermo Fisher Scientific Inc., Life Technologies Corp., and Ion Torrent Systems, Inc.'s Exhibit List, Jan. 3, 2017, 14 pages.

IPR2016-00319 U.S. Pat. No. 8,765,380—Thermo Fisher's Reply to Patent Owner's Response to the Petition, Jan. 3, 2017, 31 pages.

IPR2016-00319 U.S. Pat. No. 8,765,380—Patent Owner's Objections to Petitioner's Evidence 37 C.F.R. § 42.64(b)(1), Jan. 10, 2017, 21 pages.

IPR2016-00319 U.S. Pat. No. 8,765,380—Declaration of Matthias Weiden, Jan. 3, 2017 and Declaration of Susanne Schmid, 155 pages.

IPR2016-00319 U.S. Pat. No. 8,765,380—Amended Notice of Deposition of Paul H. Dear, D. Phil. 37 C.F.R. § 42.53(d), Jan. 25, 2017, 3 pages.

IPR2016-00319 U.S. Pat. No. 8,765,380—Notice of Deposition of Ivan T. Hoffman 37 C.F.R. § 42.53(d), Jan. 25, 2017, 3 pages.

IPR2016-00319 U.S. Pat. No. 8,765,380—Patent Owner's Motion for Observations Regarding Cross-Examination Testimony of Petitioners' Reply Witnesses, Feb. 24, 2017, 5 pages.

IPR2016-00319 U.S. Pat. No. 8,765,380—Patent Owner's Exhibit List, Feb. 24, 2017, 7 pages.

IPR2016-00319 U.S. Pat. No. 8,765,380—Patent Owner's Request for Oral Argument 37 C.F.R. § 42.70, Feb. 24, 2017, 4 pages.

IPR2016-00319 U.S. Pat. No. 8,765,380—Petitioner's Request for Oral Argument, Feb. 24, 2017, 3 pages.

IPR2016-00319 U.S. Pat. No. 8,765,380—Petitioner's Motion to Exclude Evidence Under 37 C.F.R. § 42.64(c), Feb. 24, 2017, 17 pages.

IPR2016-00319 U.S. Pat. No. 8,765,380—Patent Owner's Motion to Exclude 37 C.F.R. § 42.64(c), Feb. 24, 2017, 20 pages.

IPR2016-00319 U.S. Pat. No. 8,765,380—Patent Owner's Opposition to Petitioner's Motion to Exclude Evidence Under 37 C.F.R. § 42.64(c), Mar. 10, 2017, 11 pages.

IPR2016-00319 U.S. Pat. No. 8,765,380—Petitioner's Opposition to Patent Owner's Motion to Exclude Evidence, Mar. 10, 2017, 17 pages.

IPR2016-00319 U.S. Pat. No. 8,765,380—Petitioner's Response to Patent Owner's Motion for Observations on Cross-Examination of Petitioner's Reply Witnesses, Mar. 10, 2017, 5 pages.

IPR2016-00319 U.S. Pat. No. 8,765,380—Patent Owner's Reply to Petitioner's Opposition to Patent Owner's Motion to Exclude, Mar. 17, 2017, 8 pages.

IPR2016-00319 U.S. Pat. No. 8,765,380—Petitioner's Reply to Patent Owner's Opposition to Motion to Exclude Evidence, Mar. 17, 2017, 7 pages.

IPR2016-00319 U.S. Pat. No. 8,765,380—Petitioner's Updated Exhibit List, Mar. 21, 2017, 14 pages.

IPR2016-00319 U.S. Pat. No. 8,765,380—Petitioner's Transmittal Letter Accompanying Exhibit 1144, Mar. 21, 2017, 3 pages.

IPR2016-00319 U.S. Pat. No. 8,765,380—Patent Owner's Exhibit List, Mar. 23, 2017, 7 pages.

IPR2016-00319 U.S. Pat. No. 8,765,380—Joint Motion to Terminate Pursuant to 35 U.S.C. § 317, Apr. 5, 2017, 5 pages.

IPR2016-00319 U.S. Pat. No. 8,765,380—Joint Request to Treat Settlement Agreement As Business Confidential Information, Apr. 5, 2017, 3 pages.

IPR2016-00319 U.S. Pat. No. 8,765,380—Petitioner's Updated Exhibit List, Apr. 5, 2017, 14 pages.

IPR2016-00321 U.S. Pat. No. 7,323,305—Second Declaration of Paul H. Dear, D. Phil., Jan. 2, 2017, 101 pages.

IPR2016-00321 U.S. Pat. No. 7,323,305—Declaration of Ivan T. Hofmann, CPA/CFF, CLP, Jan. 3, 2017, 42 pages.

IPR2016-00321 U.S. Pat. No. 7,323,305—Thermo Fisher Scientific Inc., Life Technologies Corp., and Ion Torrent Systems, Inc.'s Exhibit List, Jan. 3, 2017, 14 pages.

IPR2016-00321 U.S. Pat. No. 7,323,305—Thermo Fisher's Reply to Patent Owner's Response to the Petition, Jan. 3, 2017, 33 pages.

(56) References Cited

OTHER PUBLICATIONS

Pagratis N. "Rapid preparation of single stranded DNA from PCR products by streptavidin induced electrophoretic mobility shift", Nucleic Acids Research, 1996, vol. 24, No. 18 3645-3646.
Perez-Roth, E. et al. "Multiplex PCR for Simultaneous Identification of *Staphylococcus aureus* and Detection of Methicillin and Mupirocin Resistance", Journal of Clinical Microbiology, vol. 39, No. 11, 2001, p. 4037-4041.
Prochnik, S. et al. "The Cassava Genome: Current Progress, Future Directions", Tropical Plant Biol., 2012, vol. 5, p. 88-94.
Polz et al. "Bias in Template-to-Product Ratios in Multitemplate PCR", Applied and Environmental Microbiology, vol. 64, No. 10, 1998, p. 3724-3730.
Poon, A. et al. "Reconstructing the Dynamics of HIV Evolution within Hosts from Serial Deep Sequence Data", PLoS Computational Biology, 2012, vol. 8, Issue 11, p. e1002753.
Reinartz J. et al. "Massively parallel signature sequencing (MPSS) as a tool for in-depth quantitative gene expression profiling in all organisms", Briefing in functional Genomics and Proteomics, vol. 1, No. 1, p. 95-104, Feb. 2002.
Rogers, Y. et al. "Massively parallel sequencing", Nature, vol. 437, 2005, p. 326-327.
Ronaghi, M. "Pyrosequencing Sheds Light on DNA Sequencing", Genome Research, 2001, vol. 11, No. 3, p. 3-12.
Rosen, M. "Surfactants and Interfacial Phenomena", Second Edition, 1989, Chapter 8, 35 pages.
Rothberg, J. et al. "The development and impact of 454 sequencing", Nature Biotechnology, vol. 26, No. 10, 2008, p. 1117-1124.
Rothberg, Jonathan, LinkedIn, Founder, Chairman, CTO and CEO Ion Torrent by Life Technologies.
Saiki, R. et al. "Enzymatic Amplification of (3-Globin Genomic Sequences and Restriction Site Analysis for Diagnosis of Sickle Cell Anemia", Science, vol. 230, p. 1350-1354.
Sambrook, "Molecular Cloning" A Laboratory Manual, second edition, 1989, 20 pages.
Sanchez-Ferrer et al. "Phase Separation of Biomolecules in Polyoxyethylene Glycol Nonionic Detergents", Critical Reviews in Biochemistry and Molecular Biology, 29(4):275-313 (1994).
Schbath, S. et al. "The Effect of Nonhomogeneous Clone Length Distribution on the Progress of an STS Mapping Project", Journal of Computational Biology, vol. 7, Nos. 1/2, 2000, p. 47-57.
Schendure et al. "Next-generation DNA sequencing", Nature Biotechnology, vol. 26, No. 10, 2008, p. 1135-1145.
Schuster, S. et al. "Complete Khoisan and Bantu genomes from southern Africa", Letters, 2010, p. 943-947.
"Scientific American 50: Trends in Research, Business and Policy", Scientific American, 2006, vol. 50, 25 pages.
"Scientific American 50: SA 50 Winners and Contributors", Scientific American, 2006, vol. 50, 7 pages.
Sepp A. et al. "Microbead display by in vitro compartmentalisation: selection for binding using flow cytometry", FEBS Letters 532 (2002) 455-458.
Somodevilla-Torres, M. et al. "Solid-Phase Amplification and Detection: A Single-Tube Diagnostic Assay for Infectious Agents", Molecular Diagnosis vol. 6 No. 2, 2001, p. 131-136.
Spiro et al. "A Bead-Based Method for Multiplexed Identification and Quantitation of DNA Sequences Using Flow Cytometry", Applied and Environmental Microbiology, vol. 66, No. 10, 2000, p. 4258-4265.
Spiro et al. "Quantitation of DNA Sequences in Environmental PCR Products by a Multiplexed, Bead-Based Method", Applied and Environmental Microbiology, 2002, vol. 68, No. 2, p. 1010-1013.
Tawfik, D. et al. "Man-made cell-like compartments for Molecular evolution", Nature Biotechnology, vol. 16, 1998, p. 652-656.
Totty, Michael, "A Better Idea", The Wall Street Journal, Oct. 24, 2005, 10 pages.
Tucker, T. et al. "Massively Parallel Sequencing: The Next Big Thing in G.enetic Medicine", The American Journal of Human Genetics 85, 2009, p. 142-154.

Vet et al. "Multiplex detection of four pathogenic retroviruses using molecular beacons", Proc. Natl. Acad. Sci. USA vol. 96, pp. 6394-6399, 1999.
Vogelstein, B. et al. "Digital PCR", Proc. Natl. Acad. Sci. USA, vol. 96, pp. 9236-9241, 1999.
Wade, N. "DNA Machine May Advance Genetic Sequencing for Patients", Aug. 1, 2005, The New York Times, p. 46-47.
Wang F. et al. "Temperature Influence on the Secondary Structure of Avidin and Avidin-Biotin Complex: A Vibrational Circular Dichroism Study", J. Phys. Chem. B 2001, 105, p. 7857-7864.
Weissensteiner, T. et al, ed., "Current Innovations" PCR Technology, Second Edition, 2004, 19 pages.
Winzeler et al. "Functional Characterization of the *S. cerevisiae* Genome by Gene Deletion and Parallel Analysis", Science, vol. 285, 1999, p. 901-907.
World Economic Forum, Technology Pioneers 2007 brochure, 44 pages.
Zhang, J. et al. "The impact of next-generation sequencing on genomics", J Genet Genomics, 2011, vol. 38, No. 3, p. 95-109.
File History U.S. Pat. No. 8,765,380, (v.1).
File History U.S. Pat. No. 8,765,380, (v.2).
File History U.S. Pat. No. 8,765,380, (v.3).
File History U.S. Pat. No. 8,765,380, (v.4).
"See how GenR Scientists are using Roche Sequencing Solutions", 454 Life Sciences Home Page, 2015, 1 page.
IPR2016-00316 U.S. Pat. No. 8,748,102 B2—Declaration of Ellen Scordino in Support of PRO HAC VICE Motion, Jan. 27, 2016, 4 pages.
IPR2016-00316 U.S. Pat. No. 8,748,102—Declaration of Susan Krumplitsch in Support of Pro Hac Vice Motion, Jan. 27, 2016, 4 pages.
IPR2016-00316 U.S. Pat. No. 8,748,102 B2—Deposition of Paul H. Dear, Sep. 19, 2016 (rough draft), 31 pages.
IPR2016-00316 U.S. Pat. No. 8,748,102 B2; Declaration of Matthias Weiden and Declaration of Susanne Schmid, Jan. 3, 2017, 155 pages.
IPR2016-00316 U.S. Pat. No. 8,748,102 B2; Amended Notice of Deposition of Paul H. Dear, D. Phil., Jan. 25, 2017, 3 pages.
IPR2016-00316 U.S. Pat. No. 8,748,102 B2; Notice of Deposition of Ivan T. Hoffman, Jan. 25, 2017, 3 pages.
Heather et al. "The sequence of sequencers: The history of sequencing DNA", Genomics 107, 2016, p. 1-8.
J.P.Morgan, "Next Gen Sequencing Survey, What Laboratory Directors Are Saying About Next Generation Sequencing, GWAS and Stimulus", North America Equity Research, 2010, 57 pages.
Morozova et al. "Applications of next-generation sequencing technologies in functional genomics", Genomics, vol. 92, 2008, p. 255-264.
IPR2016-00319 U.S. Pat. No. 8,765,380 B2—Order re Claim Construction from Case 1:13-cv-01853-LPS, Aug. 24, 2015, 2 pages.
IPR2016-00319 U.S. Pat. No. 8,765,380 B2—Memorandum Opinion re Claim Construction from Case 1:13-cv-01853-LPS, Aug. 24, 2015, 18 pages.
Assignment Recordation History, U.S. Pat. No. 8,765,380.
File History U.S. Pat. No. 8,478,102.
Assignment Recordation History, U.S. Pat. No. 7,323,305.
IPR2016-00321 U.S. Pat. No. 7,323,305 B2—Petitioner's Power of Attorney, Dec. 30, 2015, 4 pages.
IPR2016-00321 U.S. Pat. No. 7,323,305 B2 Petition for Inter Partes Review of U.S. Pat. No. 7,323,305 Under 35 U.S.C. §§ 311-319 and 37 C.F.R. §§ 42.1-.80, 42.100-.123, Dec. 30, 2015, 63 pages.
IPR2016-00321 U.S. Pat. No. 7,323,305 B2—Petitioners' Exhibit List, Dec. 30, 2015, 10 pages.
IPR2016-00321 U.S. Pat. No. 7,323,305 B2—Notice of Filing Date Accorded to Petition and Time for Filing Patent Owner Preliminary Response, dated Dec. 30, 2015, 5 pages.
IPR2016-00321 U.S. Pat. No. 7,323,305 B2—Mandatory Notices, Jan. 19, 2016, 5 pages.
IPR2016-00321 U.S. Pat. No. 7,323,305 B2—Motion for Ellen Scordino to Appear Pro Hac Vice on Behalf of 454 Life Sciences Corporation, Jan. 27, 2016, 6 pages.

(56) References Cited

OTHER PUBLICATIONS

IPR2016-00321 U.S. Pat. No. 7,323,305 B2—Patent Owner's Exhibit List, Jan. 27, 2016, 3 pages.
IPR2016-00321 U.S. Pat. No. 7,323,305 B2—Motion for Susan Krumplitsch to Appear Pro Hac Vice on Behalf of 454 Life Sciences Corporation, Jan. 27, 2016, 6 pages.
IPR2016-00321 U.S. Pat. No. 7,323,305 B2—Patent Owner's Preliminary Response, dated Apr. 7, 2016, 51 pages.
IPR2016-00321 U.S. Pat. No. 7,323,305 B2—Patent Owner's Exhibit List, Apr. 7, 2016, 5 pages.
IPR2016-00321 U.S. Pat. No. 7,323,305 B2—Decision Institution of Inter Partes Review, Jul. 6, 2016, 40 pages.
IPR2016-00321 U.S. Pat. No. 7,323,305 B2—Patent Owner's Response, Oct. 3, 2016, 76 pages.
IPR2016-00321 U.S. Pat. No. 7,323,305 B2—Patent Owner's Exhibit List, Oct. 3, 2017, 5 pages.
IPR2016-00321 U.S. Pat. No. 7,323,305 B2—Thermo Fisher's Objections to Evidence Under 37 C.F.R. § 42.64(b), Jul. 20, 2016, 21 pages.
IPR2016-00321 U.S. Pat. No. 7,323,305 B2—Declaration of Christina K. Stock in Support of 454 Life Sciences Corporation's Response to Thermo Fisher's Objections to Evidence, Oct. 25, 2016, 140 pages.
IPR2016-00321 U.S. Pat. No. 7,323,305 B2—Thermo Fisher Scientific Inc., Life Technologies Corp., and Ion Torrent Systems, Inc.'s Exhibit List, Jan. 3, 2017, 14 pages.
IPR2016-00321 U.S. Pat. No. 7,323,305 B2—Patent Owner's Objections to Petitioner's Evidence, Jan. 10, 2017, 21 pages.
IPR2016-00321 U.S. Pat. No. 7,323,305 B2—Notice of Deposition of Paul H. Dear, D. Phil., Jan. 23, 2017, 3 pages.
IPR2016-00321 U.S. Pat. No. 7,323,305 B2—Declaration of Matthias Weiden and Declaration of Susanne Schmid, Jan. 25, 2017, 155 pages.
IPR2016-00321 U.S. Pat. No. 7,323,305 B2 Amended Notice of Deposition of Paul H. Dear, D. Phil., Jan. 25, 2017, 3 pages.
IPR2016-00321 U.S. Pat. No. 7,323,305 B2—Notice of Deposition of Ivan T. Hoffman, Jan. 25, 2017, 3 pages.
IPR2016-00321 U.S. Pat. No. 7,323,305 B2—Petitioner's Request for Oral Argument, Feb. 24, 2017, 3 pages.
IPR2016-00321 U.S. Pat. No. 7,323,305 B2—Petitioner's Motion to Exclude Evidence Under 37 C.F.R. § 42.64(c), Feb. 24, 2017, 17 pages.
IPR2016-00321 U.S. Pat. No. 7,323,305 B2—Patent Owner's Motion for Observations Regarding Cross-Examination Testimony of Petitioners' Reply Witnesses, Feb. 24, 2017, 5 pages.
IPR2016-00321 U.S. Pat. No. 7,323,305 B2—Patent Owner's Motion to Exclude, Feb. 24, 2017, 20 pages.
IPR2016-00321 U.S. Pat. No. 7,323,305 B2—Patent Owner's Request for Oral Argument, Feb. 24, 2017, 4 pages.
IPR2016-00321 U.S. Pat. No. 7,323,305 B2—Patent Owner's Opposition to Petitioner's Motion to Exclude Evidence Under 37 C.F.R. § 42.64(c), Mar. 10, 2017, 11 pages.
IPR2016-00321 U.S. Pat. No. 7,323,305 B2—Petitioner's Opposition to Patent Owner's Motion to Exclude Evidence, Mar. 10, 2017, 17 pages.
IPR2016-00321 U.S. Pat. No. 7,323,305 B2—Petitioner's Response to Patent Owner's Motion for Observations on Cross-Examination of Petitioner's Reply Witnesses, Mar. 10, 2017, 5 pages.
IPR2016-00321 U.S. Pat. No. 7,323,305 B2—Patent Owner's Reply to Petitioner's Opposition to Patent Owner's Motion to Exclude, Mar. 17, 2017, 8 pages.
IPR2016-00321 U.S. Pat. No. 7,323,305 B2—Petitioner's Reply to Patent Owner's Opposition to Motion to Exclude Evidence, Mar. 17, 2017, 7 pages.
IPR2016-00321 U.S. Pat. No. 7,323,305 B2—Petitioner's Transmittal Letter Accompanying Exhibit 1144, Mar. 21, 2017, 3 pages.
IPR2016-00316 U.S. Pat. No. 8,748,102; IPR2016-00319 U.S. Pat. No. 8,765,380; IPR2016-00321 U.S. Pat. No. 7,323,305 B2—Telephonic Hearing, Mar. 10, 2017, 7 pages.
IPR2016-00321 U.S. Pat. No. 7,323,305 B2—Patent Owner's Exhibit List, Mar. 23, 2017, 7 pages.
IPR2016-00321 U.S. Pat. No. 7,323,305 B2—Joint Motion to Terminate Pursuant to 35 U.S.C. § 317, Apr. 5, 2017, 5 pages.
IPR2016-00321 U.S. Pat. No. 7,323,305 B2—Joint Request to Treat Settlement Agreement As Business Confidential Information, Apr. 5, 2017 3 pages.
IPR2016-00321 U.S. Pat. No. 7,323,305 B2—Petitioner's Updated Exhibit List, Apr. 5, 2017, 14 pages.
IPR2016-00316 U.S. Pat. No. 8,748,102 B2; IPR2016-00319 U.S. Pat. No. 8,765,380 B2; IPR2016-00321 U.S. Pat. No. 7,323,305 B2—Patent Owner 454 Life Sciences Corporation's Oral Argument Demonstratives, Mar. 30, 2017, 56 pages.
U.S. Appl. No. 95/001,765 Patent Owner's Request for Rehearing of Patent Trial and Appeal Board's 37 C.F.R. §41.77(f) Decision, Aug. 21, 2017, 20 pages.
U.S. Appl. No. 95/001,765 37 C.F.R. § 41.77(f) Decision, Jul. 21, 2017, 21 pages.
U.S. Appl. No. 95/001,765 Third Party Requester's Notice of Abandonment of Appeal, Apr. 5, 2017, 3 pages.
U.S. Appl. No. 95/001,765 Patent Trial and Appeal Board Docketing Notice, Mar. 27, 2017, 3 pages.
U.S. Appl. No. 95/001,765 Patent Trial and Appeal Board Docketing Notice, Mar. 27, 2017, 5 pages.
U.S. Appl. No. 95/001,765 Transmittal of Communication to Third Party Requester Inter Partes Reexamination, Jan. 26, 2017, 4 pages.
U.S. Appl. No. 95/001,765 Exhibit A1, Dec. 19, 2015, 611 pages.
U.S. Appl. No. 95/001,765 Exhibit A2, Dec. 19, 2015, 530 pages.
U.S. Appl. No. 95/001,765 Exhibit A3, Dec. 19, 2015, 562 pages.
U.S. Appl. No. 95/001,765 Requester's Reply to Patent Owner's Comments on Examiner's Determination Under§ 41.77(d), Dec. 19, 2016, 9 pages.
U.S Appl. No. 95/001,765 Patent Owner's Comments Following Examiner's Determination Under 37 C.F.R. §41.77(d), Nov. 17, 2016, 21 pages.
U.S. Appl. No. 95/001,765 Inter Partes Reexamination; 41.77(d) Determination, Oct. 17, 2016, 9 pages.
U.S. Appl. No. 95/001,765 Order Remanding Inter Partes Reexamination Under 37 C.F.R. § 41.77(d) to the Examiner, Jun. 17, 2016, 7 pages.
U.S. Appl. No. 95/001,765 Requester's Comments on Patent Owner's Request to Reopen Prosecution, Jul. 29, 2015, 113 pages.
U.S. Appl. No. 95/001,765 Patent Owner's Request Under 37 C.F.R. §41.77(b)(1) to Reopen Prosecution Before the Examiner, Jun. 29, 2015, 23 pages.
U.S. Appl. No. 95/001,765—Decision on Appeal and Cross-Appeal, May 27, 2015, 44 pages.
U.S. Appl. No. 95/001,765 Oral Hearing Held: Mar. 18, 2015, Mailing date: Apr. 15, 2015, 52 pages.
U.S Appl. No. 95/001,765 Equipment request for Hearing, Mar. 11, 2015, 2 pages.
U.S. Appl. No. 95/001,765 Notice of Hearing Response Required Within 21 Days, Jan. 26, 2015, 4 pages.
U.S. Appl. No. 95/001,765 Notice of Hearing Response Required Within 21 Days, Jan. 26, 2015, 5 pages.
U.S. Appl. No. 95/001,765 Patent Owner's Request to Reschedule Hearing, Jan. 13, 2015, 4 pages.
U.S. Appl. No. 95/001,765 Decision on Request to Reschedule Oral Hearing, Jan. 21, 2015, 4 pages.
U.S. Appl. No. 95/001,765 Notice of Hearing Response Required Within 21 Days, Jan. 7, 2015, 4 pages.
U.S. Appl. No. 95/001,765 Patent Trial and Appeal Board Docketing Notice, Oct. 7, 2014, 2 pages.
Yang, X. et al. "Construction and selection of bead-bound combinatorial oligonucleoside phosphorothioate and phosphorodithioate aptamer libraries designed for rapid PCR-based sequencing", Nucleic Acids Research, 2002, vol. 30, No. 23 e132, 8 pages.
"Life sciences primer: Tools for a better tomorrow" Life Sciences and Diagnostic Tools, Bank of America Merrill Lynch, 2013, 84 pages.
"Next Generation Sequencing: Market Size, Segmentation, Growth and Trends by Provider", Decisive Bio-Insights, Next Generation Sequencing (NGS) Market, Mar. 2013, 2nd edition, 204 pages.

(56) References Cited

OTHER PUBLICATIONS

Applied Biosystems Inc. Form 10-K, Jun. 30, 2008, 73 pages.
Life Technologies Corporation Form 10-K, Dec. 31, 2010, 218 pages.
Roche Annual Report 2007, Finance Report, 127 pages.
CuraGen Corporation, Form 8-K, May 25, 2007, 5 pages.
License, Supply and Distribution Agreement between 454 Life Sciences Corporation and F. Hoffmann-La Roche Ltd., May 11, 2005, 64 pages.
"DNA Sequencing. What is DNA sequencing?", National Human Genome Research Institute, DNA Sequencing Fact Sheet, 2015, 4 pages.
Niedringhaus, T. et al. "Landscape of Next-Generation Sequencing Technologies", Anal Chem., 2011, vol. 83, No. 12, p. 4327-4341.
Von Bubnoff, "Next-Generation Sequencing: The Race Is on", Cell, 2008, vol. 132, p. 721-723.
Anderson M. et al. Next Generation DNA Sequencing and the Future of Genomic Medicine, Genes 2010, vol. 1, p. 38-69.
"Six Years After Acquisition, Roche Quietly Shutters 454", Bio-It World Staff, 2013, 1 page.
"Roche Shutting Down 454 Sequencing Business", genomeweb, 2013, 3 pages.
Curagen Corporation, Form 10-K, Dec. 31, 2006, 123 pages.
Thayer A. "Next-Gen Sequencing Is a Numbers Game", 2014, vol. 92, Issue 33, p. 11-15.
Coombs, "The sequencing shakeup", Nature Biotechnology, 2008, vol. 26, No. 10, p. 1109-1112.
Illumina, Inc. Form 10-K, Jan. 3, 2016, 133 pages.
History of Illumina Sequencing, 2016, 2 pages. http://www.illumina.com/technology/next-generation-sequencing/solexa-technology.html.
Dhiman N. "Next-generation sequencing: a transformative tool for vaccinology", Expert Rev. Vaccines 2009, vol. 8, No. 8, p. 963-967.
U.S. Pat. No. 7,323,305, File History, (v.1).
U.S. Pat. No. 7,323,305, File History, (v.2).
U.S. Pat. No. 7,323,305, File History, (v.3).
U.S. Pat. No. 7,323,305, File History, (v.4).
U.S. Pat. No. 7,323,305, File History, (v.5).
U.S. Pat. No. 7,323,305, File History, (v.6).
U.S. Pat. No. 7,323,305, File History, (v.7).
U.S. Pat. No. 7,323,305, File History, (v.8).
U.S. Pat. No. 7,323,305, File History, (v.9).
U.S. Pat. No. 7,323,305, File History, (v.10).
U.S. Pat. No. 7,323,305, File History, (v.11).
U.S. Pat. No. 7,323,305, File History, (v.12).
U.S. Pat. No. 7,323,305, File History, (v.13).
U.S. Pat. No. 7,323,305, File History, (v.14).
U.S. Appl. No. 95/001,765, Decision on Request for Rehearing, Feb. 13, 2018, 12 pages.
Ivan T. Ho mann, C.P.A., C.F.F., C.L.P., Curriculum Vitae, 1 page.
IPR2016-00316 U.S. Pat. No. 8,748,102—"Videotaped Deposition of David Smith, Ph.D.", Nov. 21, 2016, 165 pages.
IPR2016-00316 U.S. Pat. No. 8,748,102; IPR2016-00319 U.S. Pat. No. 8,765,380; IPR2016-00321 U.S. Pat. No. 7,323,305 B2—Patent Board Call, Nov. 21, 2016, 19 pages.
Susanne Schmid, Curriculum Vitae, 1 page.
IPR2016-00316 U.S. Pat. No. 8,748,102; IPR2016-00319 U.S. Pat. No. 8,765,380; IPR2016-00321 U.S. Pat. No. 7,323,305 B2—Deposition of Ivan T. Hoffmann, Feb. 3, 2017, 99 pages.
IPR2016-00316 U.S. Pat. No. 8,748,102; IPR2016-00319 U.S. Pat. No. 8,765,380; IPR2016-00321 U.S. Pat. No. 7,323,305 B2—Deposition of Paul H. Dear, D. Phil., Feb. 17, 2017, 101 pages.
IPR2016-00319 U.S. Pat. No. 8,765,380—Notice of Deposition of Paul H. Dear, D. Phil., Jan. 23, 2017, 3 pages.
IPR2016-00319 U.S. Pat. No. 8,765,380—Declaration of David I. Smith, Ph.D. In Support of Patent Owner's Response, Oct. 3, 2016, 140 pages.
IPR2016-00319 U.S. Pat. No. 8,765,380—Declaration of Kevin A. Marks, Esq. In Support of Patent Owners Response, Oct. 3, 2016, 43 pages.
IPR2016-00319 U.S. Pat. No. 8,765,380—Declaration of Christina K. Stock in Support of 454 Life Sciences Corporation's Response to Thermo Fisher's Objections to Evidence, Aug. 10, 2016, 36 pages.
IPR2016-00319 U.S. Pat. No. 8,765,380—Declaration of Zachary Kerns in Support of 454 Life Sciences Corporation's Response to Thermo Fisher's Objections to Evidence, Aug. 10, 2016, 364 pages.
IPR2016-00319 U.S. Pat. No. 8,765,380—Declaration of Ellen Scordino in Support of Pro Hac Vice Motion, Jan. 27, 2016, 4 pages.
IPR2016-00319 U.S. Pat. No. 8,765,380—Declaration of Susan Krumplitsch in Support of Pro Hac Vice Motion, Jan. 27, 2016, 4 pages.
IPR2016-00319 U.S. Pat. No. 8,765,380—Declaration of Paul H. Dear, D. Phil., Dec. 30, 2015, 169 pages.
IPR2016-00321 U.S. Pat. No. 7,323,305—Notice of Deposition of Paul H. Dear, D. Phil., Sep. 9, 2016, 3 pages.
IPR2016-0321 U.S. Pat. No. 7,323,305—Patent Owner's Exhibit List, Oct. 3, 2016, 5 pages.
IPR2016-0321 U.S. Pat. No. 7,323,305—Declaration of David I. Smith, Ph.D. In Support of Patent Owner's Response, Oct. 3, 2016, 146 pages.
IPR2016-0321 U.S. Pat. No. 7,323,305—Declaration of Kevin A. Marks, Esq. In Support of Patent Owner's Response, Oct. 3, 2016, 43 pages.
IPR2016-0321 U.S. Pat. No. 7,323,305—Declaration of Christina K. Stock in Support of 454 Life Sciences Corporation's Response to Thermo Fisher's Objections to Evidence, Aug. 2, 2016, 36 pages.
IPR2016-0321 U.S. Pat. No. 7,323,305—Declaration of Zachary Kerns in Support of 454 Life Sciences Corporation's Response to Thermo Fisher's Objections to Evidence, Aug. 10, 2016, 364 pages.
IPR2016-0321 U.S. Pat. No. 7,323,305—Declaration of Ellen Scordino in Support of Pro Hac Vice Motion, Jan. 27, 2016, 4 pages.
IPR2016-0321 U.S. Pat. No. 7,323,305—Declaration of Susan Krumplitsch in Support of Pro Hac Vice Motion, Jan. 27, 2016, 4 pages.
IPR2016-0321 U.S. Pat. No. 7,323,305—Declaration of Paul H. Dear, D. Phil., Dec. 30, 2015, 178 pages.
History of sequencing by synthesis. Evolution of Illumina Sequencing (2 pages).
U.S. Appl. No. 95/001,765, Notice of Intent to Issue Inter Partes Reexamination Certificate, mailing date Aug. 7, 2018, 6 pages.
U.S. Pat. No. 8,012,690, Inter Partes Reexamination Certificate, certificate issued Aug. 24, 2018, 2 pages.

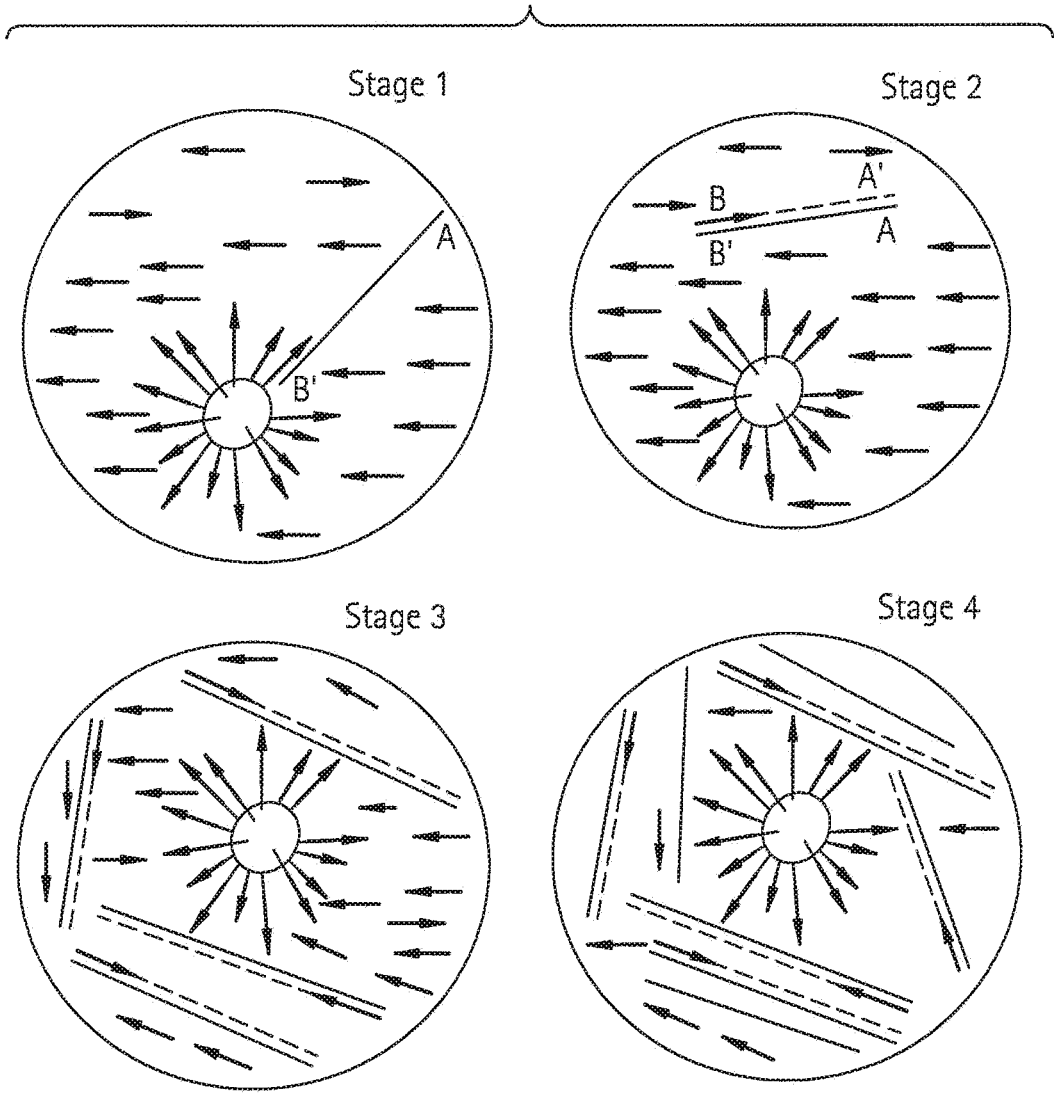

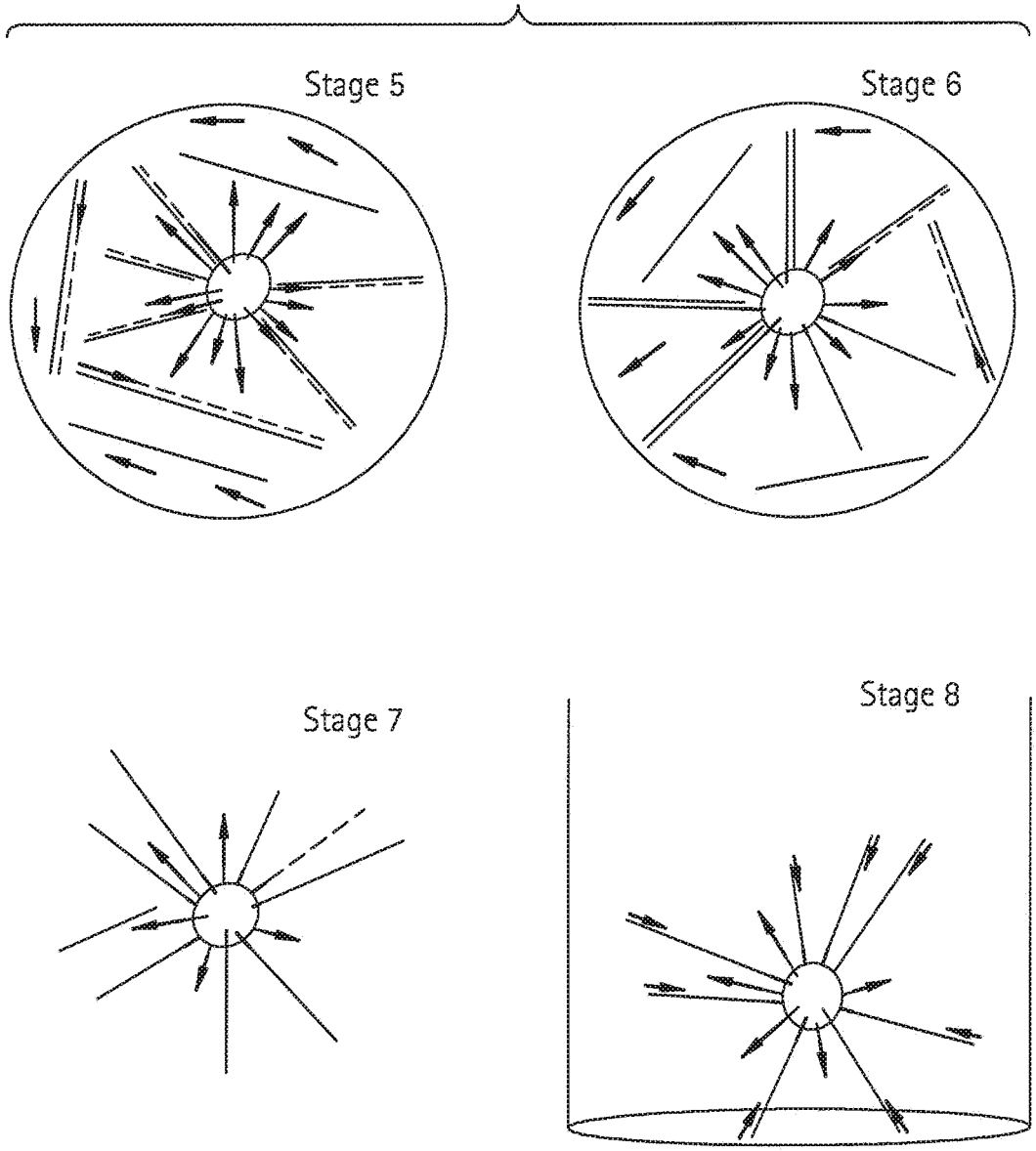

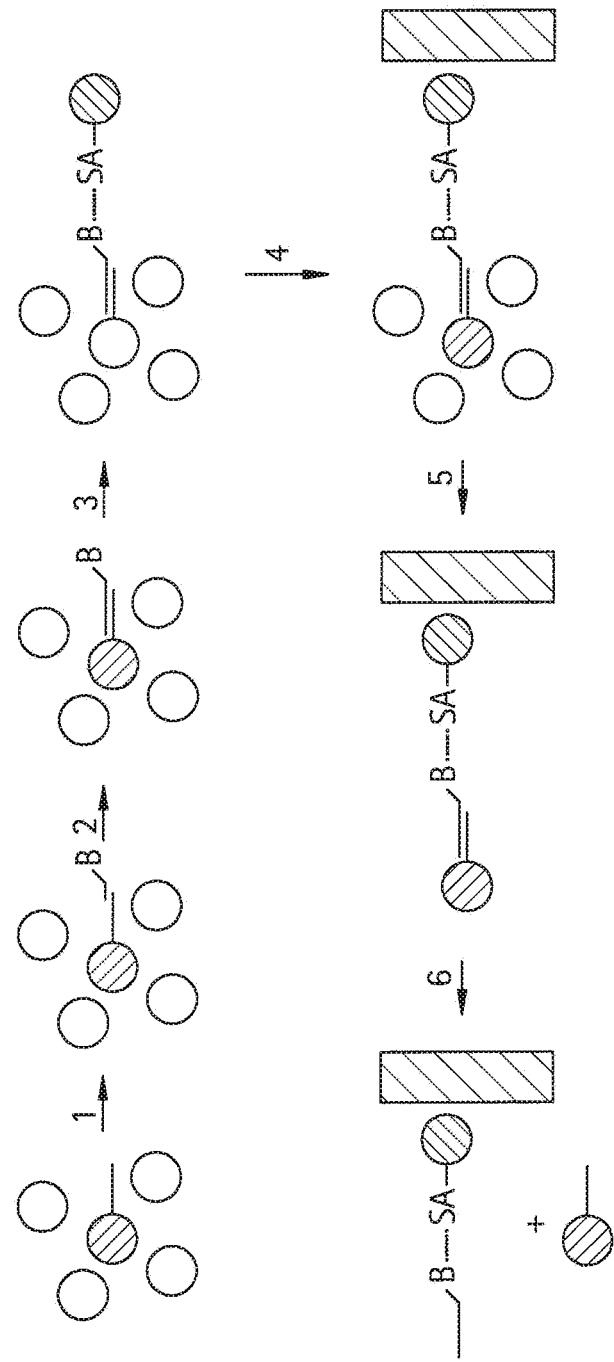

Emulsion breaking

2nd strand removal and enrichment

Annealing sequencing primers

1st segment sequencing

BEAD EMULSION NUCLEIC ACID AMPLIFICATION

RELATED APPLICATIONS

This application is a continuation of U.S. patent application Ser. No. 15/190,886, filed on Jun. 23, 2016, which is a continuation of U.S. patent application Ser. No. 14/518,700, filed on Oct. 20, 2014, which is a continuation of U.S. patent application Ser. No. 14/036,398, filed on Sep. 25, 2013, now abandoned, which is a continuation of U.S. patent application Ser. No. 13/618,334 (now U.S. Pat. No. 8,765,380), filed on Sep. 14, 2012, which is a continuation of U.S. patent application Ser. No. 13/033,240 (now U.S. Pat. No. 8,748,102), filed on Feb. 23, 2011, which is a continuation of U.S. patent application Ser. No. 11/982,095 (now U.S. Pat. No. 8,012,690), filed on Oct. 31, 2007, which is a continuation of U.S. patent application Ser. No. 10/767,899 (now U.S. Pat. No. 7,842,457), filed on Jan. 28, 2004, which claims the benefit of priority to the following applications: U.S. Patent Application No. 60/443,471 filed on Jan. 29, 2003, U.S. Patent Application No. 60/465,071 filed on Apr. 23, 2003, U.S. Patent Application No. 60/476,313 filed on Jun. 6, 2003, U.S. Patent Application No. 60/476,504 filed on Jun. 6, 2003, U.S. Patent Application No. 60/476,592 filed on Jun. 6, 2003, U.S. Patent Application No. 60/476,602 filed on Jun. 6, 2003, and U.S. Patent Application No. 60/497,985 filed on Aug. 25, 2003. All patent and patent applications in this paragraph are hereby fully incorporated herein by reference.

This application also incorporates by reference the following U.S. patent applications: "Method For Preparing Single-Stranded DNA Libraries" filed on Jan. 28, 2004, as U.S. patent application Ser. No. 10/767,894, now abandoned, "Double Ended Sequencing" filed on Jan. 28, 2004, as U.S. patent application Ser. No. 10/768,729, which issued as U.S. Pat. No. 7,244,567 on Jul. 17, 2007, and "Methods Of Amplifying And Sequencing Nucleic Acids" filed on Jan. 28, 2004 as U.S. patent application Ser. No. 10/767,779, which issued as U.S. Pat. No. 7,323,305 on Jan. 29, 2008.

INCORPORATION BY REFERENCE OF SEQUENCE LISTING

The contents of the text file named "454L_008C07U_Sequence_Listing.txt", which was created on Jan. 16, 2019 and is 6 KB in size, are hereby incorporated by reference in their entirety.

FIELD OF THE INVENTION

The present invention relates to methods for amplifying nucleic acid templates from low copy number to quantities amenable for sequencing on a solid support such as a bead. The present invention is also directed to zero bead removal—a method of enriching for solid support containing amplified nucleic acids is also disclosed.

BACKGROUND

The ability to amplify a plurality of nucleic acid sequences, such as a genomic library or a cDNA library, is critical given the inefficiency of current methods of sequencing. Current sequencing technologies require millions of copies of nucleic acid per sequencing reaction. Furthermore, the sequencing of a human genome would require about tens of millions of different sequencing reactions. If the starting material is limited, amplification of the initial DNA is necessary before genomic sequencing. The starting material may be limited, for example, if the genome to be sequenced is from a trace quantity of pathogen or from a prenatal patient. Current techniques for in vitro genome amplification involve laborious cloning and culturing protocols that have limited the utility of genomic sequencing. Other techniques, such as PCR, while fast and reliable, are unable to amplify a genome in a representative fashion.

While random primed PCR can be easily engineered to amplify a plurality of nucleic acids in one reaction, this method is not preferred because the amplified library is not representative of the starting library. That is, in a random PCR environment, some DNA sequences are preferentially amplified at the expense of other sequences such that the amplified product does not represent the starting material. This problem with PCR may be overcome if each individual member of a library is amplified in a separate reaction. However, this approach may be impractical if many thousands of separate reaction tubes are required for the amplification process, as a genomic library or cDNA library may include more than 100,000 fragments. Individual amplification of each fragment of these libraries in separate reaction is not practical.

SUMMARY OF THE INVENTION

The present invention provides for a method of amplifying a plurality of nucleic acids (e.g., each sequence of a DNA library, transcriptome, or genome) in a rapid and economical manner in a single reaction tube. One use of the method of the invention is to perform simultaneous clonal amplification (e.g., by PCR) of a plurality of samples (as many as several hundred thousand) in one reaction vessel. This invention further provides means for encapsulating a plurality of DNA samples individually in a microcapsule of an emulsion (i.e., a microreactor), performing amplification of the plurality of encapsulated nucleic acid samples simultaneously, and releasing said amplified plurality of DNA from the microcapsules for subsequent reactions.

In one embodiment, single copies of the nucleic acid template species are hybridized to capture beads comprising, e.g., capture oligonucleotides or chemical groups that bind to the nucleic acid template. The beads are suspended in complete amplification solution (see Example 2 for an example of an amplification solution) and emulsified to produce microreactors (typically 100 to 200 microns in diameter). After this, amplification (e.g., PCR) is used to clonally increase copy number of the initial template species in the microreactors, and these copies bind to the capture beads in the microreactors.

In an alternate embodiment, capture beads are added to an amplification reaction mixture (e.g., an amplification solution from Example 2) comprising nucleic acid template and this mixture is emulsified to produce microreactors. Amplification (e.g., PCR) is used to clonally increase copy number of the initial template species in the microreactors, and these copies bind to the capture beads in the microreactors.

One advantage of the present invention is that the microreactors allow the simultaneous clonal and discrete amplification of many different templates without cross contamination of the amplified products or reagents, or domination of one particular template or set of templates (e.g., PCR bias). The amplification reaction, for example, may be performed simultaneously with at least 3,000 microreactors per microliter of reaction mix. Preferably, each microreactor comprises one or fewer species of amplified template.

In various embodiments of the invention, the microreactors have an average size of about 10 μm to about 250 μm. In a preferred embodiment, the microreactors have an average diameter of about 60 to about 200 μm. In a more preferred embodiment, the microreactors have an average diameter of about 60 μm, such as an average of 40 μm to 80 μm in diameter. In an embodiment, the microreactors have an average diameter of about 60 μm. In another preferred embodiment, the microreactors have an average volume of about 113 pl. In a most preferred embodiment, about 3000 microreactors are contained within a microliter of a 1:2 water to oil emulsion.

The present invention also provides for a method for producing a plurality of nucleic acid template-carrying beads wherein each bead comprises up to and more than 1,000,000 copies of a single nucleic acid sequence. In one preferred embodiment, each bead may comprise over 20 million copies of a single nucleic acid.

The present invention further provides for a library made by the methods of the invention. The library may be made by using, e.g., a genomic DNA library, a cDNA library, or a plasmid library as the starting material for amplification. The library may be derived from any population of nucleic acids, e.g., biological or synthetic in origin.

The present invention also provides for a method of enriching for those beads that contains the product of successful DNA amplification (i.e., by removing beads that have no DNA attached thereto).

BRIEF DESCRIPTION OF THE DRAWINGS

FIGS. 2A-2B Schematics of one embodiment of a bead emulsion amplification process.

FIG. 3 Schematic of an enrichment process to remove beads that do not have any DNA attached thereto.

DETAILED DESCRIPTION OF INVENTION

Brief Overview of Bead Emulsion Amplification

Figure 1:
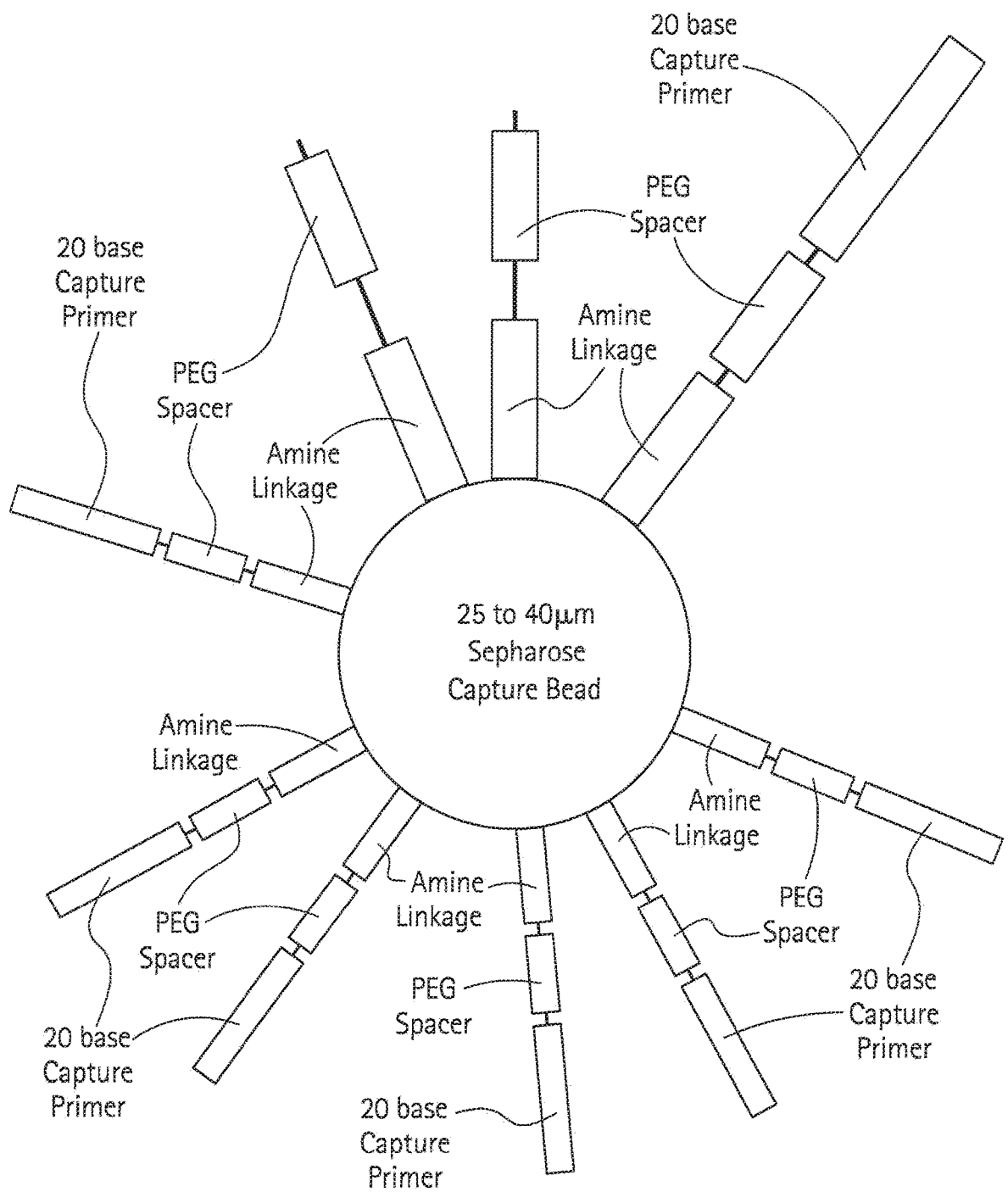
FIG. 1 Schematic of the structure of a DNA capture bead.

A brief overview of one embodiment of the invention is discussed below. A more detailed description of each individual step of this embodiment will follow. In this embodiment, PCR is the chosen amplification technique.

In one aspect of the invention, bead emulsion amplification is performed by attaching a template (e.g., DNA template) to be amplified to a solid support, preferably in the form of a generally spherical bead. The bead is linked to a large number of a single primer species (i.e., primer B in FIG. 2) that is complementary to a region of the template DNA and the amplification copies of this template. Alternately, the bead is linked to chemical groups (e.g., biotin) that can bind to chemical groups (e.g., streptavidin) included on the template DNA and amplification copies of this template. The beads are suspended in aqueous reaction mixture and then encapsulated in a water-in-oil emulsion. In different aspects of the invention, the template DNA is bound to the bead prior to emulsification, or the template DNA is included in solution in the amplification reaction mixture. In a preferred embodiment, an amplification step is performed prior to distribution of the nucleic acid templates onto a multiwell (e.g., picotiter) plate.

In certain embodiments, the emulsion is composed of discrete aqueous phase microdroplets, e.g., averaging approximately 60 to 200 μm in diameter, enclosed by a thermostable oil phase. Each microdroplet contains, preferably, amplification reaction solution (i.e., the reagents necessary for nucleic acid amplification). An example of an amplification reaction solution would be a PCR reaction mixture (polymerase, salts, dNTPs; see Example 2 for an example of one embodiment) and a pair of PCR primers (primer A and primer B). See, FIG. 2A. In some cases, the template DNA is included in the reaction mixture. A subset of the microdroplet population includes the DNA bead and the template. This subset of microdroplet is the basis for the amplification. The remaining microcapsules do not contain template DNA and will not participate in amplification. In one embodiment, the amplification technique is PCR and the PCR primers are present in an 8:1 or 16:1 ratio (i.e., 8 or 16 of one primer to 1 of the second primer) to perform asymmetric PCR. In another embodiment, the ratio of PCR primers may be substantially equal for normal PCR.

The amplification reaction, such as PCR, may be performed using any suitable method. In the following overview, one mechanism of PCR is discussed as an illustration. However, it is understood that the invention is not limited to this mechanism. In the example, a region of the DNA molecule (B' region) is annealed to an oligonucleotide immobilized to a bead (primer B). During thermocycling (FIG. 2B), the bond between the single stranded template and the immobilized B primer on the bead is broken, releasing the template into the surrounding microencapsulated solution. The amplification solution, in this case, the PCR solution, contains addition solution phase primer A and primer B (e.g., in a 8:1 or 16:1 ratio). Solution phase B primers readily bind to the complementary B' region of the template as binding kinetics are more rapid for solution phase primers than for immobilized primers.

In early phase PCR, both A and B strands amplify equally well (FIG. 2C). By midphase PCR (i.e., between cycles 10 and 30) the B primers are depleted, halting exponential amplification. The reaction then enters asymmetric amplification and the amplicon population becomes dominated by A strands (FIG. 2D). In late phase PCR (FIG. 2E), after 30 to 40 cycles, asymmetric amplification increases the concentration of A strands in solution. Excess A strands begin to anneal to bead immobilized B primers. Thermostable polymerases then utilize the A strand as a template to synthesize an immobilized, bead bound B strand of the amplicon.

In final phase PCR (FIG. 2F), continued thermal cycling forces additional annealing to bead bound primers. Solution phase amplification may be minimal at this stage but concentration of immobilized B strands increase. Then, the emulsion is broken and the immobilized product is rendered single stranded by denaturing (by heat, pH etc.) which removes the complimentary A strand. The A primers are annealed to the A' region of immobilized strand, and immobilized strand is loaded with sequencing enzymes, and any necessary accessory proteins. The beads are then sequenced using recognized pyrophosphate techniques (described, e.g., in U.S. Pat. Nos. 6,274,320, 6,258,568 and 6,210,891, incorporated in toto herein by reference).

Template Design

In a preferred embodiment, the nucleic acid template to be amplified by bead emulsion amplification is a population of DNA such as, for example, a genomic DNA library or a cDNA library. It is preferred that each member of the DNA population have a common nucleic acid sequence at the first end and a common nucleic acid sequence at a second end. This can be accomplished, for example, by ligating a first adaptor DNA sequence to one end and a second adaptor DNA sequence to a second end of each member of the DNA population. Many DNA and cDNA libraries, by nature of the cloning vector (e.g., Bluescript, Stratagene, La Jolla, Calif.) fit this description of having a common sequence at a first end and a second common sequence at a second end of each member DNA. The nucleic acid template may be of any size amenable to in vitro amplification (including the preferred amplification techniques of PCR and asymmetric PCR). In a preferred embodiment, the template is about 150 to 750 bp in size, such as, for example about 250 bp in size.

Binding Nucleic Acid Template to Capture Beads

In one aspect of the invention, a single stranded nucleic acid template to be amplified is attached to a capture bead. The template may be captured to the bead prior to emulsification or after the emulsion has been formed. In a preferred aspect, the amplification copies of the nucleic acid template are attached to a capture bead. As non-limiting examples, these attachments may be mediated by chemical groups or oligonucleotides that are bound to the surface of the bead. The nucleic acid (e.g., the nucleic acid template, amplification copies, or oligonucleotides) may be attached to the solid support (e.g., a capture bead) in any manner known in the art.

According to the present invention, covalent chemical attachment of a nucleic acid to the bead can be accomplished by using standard coupling agents. For example, water-soluble carbodiimide can be used to link the 5'-phosphate of a DNA sequence to amine-coated capture beads through a phosphoamidate bond. Alternatively, specific oligonucleotides can be coupled to the bead using similar chemistry, and to then DNA ligase can be used to ligate the DNA template to the oligonucleotide on the bead. Other linkage chemistries to join the oligonucleotide to the beads include the use of N-hydroxysuccinamide (NHS) and its derivatives.

In an exemplary method, one end of a linker may contain a reactive group (such as an amide group) which forms a covalent bond with the solid support, while the other end of the linker contains a second reactive group that can bond with the oligonucleotide to be immobilized. In a preferred embodiment, the oligonucleotide is bound to the DNA capture bead by covalent linkage. However, non-covalent linkages, such as chelation or antigen-antibody complexes, may also be used to join the oligonucleotide to the bead.

As non-limiting examples, oligonucleotides can be employed which specifically hybridize to unique sequences at the end of the DNA fragment, such as the overlapping end from a restriction enzyme site or the "sticky ends" of cloning vectors, but blunt-end linkers can also be used. These methods are described in detail in U.S. Pat. No. 5,674,743. It is preferred that the beads will continue to bind the immobilized oligonucleotide throughout the steps in the methods of the invention.

In one embodiment of the invention, each capture bead is designed to have a plurality of oligonucleotides that recognize (i.e., are complementary to) a portion of the nucleic template, and the amplification copies of this template. In the methods described herein, clonal amplification of the template species is desired, so it is preferred that only one unique nucleic acid species is attached to any one capture bead.

The beads used herein may be of any convenient size and fabricated from any number of known materials. Example of such materials include: inorganics, natural polymers, and synthetic polymers. Specific examples of these materials include: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and other solid phase supports known to those of skill in the art. In preferred embodiments, the capture beads are beads approximately 2 to 100 μm in diameter, or 10 to 80 μm in diameter, most preferably 20 to 40 μm in diameter. In a preferred embodiment, the capture beads are Sepharose beads.

Emulsification

For use with the present invention, capture beads with or without attached nucleic acid template are suspended in a heat stable water-in-oil emulsion. It is contemplated that a plurality of the microreactors includes only one template and one bead. There may be many droplets that do not contain a template or which do not contain a bead. Likewise there may be droplets that contain more than one copy of a template. The emulsion may be formed according to any suitable method known in the art. One method of creating emulsion is described below but any method for making an emulsion may be used. These methods are known in the art and include adjuvant methods, counter-flow methods, cross-current methods, rotating drum methods, and membrane methods. Furthermore, the size of the microcapsules may be adjusted by varying the flow rate and speed of the components. For example, in dropwise addition, the size of the drops and the total time of delivery may be varied. Preferably, the emulsion contains a density of about 3,000 beads encapsulated per microliter.

Various emulsions that are suitable for biologic reactions are referred to in Griffiths and Tawfik, EMBO, 22, pp. 24-35 (2003); Ghadessy et al., Proc. Natl. Acad. Sci. USA 98, pp. 4552-4557 (2001); U.S. Pat. No. 6,489,103 and WO 02/22869, each fully incorporated herein by reference. It is noted that Griffiths et al., (U.S. Pat. No. 6,489,103 and WO 99/02671) refers to a method for in vitro sorting of one or more genetic elements encoding a gene products having a desired activity. This method involves compartmentalizing a gene, expressing the gene, and sorting the compartmentalized gene based on the expressed product. In contrast to the present invention, the microencapsulated sorting method of Griffith is not suitable for parallel analysis of multiple microcapsules because their nucleic acid product is not anchored and cannot be anchored. Since the nucleic acids of Griffiths are not anchored, they would be mixed together during demulsification.

The emulsion is preferably generated by adding beads to an amplification solution. As used herein, the term "amplification solution" means the sufficient mixture of reagents that is necessary to perform amplification of template DNA. One example of an amplification solution, a PCR amplification solution, is provided in the Examples below. It will be appreciated that various modifications may be made to the amplification solution based on the type of amplification being performed and whether the template DNA is attached to the beads or provided in solution. In one embodiment, the mixture of beads and amplification solution is added dropwise into a spinning mixture of biocompatible oil (e.g., light mineral oil, Sigma) and allowed to emulsify. In another embodiment, the beads and amplification solution are added dropwise into a cross-flow of biocompatible oil. The oil used may be supplemented with one or more biocompatible emulsion stabilizers. These emulsion stabilizers may include Atlox 4912, Span 80, and other recognized and commercially available suitable stabilizers. In preferred aspects, the emulsion is heat stable to allow thermal cycling, e.g., to at least 94° C., at least 95° C., or at least 96° C. Preferably, the droplets formed range in size from about 5 microns to about 500 microns, more preferably from about 10 microns to about 350 microns, even more preferably from about 50 to 250 microns, and most preferably from about 100 microns to about 200 microns. Advantageously, cross-flow fluid mixing allows for control of the droplet formation, and uniformity of droplet size. We note that smaller water droplets not containing beads may be present in the emulsion.

The microreactors should be sufficiently large to encompass sufficient amplification reagents for the degree of amplification required. However, the microreactors should be sufficiently small so that a population of microreactors, each containing a member of a DNA library, can be amplified by conventional laboratory equipment, e.g., PCR thermocycling equipment, test tubes, incubators and the like. Notably, the use of microreactors allows amplification of complex mixtures of templates (e.g., genomic DNA samples or whole cell RNA) without intermixing of sequences, or domination by one or more templates (e.g., PCR selection bias; see, Wagner et al., 1994, Suzuki and Giovannoni, 1996; Chandler et al., 1997, Polz and Cavanaugh, 1998).

With the limitations described above, the optimal size of a microreactor may be on average 100 to 200 microns in diameter. Microreactors of this size would allow amplification of a DNA library comprising about 600,000 members in a suspension of microreactors of less than 10 ml in volume. For example, if PCR is the chosen amplification method, 10 ml of microreactors would fit into 96 tubes of a regular thermocycler with 96 tube capacity. In a preferred embodiment, the suspension of 600,000 microreactors would have a volume of less than 1 ml. A suspension of less than 1 ml may be amplified in about 10 tubes of a conventional PCR thermocycler. In a most preferred embodiment, the suspension of 600,000 microreactors would have a volume of less than 0.5 ml.

Another embodiment of the invention is directed to a method of performing nucleic acid amplification with a template and a bead, but without attachment of the template to the bead. In one aspect, the bead may comprise a linker molecule that can bind the amplified nucleic acid after amplification. For example, the linker may be a linker that can be activated. Such linkers are well known and include temperature sensitive or salt sensitive binding pairs such as streptavidin/biotin and antibodies/antigen. The template nucleic acid may be encapsulated with a bead and amplified. Following amplification, the amplified nucleic acid may be linked to the beads, e.g., by adjustments in temperature or salt concentration.

Amplification

After encapsulation, the template nucleic acid may be amplified, while attached or unattached to beads, by any suitable method of amplification including transcription-based amplification systems (Kwoh D. et al., Proc. Natl. Acad Sci. (U.S.A.) 86:1173 (1989); Gingeras T. R. et al., WO 88/10315; Davey, C. et al., EP Publication No. 329,822; Miller, H. I. et al., WO 89/06700), "RACE" (Frohman, M. A., In: PCR Protocols: A Guide to Methods and Applications, Academic Press, NY (1990)) and one-sided PCR (Ohara, O. et al., Proc. Natl. Acad. Sci. (U.S.A.) 86.5673-5677 (1989)). Still other methods such as di-oligonucleotide amplification, isothermal amplification (Walker, G. T. et al., Proc. Natl. Acad. Sci. (U.S.A.) 89:392-396 (1992)), Nucleic Acid Sequence Based Amplification (NASBA; see, e.g., Deiman B et al., 2002, Mol Biotechnol. 20(2):163-79), whole-genome amplification (see, e.g., Hawkins T L et al., 2002, Curr Opin Biotechnol. 13(1):65-7), strand-displacement amplification (see, e.g., Andras S C, 2001, Mol Biotechnol. 19(1):29-44), rolling circle amplification (reviewed in U.S. Pat. No. 5,714,320), and other well known techniques may be used in accordance with the present invention.

In a preferred embodiment, DNA amplification is performed by PCR. PCR according to the present invention may be performed by encapsulating the target nucleic acid with a PCR solution comprising all the necessary reagents for PCR. Then, PCR may be accomplished by exposing the emulsion to any suitable thermocycling regimen known in the art. In a preferred embodiment, 30 to 50 cycles, preferably about 40 cycles, of amplification are performed. It is desirable, but not necessary, that following the amplification procedure there be one or more hybridization and extension cycles following the cycles of amplification. In a preferred embodiment, 10 to 30 cycles, preferably about 25 cycles, of hybridization and extension are performed (e.g., as described in the examples). Routinely, the template DNA is amplified until typically at least 10,000 to 50,000,000 copies are immobilized on each bead. It is recognized that for nucleic acid detection applications, fewer copies of template are required. For nucleic acid sequencing applications we prefer that at least two million to fifty million copies, preferably about ten million to thirty million copies of the template DNA are immobilized on each bead. The skilled artisan will recognize that the size of bead (and capture site thereon) determines how many captive primers can be bound (and thus how many amplified templates may be captured onto each bead).

PCR Primer Design

The selection of nucleic acid primers for amplification, such as PCR amplification, is well within the abilities of one of skill in the art. Strategies for primer design may be found throughout the scientific literature, for example, in Rubin, E. and A. A. Levy, Nucleic Acids Res, 1996. 24(18): p. 3538-45; and Buck, G. A., et al., Biotechniques, 1999. 27(3): p. 528-36. In a preferred embodiment, primers can be limited to a length of 20 bases (5 tetramers) for efficient synthesis of bipartite PCR/sequencing primers. Each primer can include a two-base GC clamp on the 5' end, a single GC clamp on the 3' end, and all primers can share similar $T_m$ (+/−2° C.). In a preferred embodiment, hairpin structures within the primers (internal hairpin stems $\Delta G > -1.9$ kcal/mol) are strongly discouraged in any of the designed primers. In another preferred embodiment, primer dimerization is also controlled; such that a 3-base maximum acceptable dimer is allowed. However, this is allowed to occur only in the final six 3' bases, and the maximum allowable $\Delta G$ for a 3' dimer is −2.0 kcal/mol. Preferably, a penalty is applied to primers in which the 3' ends are too similar to others in the group. This prevents cross-hybridization between one primer and the reverse complement of another primer.

If the primers are designed according to the criteria described above, the possibility of complimentary regions occurring within the genome of interest is not of major concern, despite the reported tolerance of PCR to mismatches in complex sample populations (Rubin, E. and A. A. Levy. Nucleic Acids Res, 1996. 24(18): p. 3538-45). Although the probability of finding a perfect match to a 20 base primer is extremely low ($4^{20}$) (see Table 1), the probability of finding shorter non-consecutive matches increases significantly with the size of the genome of interest. As a result, the probability of finding a perfect match for a sequence of at least 10 of 20 bases is 99.35% for an Adenovirus genome. The probability of finding a perfect match for a sequence of 16 bases is 97% for the sequences in the NCBI database (approximately 100 times more sequence information than the Adenovirus genome). The probability of finding a perfect match for a sequence of 17 to 20 bases is 99% for the human genome (approximately 3 billion bases).

TABLE 1

The probability of perfect sequence matches for primers increases with decreasing match length requirements and increasing size of the genome of interest.

| Match Length | Perfect match probability (1/(4^length)) | % chance for match in Adeno ~35K bases | % chance for match in NCBI bacterial database ~488M bases | % chance for match in Human ~3B bases |
| --- | --- | --- | --- | --- |
| 20 | 9.1E−13 | 0.00% | 0.04% | 0.27% |
| 19 | 7.3E−12 | 0.00% | 0.65% | 4.32% |
| 18 | 4.4E−11 | 0.00% | 5.76% | 34.37% |
| 17 | 2.3E−10 | 0.00% | 35.69% | 99.17% |
| 16 | 1.2E−09 | 0.02% | 97.52% | >100% |
| 15 | 5.6E−09 | 0.12% | >100% | >100% |
| 14 | 2.6E−08 | 0.64% | >100% | >100% |
| 13 | 1.2E−07 | 3.29% | >100% | >100% |
| 12 | 5.4E−07 | 15.68% | >100% | >100% |
| 11 | 2.4E−06 | 58.16% | >100% | >100% |
| 10 | 1.0E−05 | 99.35% | >100% | >100% |
| 9 | 4.6E−05 | 99.77% | >100% | >100% |
| 8 | 2.0E−04 | >100% | >100% | >100% |
| 7 | 8.5E−04 | >100% | >100% | >100% |
| 6 | 3.7E−03 | >100% | >100% | >100% |
| 5 | 1.6E−02 | >100% | >100% | >100% |
| 4 | 6.4E−02 | >100% | >100% | >100% |
| 3 | 2.5E−01 | >100% | >100% | >100% |
| 2 | 7.1E−01 | >100% | >100% | >100% |
| 1 | 1.0E+00 | >100% | >100% | >100% |

However, primer cross-hybridization to various regions of the genome is less problematic than one might expect due to the random DNA digestion used to form the nucleic acid templates. The cross-hybridizing regions (CHRs) are fairly benign. First, it is unlikely that a CHR would be able to successfully compete with the perfect match between the PCR primers in solution and the template. In addition, any primers that include mismatches at their 3' end will be at a significant competitive disadvantage. Even if a CHR should out compete the intended PCR primer, it would produce a truncated PCR product, without a downstream site for the sequencing primer. If the truncated product could be driven to the capture bead and immobilized, one of two situations would result. If the CHR out-competed the solution-phase primer, then the immobilized product would lack a sequencing primer binding site, and would result in an empty picotiter plate (PTP) well. If the CHR out-competed the bead-bound primer, the sequencing primer would still be present, and the only effect would be a shorter insert. Neither result would unduly compromise the sequencing quality. Given the large amount of genomic material used in the sample preparation process (currently 25 μg, containing $5.29 \times 10^{16}$ copies of the 35 Kb Adenovirus genome), over-sampling can be used to provide fragments that lack the complete CHR, and allow standard PCR amplification of the region in question.

Breaking the Emulsion and Bead Recovery

Following amplification of the nucleic acid template and the attachment of amplification copies to the bead, the emulsion is "broken" (also referred to as "demulsification" in the art). There are many methods of breaking an emulsion (see, e.g., U.S. Pat. No. 5,989,892 and references cited therein) and one of skill in the art would be able to select an appropriate method. In the present invention, one preferred method of breaking the emulsion uses additional oil to cause the emulsion to separate into two phases. The oil phase is then removed, and a suitable organic solvent (e.g., hexanes) is added. After mixing, the oil/organic solvent phase is removed. This step may be repeated several times. Finally, the aqueous layers above the beads are removed. The beads are then washed with a mixture of an organic solvent and annealing buffer (e.g., one suitable annealing buffer is described in the examples), and then washed again in annealing buffer. Suitable organic solvents include alcohols such as methanol, ethanol, and the like.

The beads bound to amplification products may then be resuspended in aqueous solution for use, for example, in a sequencing reaction according to known technologies. (See, Sanger, F. et al., Proc. Natl. Acad. Sci. U.S.A. 75, 5463-5467 (1977); Maxam, A. M. & Gilbert, W. Proc Natl Acad Sci USA 74, 560-564 (1977); Ronaghi, M. et al., Science 281, 363, 365 (1998); Lysov, I. et al., Dokl Akad Nauk SSSR 303, 1508-1511 (1988); Bains W. & Smith G. C. J. Theor Biol 135, 303-307(1988); Drnanac, R. et al., Genomics 4, 114-128 (1989); Khrapko, K. R. et al., FEBS Lett 256. 118-122 (1989); Pevzner P. A. J Biomol Struct Dyn 7, 63-73 (1989); Southern, E. M. et al., Genomics 13, 1008-1017 (1992).)

If the beads are to be used in a pyrophosphate-based sequencing reaction (described, e.g., in U.S. Pat. Nos. 6,274, 320, 6,258,568 and 6,210,891, and incorporated in toto herein by reference), then it is necessary to remove the second strand of the PCR product and anneal a sequencing primer to the single stranded template that is bound to the bead. The second strand may be melted away using any number of commonly known methods such as addition of NaOH, application of low ionic (e.g., salt) strength, enzymatic degradation or displacement of the second strand, or heat processing. Following this strand removal step, the beads are pelleted and the supernatant is discarded. The beads are resuspended in an annealing buffer, and a sequencing primer or other non-amplification primer is added. The primer is annealed to the single stranded amplification product. This can be accomplished by using an appropriate annealing buffer and temperature conditions, e.g., as according to standard procedures in the art.

Purifying the Beads

At this point, the amplified nucleic acid on the bead may be sequenced either directly on the bead or in a different reaction vessel. In an embodiment of the present invention, the nucleic acid is sequenced directly on the bead by transferring the bead to a reaction vessel and subjecting the nucleic acid to a sequencing reaction (e.g., pyrophosphate or Sanger sequencing). Alternatively, the beads may be isolated and the nucleic acid may be removed from each bead and sequenced. In either case, the sequencing steps may be performed on each individual bead. However, this method, while commercially viable and technically feasible, may not be most effective because many of the beads will be "negative" beads (i.e., beads without amplified nucleic acid attached). In such cases, the optional process outlined below may be used to remove negative beads prior to distribution onto multiwell (e.g., picotiter) plates.

A high percentage of the beads may be negative if the goal is to minimize the number of beads that are associated with two or more different species of nucleic acid templates. For optimal pyrophosphate sequencing, each bead should contain multiple copies of a single species of nucleic acid. This can be achieved by maximizing the total number of beads combined with a single fragment of nucleic acid before amplification. For example, the following mathematical model can be used.

For the general case of N number of DNAs randomly distributed with M number of beads, the relative bead population associated with any number of DNAs depends on the ratio of N/M. The fraction of beads associated with N DNAs R(N) may be calculated using the Poisson distribution:

$$R(N) = \exp(-(N/M)) \times (N/M)^N / N!$$ (where × is the multiplication symbol)

Table 2, below, shows some calculated values for various N/M (the average DNA fragment-to-bead ratio) and N (the number of fragments associated with a bead).

TABLE 2

| N/M | 0.1 | 0.5 | 1 | 2 |
|---|---|---|---|---|
| R(0) | 0.9 | 0.61 | 0.37 | 0.13 |
| R(1) | 0.09 | 0.3 | 0.37 | 0.27 |
| R(N > 1) | 0.005 | 0.09 | 0.26 | 0.59 |

In Table 2, the top row denotes the various ratios of N/M. R(0) denotes the fraction of beads with no DNA, R(1) denotes the fraction of beads with one DNA (before amplification), and R(N>1) denotes the fraction of DNA with more than one DNA (before amplification).

Table 2 indicates that the maximum fraction of beads associated with a single DNA fragment is 0.37 (37%) and this occurs at a fragment-to-bead ratio of one-to-one. In this mixture, about 63% of the beads cannot be used for sequencing because they are associated with no DNA or they are associated with more than one species of DNA. However, controlling the fragment-to-bead ratio requires complex calculations, and variability can produce bead batches with a significantly smaller fraction of useable beads.

This inefficiency can be significantly ameliorated if beads containing amplicon (originating from the association with at least one fragment) are separated from those without amplicon (originating from beads with no associated fragments). An amplicon is defined as any nucleic acid molecules produced by an in vitro nucleic amplification technique. To increase efficiency, binding can be performed using low fragment-to-bead ratios (N/M<1). This minimizes the number of beads associated with more than one DNA. A separation step can be used to remove most or all of the beads with no DNA, leaving an enriched population of beads with one or more species of amplified DNA. This enriched population may be analyzed by any method of sequencing such as, for example, pyrophosphate sequencing. Because the fraction of beads with one amplicon (N=1) is enriched, any method of sequencing can be applied more efficiently.

As an example, with an average fragment-to-bead ratio of 0.1, 90% of the beads will carry no amplicon, 9% of the beads will carry one amplicon, and 0.5% of the beads will carry more than one amplicon. The enrichment described herein below will remove the 90% of the zero amplicon beads leaving a population of beads where the fraction available for sequencing (N=1) is:

1−(0.005/0.09)=94%.

Dilution of the fragment to bead mixture, along with separation of beads containing amplicon can yield an enrichment of 2.5 fold over the optimal unenriched method. For example, 94%/37% (See Table 2, above, N/M=1)=2.5. An additional benefit of the enrichment procedure described herein below is that the ultimate fraction of beads useful for sequencing is relatively insensitive to variability in N/M. Thus, complex calculations to derive the optimal N/M ratio are either unnecessary or may be performed with lower levels of precision. Accordingly, the methods of the invention can be easily adapted for use by less trained personnel or automation. An additional benefit of these methods is that the zero amplicon beads may be recycled and reused. While recycling is not necessary, it may reduce cost or the total bulk of reagents making the method of the invention more suitable for some purposes such as, for example, portable sampling, remote robotic sampling, and the like. In addition, the collective benefits of the disclosed methods (e.g., adaptation for less trained personnel, automation, and recycling of reagents) will reduce the costs of the methods. The enrichment procedure is described in more detail below.

The enrichment procedure may be used to treat beads that have been amplified in the bead emulsion method described above. The amplification is designed so that each amplified nucleic acid molecule contains the same sequence at its 3' end. The nucleotide sequence may be a 20-mer but may be any sequence from 15 bases or more such as 25 bases, 30 bases, 35 bases, 40 bases, or longer. While longer oligonucleotide ends are functional, they are not necessary. This 3' sequence may be introduced at the end of an amplified nucleic acid by one of skill in the art. For example, if PCR is used for amplification of a DNA template, the sequence may be included as part of one member of the PCR primer pair.

A schematic of the enrichment process is depicted in FIG. 3. In this process, the amplicon-bound bead is mixed with four empty beads to create a fragment-diluted amplification bead mixture. In step 1, a biotinylated primer complementary to the 3' end of the amplicon is annealed to the amplicon. In step 2, DNA polymerase and the four natural deoxynucleotide triphosphates (dNTPs) are added to the bead mixture and the biotinylated primer is extended. This extension is to enhance the bonding between the biotinylated primer and the bead-bound DNA. This step may be omitted if the biotinylated primer—DNA bond is strong (e.g., in a high ionic environment). In Step 3, streptavidin coated beads susceptible to attraction by a magnetic field (referred to herein as "magnetic streptavidin beads") are introduced to the bead mixtures. Magnetic beads are commercially available, for example, from Dynal (M290). The streptavidin capture moieties binds biotin groups hybridized to the amplicons, thereby binding the amplicon-bound beads to the magnetic streptavidin beads.

In step 5, a magnetic field (represented by a magnet) is applied near the reaction mixture, which causes the magnetic streptavidin beads/amplicon bound bead complexes to be positioned along one side of the tube most proximal to the magnetic field. Magnetic beads without amplicon bound beads attached are also expected to be positioned along the same side. Beads without amplicons remain in solution. The bead mixture is washed and the beads not bound by the magnet (i.e., the empty beads) are removed and discarded. In step 6, the extended biotinylated primer strand is separated from the amplicon strand by "melting." This step that can be accomplished, for example, by heat or a change in pH. The heat may be 60° C. in low salt conditions (e.g., in a low ionic environment such as 0.1×SSC). The change in pH may be accomplished by the addition of NaOH. Next, the mixture is washed and the supernatant containing the amplicon bound beads is recovered, while the magnetic beads are retained by a magnetic field. The resultant enriched beads may be used for DNA sequencing. It is noted that the primer on the DNA capture bead may be the same as the primer of step 2, above. In this case, annealing of the amplicon-primer complementary strands (with or without extension) is the source of target-capture affinity.

The biotin streptavidin pair could be replaced by a variety of capture-target pairs. For example, capture-target pairs can employ reversible (e.g., cleavable) or irreversible linkages. Non-limiting examples of reversible linkages include thiol-thiol, digoxigenin/anti-digoxigenin, and linkages using VECTREX® Avidin DLA (Vector Laboratories, Burlingame, Calif.), CaptAvidin™, NeutrAvidin™, and D-desthiobiotin (Molecular Probes, Inc., Eugene, Oreg.).

As described above, step 2 of the enrichment process is optional. If step 2 is omitted, it may not be necessary to separate the magnetic beads from the amplicon bound beads. The amplicon bound beads, with the magnetic beads attached, may be used directly for sequencing. For example, separation may not be necessary if sequencing is to be performed in a microtiter or picotiter plate and the amplicon bound bead-magnetic bead complex can fit inside the well of the plate.

While the use of magnetic capture beads is convenient, capture moieties can encompass other binding surfaces. For example, streptavidin can be chemically bound to a surface such as the inner surface of a tube. In this case, the amplified bead mixture may be flowed through the tube. The amplicon bound beads will tend to be retained until "melting" while the empty beads will flow through. This arrangement may be particularly advantageous for automating the bead preparation process.

While the embodiments described above are particularly useful, other methods to separate beads can be envisioned. For example, the capture beads may be labeled with a fluorescent moiety which would make the target-capture bead complex fluorescent. The target capture bead complex may be separated by flow cytometry or fluorescence cell sorter. Using large capture beads would allow separation by filtering or other particle size separation techniques. Since both capture and target beads are capable of forming complexes with a number of other beads, it is possible to agglutinate a mass of cross-linked capture-target beads. The large size of the agglutinated mass would make separation possible by simply washing away the unagglutinated empty beads. These methods described are described in more detail, for example, in Bauer, J.; J. Chromatography B, 722 (1999) 55-69 and in Brody et al., Applied Physics Lett. 74 (1999) 144-146.

In one embodiment, the invention encompasses a method for amplifying one or more nucleic acids comprising the steps of: a) forming a water-in-oil emulsion to create a plurality of aqueous microreactors wherein at least one of the microreactors comprises a single nucleic acid template, a single bead capable of binding to the nucleic acid, and amplification reaction solution containing reagents necessary to perform nucleic acid amplification; b) amplifying the nucleic acids in the microreactors to form amplified copies of the nucleic acids; and c) binding the amplified copies to the beads in the microreactors.

The amplification reaction solution used with this method may be a polymerase chain reaction solution comprising nucleotide triphosphates, a thermostable polymerase, and nucleic acid primers suspended in a buffer compatible with polymerase chain reaction conditions. The polymerase chain reaction is may be an asymmetric polymerase chain reaction or a symmetric polymerase chain reaction. As examples, amplification may be carried out by transcription-based amplification, rapid amplification of cDNA ends, continuous flow amplification, or rolling circle amplification.

For use with this method, a majority of the microreactors may include a single nucleic acid. The method may be performed with at least 10,000 nucleic acids, or at least 50,000 nucleic acids. Each bead used with the method can be used to capture more than 10,000 amplification copies of a nucleic acid template. In various embodiments, the emulsion additionally contains emulsion stabilizers. The emulsion stabilizers may be Atlox 4912, Span 80, or combinations or mixtures thereof. The emulsion may be heat stable, e.g., to 95° C., and may be formed by the dropwise addition of the nucleic acid templates, beads, and amplification reaction solution into an oil. The microreactors may have an average size of 50 to 250 μm in diameter.

In another embodiment, the invention encompasses a library comprising a plurality of nucleic acid molecules, wherein each nucleic acid molecule is separately immobilized to a different bead, and wherein each bead comprises over 1,000,000 clonal amplification copies of each nucleic acid molecule, wherein the library is contained in a single vessel. As examples, the nucleic acid molecules may be genomic DNA, cDNA, episomal DNA, BAC DNA, or YAC DNA. The genomic DNA may be animal, plant, viral, bacterial, or fungal genomic DNA. Preferably, the genomic DNA is human genomic DNA or human cDNA. In certain aspects, the bead, e.g., a Sepharose bead, has a diameter of 2 microns to 100 microns.

The invention also encompasses a method for amplifying a nucleic acid comprising the steps of: a) providing a nucleic acid template to be amplified; b) providing a solid support material comprising a generally spherical bead having a diameter about 10 to about 80 m, wherein the bead is capable of binding to the nucleic acid template; c) mixing the nucleic acid template and the bead in an amplification reaction solution containing reagents necessary to perform a nucleic acid amplification reaction in a water-in-oil emulsion; d) amplifying the nucleic acid template to form amplified copies of the nucleic acid template; and e) binding the amplified copies to the bead.

As an option, the method can include an enrichment step to isolate beads which bind amplified copies of the nucleic acid away from beads to which no nucleic acid is bound. This enrichment step may be performed by electrophoresis, cell sorting, or affinity purification (e.g., with magnetic beads that bind nucleic acid). Preferably, at least 100,000 copies of each target nucleic acid molecule are bound to each bead, at least 1,000,000 copies of each target nucleic acid molecule are bound to each bead, or at least 1 to 20,000,000 copies of each target nucleic acid molecule are bound to each bead. In various aspects, the beads are Sepharose beads and amplified copies are bound to the beads by a binding pair such as antigen/antibody, ligand/receptor, polyhistidine/nickel, or avidin/biotin. The method can also include the steps of: f) separating the template carrying beads and magnetic bead; and g) removing the magnetic beads with a magnetic field. This separation may be achieved by incubation at a temperature greater than 45° C. or by incubating the template carrying beads and the magnetic beads in a solution with a basic pH.

The invention further encompasses a kit for conducting nucleic acid amplification of a nucleic acid template comprising: a) a nucleic acid capture bead; b) an emulsion oil; c) one or more emulsion stabilizers; and d) instructions for employing the kit.

Additionally, the invention encompasses a method for producing a clonal population of nucleic acids, comprising: a) providing a plurality of nucleic acid templates from 50-800 bp in length and beads capable of binding to the nucleic acid templates; b) mixing the nucleic acid templates and the beads in a biological reaction solution containing reagents necessary to amplify the nucleic acid templates; and c) forming an emulsion to create a plurality of microreactors comprising the nucleic acid templates, beads, and biological reaction solution, wherein at least one of the microreactors comprises a single nucleic acid template and a single bead encapsulated in the biological reaction solution, wherein the microreactors are contained in the same vessel.

In accordance with this method, the nucleic acids can be transcribed and translated to generate at least 10,000 copies of an expression product. The expression product may be bound to the beads by a binding pair selected from the group consisting of antigen/antibody, ligand/receptor, 6×his/nickel-nitrilotriacetic acid, and FLAG tag/FLAG antibody binding pairs. In certain aspects, the method produces a clonal population of proteins, such as antibodies, antibodies fragments, and engineered antibodies. The emulsion may comprise a plurality of thermostable microreactors, wherein the microreactors are 50 to 200 μm in diameter and comprise a biological reaction solution. The biological reaction solution may comprise reagents for performing polymerase chain reaction amplification reactions or coupled transcription and translation reactions. Preferably, a plurality of microreactors comprises a nucleic acid template, e.g., one or fewer nucleic acid templates, and one or fewer beads that bind to the nucleic acid templates.

EXAMPLES

Beam Emulsion PCR

The following procedures, including capture of the template DNA, DNA amplification, and recovery of the beads bound to amplified template, can be performed in a single tube. The emulsion format ensures the physical separation of the beads into 100-200 μm "microreactors" within this single tube, thus allowing for clonal amplification of the various templates. Immobilization of the amplification product is achieved through extension of the template along the oligonucleotides bound to the DNA capture beads. Typical, the copy number of the immobilized template ranges from 10 to 30 million copies per bead. The DNA capture beads affixed with multiple copies of a single species of nucleic acid template are ready for distribution onto PTPs.

The 300,000 75-picoliter wells etched in the PTP surface provide a unique array for the sequencing of short DNA templates in a massively parallel, efficient and cost-effective manner. However, this requires fairly large quantities (millions of copies) of clonal templates in each reaction well. The methods of the invention allow the user to clonally amplify single-stranded genomic template species thorough PCR reactions conducted in standard tubes or microtiter plates. Single copies of the template species may be mixed with capture beads, resuspended into complete PCR amplification solution, and emulsified into microreactors (100 to 200 μm in diameter), after which PCR amplification generates $10^7$-fold amplification of the initial template species. This procedure is much simpler and more cost-effective than previous methods.

Example 1: Binding Nucleic Acid Template to Capture Beads

This example describes preparation of a population of beads that preferably have only one unique nucleic acid template attached thereto. Successful clonal amplification depends on the delivery of a controlled number of template species (0.5 to 1) to each bead. Delivery of excess species can result in PCR amplification of a mixed template population, preventing generation of meaningful sequence data while a deficiency of species will result in fewer wells containing template for sequencing. This can reduce the extent of genome coverage provided by the sequencing phase. As a result, it is preferred that the template concentration be accurately determined through replicated quantitation, and that the binding protocol be followed as outlined below.

Template Quality Control

The success of the Emulsion PCR reaction is related to the quality of the template species. Regardless of the care and detail paid to the amplification phase, poor quality templates will impede successful amplification and the generation of meaningful sequence data. To prevent unnecessary loss of time and money, it is important to check the quality of the template material before initiating the Emulsion PCR phase of the process. Preferably, the library should pass two quality control steps before it is used in Emulsion PCR. Its concentration and the distribution of products it contains should be determined. Ideally, the library should appear as a heterogeneous population of fragments with little or no visible adapter dimers (e.g., ~90 bases). Also, amplification with PCR primers should result in a product smear ranging, for example, from 300 to 500 bp. Absence of amplification product may reflect failure to properly ligate the adaptors to the template, while the presence of a single band of any size may reflect contamination of the template.

Preparation of the PCR Solution

The main consideration for this phase is to prevent contamination of the PCR reaction mixture with stray amplicons. Contamination of the PCR reactions with a residual amplicon is one of the critical issues that can cause failure of a sequencing run. To reduce the possibility of contamination, proper lab technique should be followed, and reaction mixture preparation should be conducted in a clean room in a UV-treated laminar flow hood.

PCR Reaction Mix

For 200 μl PCR reaction mixture (enough for amplifying 600,000 beads), the following reagents were combined in a 0.2 ml PCR tube:

TABLE 3

|  | Stock | Final | Microliters |
| --- | --- | --- | --- |
| HIFI Buffer | 10 X | 1 X | 20 |
| treated nucleotides | 10 mM | 1 mM | 20 |
| Mg | 50 mM | 2 mM | 8 |
| BSA | 10% | 0.1% | 2 |
| Tween 80 | 1% | 0.01% | 2 |
| Ppase | 2 U | 0.003 U | 0.333333 |
| Primer MMP1a | 100 μM | 0.625 μM | 1.25 |
| Primer MMP1b | 10 μM | 0.078 μM | 1.56 |
| Taq polymerase | 5 U | 0.2 U | 8 |
| Water |  |  | 136.6 |
| Total |  |  | 200 |

The tube was vortexed thoroughly and stored on ice until the beads are annealed with template.

DNA Capture Beads 1. 600,000 DNA capture beads were transferred from the stock tube to a 1.5 ml microfuge tube. The exact amount used will depend on bead concentration of formalized reagent.
2. The beads were pelleted in a benchtop mini centrifuge and supernatant was removed.
3. Steps 4-11 were performed in a PCR Clean Room.
4. The beads were washed with 1 mL of 1×Annealing Buffer.
5. The capture beads were pelleted in the microcentrifuge. The tube was turned 180° and spun again.
6. All but approximately 10 μl of the supernatant was removed from the tube containing the beads. The beads were not disturbed.
7. 1 mL of 1×Annealing Buffer was added and this mixture was incubated for 1 minute. The beads were then pelleted as in step 5.
8. All but approximately 100 μL of the material from the tube was removed.
9. The remaining beads and solution were transferred to a PCR tube.
10. The 1.5 mL tube was washed with 150 μL of 1×Annealing Buffer by pipetting up and down several times. This was added to the PCR tube containing the beads.
11. The beads were pelleted as in step 5 and all but 10 μL of supernatant was removed, taking care to not disturb the bead pellet.
12. An aliquot of quantitated single-stranded template DNA (sstDNA) was removed. The final concentration was 200,000-sst DNA molecules/μl.
13. 3 μl of the diluted sstDNA was added to PCR tube containing the beads. This was equivalent to 600,000 copies of sstDNA.
14. The tube was vortexed gently to mix contents.
15. The sstDNA was annealed to the capture beads in a PCR thermocycler with the program 80Anneal stored in the EPCR folder on the MJ Thermocycler, using the following protocol:

Decrease by 0.1° C./sec to 60° C.;
Hold at 60° C. for 1 minute;
Decrease by 0.1° C./sec to 50° C.;
Hold at 50° C. for 1 minute;
Decrease by 0.1° C./sec to 40° C.;
Hold at 40° C. for 1 minute;
Decrease by 0.1° C./sec to 20° C.; and
Hold at 10° C. until ready for next step.

In most cases, beads were used for amplification immediately after template binding. If beads were not used immediately, they should were stored in the template solution at 4° C. until needed. After storage, the beads were treated as follows.

16. As in step 6, the beads were removed from the thermocycler, centrifuged, and annealing buffer was removed without disturbing the beads.

17. The beads were stored in an ice bucket until emulsification (Example 2).

18. The capture beads included, on average, 0.5 to 1 copies of sstDNA bound to each bead, and were ready for emulsification.

Example 2: Emulsification

This example describes how to create a heat-stable water-in-oil emulsion containing about 3,000 PCR microreactors per microliter. Outlined below is a protocol for preparing the emulsion.

1. 200 µl of PCR solution was added to the 600,000 beads (both components from Example 1).
2. The solution was pipetted up and down several times to resuspend the beads.
3. The PCR-bead mixture was allowed to incubate at room temperature for 2 minutes to equilibrate the beads with PCR solution.
4. 400 µl of Emulsion Oil was added to a UV-irradiated 2 ml microfuge tube.
5. An "amplicon-free" ¼" stir magnetic stir bar was added to the tube of Emulsion Oil.

An amplicon-free stir bar was prepared as follows. A large stir bar was used to hold a ¼" stir bar. The stir bar was then:
   Washed with DNA-Off (drip or spray);
   Rinsed with picopure water;
   Dried with a Kimwipe edge; and
   UV irradiated for 5 minutes.

6. The magnetic insert of a Dynal MPC-S tube holder was removed. The tube of Emulsion Oil was placed in the tube holder. The tube was set in the center of a stir plate set at 600 rpm.
7. The tube was vortexed extensively to resuspend the beads. This ensured that there was minimal clumping of beads.
8. Using a P-200 pipette, the PCR-bead mixture was added drop-wise to the spinning oil at a rate of about one drop every 2 seconds, allowing each drop to sink to the level of the magnetic stir bar and become emulsified before adding the next drop. The solution turned into a homogeneous milky white liquid with a viscosity similar to mayonnaise.
9. Once the entire PCR-bead mixture was been added, the microfuge tube was flicked a few times to mix any oil at the surface with the milky emulsion.
10. Stirring was continued for another 5 minutes.
11. Steps 9 and 10 were repeated.
12. The stir bar was removed from the emulsified material by dragging it out of the tube with a larger stir bar.
13. 10 µL of the emulsion was removed and placed on a microscope slide. The emulsion was covered with a cover slip and the emulsion was inspected at 50× magnification (10× ocular and 5× objective lens). A "good" emulsion was expected to include primarily single beads in isolated droplets (microreactors) of PCR solution in oil.
14. A suitable emulsion oil mixture with emulsion stabilizers was made as follows. The components for the emulsion mixture are shown in Table 4.

TABLE 4

| Ingredient | Quantity Required | Source | Ref. Number |
|---|---|---|---|
| Sigma Light Mineral Oil | 94.5 g | Sigma | M-5904 |
| Atlox 4912 | 1 g | Uniqema | NA |
| Span 80 | 4.5 g | Uniqema | NA |

The emulsion oil mixture was made by prewarming the Atlox 4912 to 60° C. in a water bath. Then, 4.5 grams of Span 80 was added to 94.5 grams of mineral oil to form a mixture. Then, one gram of the prewarmed Atlox 4912 was added to the mixture. The solutions were placed in a closed container and mixed by shaking and inversion. Any sign that the Atlox was settling or solidifying was remedied by warming the mixture to 60° C., followed by additional shaking.

Example 3: Amplification

This example describes amplification of the template DNA in the bead-emulsion mixture. According to this protocol of the invention, the DNA amplification phase of the process takes 3 to 4 hours. After the amplification is complete, the emulsion may be left on the thermocycler for up to 12 hours before beginning the process of isolating the beads. PCR thermocycling was performed by placing 50 to 100 µl of the emulsified reaction mixture into individual PCR reaction chambers (i.e., PCR tubes). PCR was performed as follows:

1. The emulsion was transferred in 50-100 µL, amounts into approximately 10 separate PCR tubes or a 96-well plate using a single pipette tip. For this step, the water-in-oil emulsion was highly viscous.
2. The plate was sealed, or the PCR tube lids were closed, and the containers were placed into in a MJ thermocycler with or without a 96-well plate adaptor.
3. The PCR thermocycler was programmed to run the following program:
   1 cycle (4 minutes at 94° C.)—Hotstart Initiation;
   40 cycles (30 seconds at 94° C., 30 seconds at 58° C., 90 seconds at 68° C.);
   25 cycles (30 seconds at 94° C., 6 minutes at 58° C.); and
   Storage at 14° C.
4. After completion of the PCR reaction, the amplified material was removed in order to proceed with breaking the emulsion and bead recovery.

Example 4: Breaking the Emulsion and Bead Recovery

This example describes how to break the emulsion and recover the beads with amplified template thereon. Preferably, the post-PCR emulsion should remain intact. The lower phase of the emulsion should, by visual inspection, remain a milky white suspension. If the solution is clear, the emulsion may have partially resolved into its aqueous and oil phases, and it is likely that many of the beads will have a mixture of templates. If the emulsion has broken in one or two of the tubes, these samples should not be combined with the others. If the emulsion has broken in all of the tubes, the procedure should not be continued.

1. All PCR reactions from the original 600 µl sample were combined into a single 1.5 ml microfuge tube using a single pipette tip. As indicated above, the emulsion was quite viscous. In some cases, pipetting was repeated several times for each tube. As much material as possible was transferred to the 1.5 ml tube.

2. The remaining emulsified material was recovered from each PCR tube by adding 50 µl of Sigma Mineral Oil into each sample. Using a single pipette tip, each tube was pipetted up and down a few times to resuspend the remaining material.

3. This material was added to the 1.5 ml tube containing the bulk of the emulsified material.

4. The sample was vortexed for 30 seconds.

5. The sample was spun for 20 minutes in the tabletop microfuge tube at 13.2K rpm in the Eppendorf microcentrifuge.

6. The emulsion separated into two phases with a large white interface. As much of the top, clear oil phase as possible was removed. The cloudy material was left in the tube. Often a white layer separated the oil and aqueous layers. Beads were often observed pelleted at the bottom of the tube.

7. The aqueous layer above the beads was removed and saved for analysis (gel analysis, Agilent 2100, and Taqman). If an interface of white material persisted above the aqueous layer, 20 microliters of the underlying aqueous layer was removed. This was performed by penetrating the interface material with a pipette tip and withdrawing the solution from underneath.

8. In the PTP Fabrication and Surface Chemistry Room Fume Hood, 1 ml of Hexanes was added to the remainder of the emulsion.

9. The sample was vortexed for 1 minute and spun at full speed for 1 minute.

10. In the PTP Fabrication and Surface Chemistry Room Fume Hood, the top, oil/hexane phase was removed and placed into the organic waste container.

11. 1 ml of 1×Annealing Buffer was added in 80% Ethanol to the remaining aqueous phase, interface, and beads.

12. The sample was vortexed for 1 minute or until the white substance dissolved.

13. The sample was centrifuged for 1 minute at high speed. The tube was rotated 180 degrees, and spun again for 1 minute. The supernatant was removed without disturbing the bead pellet.

14. The beads were washed with 1 ml of 1×Annealing Buffer containing 0.1% Tween 20 and this step was repeated.

Example 5: Single Strand Removal and Primer Annealing

If the beads are to be used in a pyrophosphate-based sequencing reaction, then it is necessary to remove the second strand of the PCR product and anneal a sequencing primer to the single stranded template that is bound to the bead. This example describes a protocol for accomplishing that.

1. The beads were washed with 1 ml of water, and spun twice for 1 minute. The tube was rotated 180° between spins. After spinning, the aqueous phase was removed.

2. The beads were washed with 1 ml of 1 mM EDTA. The tube was spun as in step 1 and the aqueous phase was removed.

3. 1 ml of 0.125 M NaOH was added and the sample was incubated for 8 minutes.

4. The sample was vortexed briefly and placed in a microcentrifuge.

5. After 6 minutes, the beads were pelleted as in step 1 and as much solution as possible was removed.

6. At the completion of the 8 minute NaOH incubation, 1 ml of 1×Annealing Buffer was added.

7. The sample was briefly vortexed, and the beads were pelleted as in step 1. As much supernatant as possible was removed, and another 1 ml of 1×Annealing buffer was added.

8. The sample was briefly vortexed, the beads were pelleted as in step 1, and 800 µl of 1×Annealing Buffer was removed.

9. The beads were transferred to a 0.2 ml PCR tube.

10. The beads were transferred and as much Annealing Buffer as possible was removed, without disturbing the beads.

11. 100 µl of 1×Annealing Buffer was added.

12. 4 µl of 100 µM sequencing primer was added. The sample was vortexed just prior to annealing.

13. Annealing was performed in a MJ thermocycler using the "80Anneal" program.

14. The beads were washed three times with 200 µl of 1×Annealing Buffer and resuspended with 100 µl of 1×Annealing Buffer.

15. The beads were counted in a Hausser Hemacytometer. Typically, 300,000 to 500,000 beads were recovered (3,000-5,000 beads/µL).

16. Beads were stored at 4° C. and could be used for sequencing for 1 week.

Example 6: Optional Enrichment Step

The beads may be enriched for amplicon containing bead using the following procedure. Enrichment is not necessary but it could be used to make subsequent molecular biology techniques, such as DNA sequencing, more efficient.

Fifty microliters of 10 µM (total 500 pmoles) of biotin-sequencing primer was added to the Sepharose beads containing amplicons from Example 5. The beads were placed in a thermocycler. The primer was annealed to the DNA on the bead by the thermocycler annealing program of Example 2.

After annealing, the sepharose beads were washed three times with Annealing Buffer containing 0.1% Tween 20. The beads, now containing ssDNA fragments annealed with biotin-sequencing primers, were concentrated by centrifugation and resuspended in 200 µl of BST binding buffer. Ten microliters of 50,000 unit/ml Bst-polymerase was added to the resuspended beads and the vessel holding the beads was placed on a rotator for five minutes. Two microliters of 10 mM dNTP mixture (i.e., 2.5 µl each of 10 mM dATP, dGTP, dCTP and dTTP) was added and the mixture was incubated for an additional 10 minutes at room temperature. The beads were washed three times with annealing buffer containing 0.1% Tween 20 and resuspended in the original volume of annealing buffer.

Fifty microliters of Dynal Streptavidin beads (Dynal Biotech Inc., Lake Success, N.Y.; M270 or MyOne™ beads at 10 mg/ml) was washed three times with Annealing Buffer containing 0.1% Tween 20 and resuspended in the original volume in Annealing Buffer containing 0.1% Tween 20. Then the Dynal bead mixture was added to the resuspended sepharose beads. The mixture was vortexed and placed in a rotator for 10 minutes at room temperature.

The beads were collected on the bottom of the test tube by centrifugation at 2300 g (500 rpm for Eppendorf Centrifuge 5415D). The beads were resuspended in the original volume of Annealing Buffer containing 0.1% Tween 20. The mixture, in a test tube, was placed in a magnetic separator (Dynal). The beads were washed three times with Annealing Buffer containing 0.1% Tween 20 and resuspended in the original volume in the same buffer. The beads without amplicons were removed by wash steps, as previously described. Only Sepharose beads containing the appropriated DNA fragments were retained.

The magnetic beads were separated from the sepharose beads by addition of 500 µl of 0.125 M NaOH. The mixture was vortexed and the magnetic beads were removed by magnetic separation. The Sepharose beads remaining in solution was transferred to another tube and washed with 400 µl of 50 mM Tris Acetate until the pH was stabilized at 7.6.

Example 7: Nucleic Acid Sequencing Using Bead Emulsion PCR

The following experiment was performed to test the efficacy of the bead emulsion PCR. For this protocol, 600,000 Sepharose beads, with an average diameter of 25-35 µm (as supplied my the manufacturer) were covalently attached to capture primers at a ratio of 30-50 million copies per bead. The beads with covalently attached capture primers were mixed with 1.2 million copies of single stranded Adenovirus Library. The library constructs included a sequence that was complimentary to the capture primer on the beads.

The adenovirus library was annealed to the beads using the procedure described in Example 1. Then, the beads were resuspended in complete PCR solution. The PCR Solution and beads were emulsified in 2 volumes of spinning emulsification oil using the same procedure described in Example 2. The emulsified (encapsulated) beads were subjected to amplification by PCR as outlined in Example 3. The emulsion was broken as outlined in Example 4. DNA on beads was rendered single stranded, sequencing primer was annealed using the procedure of Example 5.

Next, 70,000 beads were sequenced simultaneously by pyrophosphate sequencing using a pyrophosphate sequencer from 454 Life Sciences (New Haven, Conn.) (see co-pending application of Lohman et al., filed concurrently herewith entitled Methods of Amplifying and Sequencing Nucleic Acids" U.S. Ser. No. 60/476,592 filed Jun. 6, 2003). Multiple batches of 70,000 beads were sequenced and the data were listed in Table 5, below.

TABLE 5

| Alignment Error | Alignments | | | | | Inferred |
|---|---|---|---|---|---|---|
| Tolerance | None | Single | Multiple | Unique | Coverage | Read Error |
| 0% | 47916 | 1560 | | 1110 | 54.98% | 0.00% |
| 5% | 46026 | 3450 | | 2357 | 83.16% | 1.88% |
| 10% | 43474 | 6001 | 1 | 3742 | 95.64% | 4.36% |

Table 5 shows the results obtained from BLAST analysis comparing the sequences obtained from the pyrophosphate sequencer against Adenovirus sequence. The first column shows the error tolerance used in the BLAST program. The last column shows the real error as determined by direct comparison to the known sequence.

Bead Emulsion PCR for Double Ended Sequencing

Example 8: Template Quality Control

As indicated previously, the success of the Emulsion PCR reaction was found to be related to the quality of the single stranded template species. Accordingly, the quality of the template material was assessed with two separate quality controls before initiating the Emulsion PCR protocol. First, an aliquot of the single-stranded template was run on the 2100 BioAnalyzer (Agilent). An RNA Pico Chip was used to verify that the sample included a heterogeneous population of fragments, ranging in size from approximately 200 to 500 bases. Second, the library was quantitated using the RiboGreen fluorescence assay on a Bio-Tek FL600 plate fluorometer. Samples determined to have DNA concentrations below 5 ng/µl were deemed too dilute for use.

Example 9: DNA Capture Bead Synthesis

Packed beads from a 1 mL N-hydroxysuccinimide ester (NHS)-activated Sepharose HP affinity column (Amersham Biosciences, Piscataway, N.J.) were removed from the column. The 30-25 µm size beads were selected by serial passage through 30 and 25 µm pore filter mesh sections (Sefar America, Depew, N.Y., USA). Beads that passed through the first filter, but were retained by the second were collected and activated as described in the product literature (Amersham Pharmacia Protocol #71700600AP). Two different amine-labeled HEG (hexaethyleneglycol) long capture primers were obtained, corresponding to the 5' end of the sense and antisense strand of the template to be amplified, (5'-Amine-3 HEG spacers gcttacctgaccgacctctgcc-tatccctgttgcgtgtc-3'; SEQ ID NO:1; and 5'-Amine-3 HEG spacers ccattccccagctcgtcttgccatctgttccctccctgtc-3'; SEQ ID NO:2) (IDT Technologies, Coralville, Iowa, USA). The primers were designed to capture of both strands of the amplification products to allow double ended sequencing, i.e., sequencing the first and second strands of the amplification products. The capture primers were dissolved in 20 mM phosphate buffer, pH 8.0, to obtain a final concentration of 1 mM. Three microliters of each primer were bound to the sieved 30-25 µm beads. The beads were then stored in a bead storage buffer (50 mM Tris, 0.02% Tween and 0.02% sodium azide, pH 8). The beads were quantitated with a hemacytometer (Hausser Scientific, Horsham, Pa., USA) and stored at 4° C. until needed.

Example 10: PCR Reaction Mix Preparation and Formulation

As with any single molecule amplification technique, contamination of the reactions with foreign or residual amplicon from other experiments could interfere with a sequencing run. To reduce the possibility of contamination, the PCR reaction mix was prepared in a in a UV-treated laminar flow hood located in a PCR clean room. For each 600,000 bead emulsion PCR reaction, the following reagents were mixed in a 1.5 ml tube: 225 µl of reaction mixture (1× Platinum HiFi Buffer (Invitrogen)), 1 mM dNTPs, 2.5 mM MgSO$_4$ (Invitrogen), 0.1% BSA, 0.01% Tween, 0.003 U/µl thermostable PPi-ase (NEB), 0.125 µM forward primer (5'-gcttacctgaccgacctctg-3'; SEQ ID NO:3) and 0.125 µM reverse primer (5'-ccattccccagctcgtcttg-3'; SEQ ID NO:4) (IDT Technologies, Coralville, Iowa, USA) and 0.2 U/µl Platinum Hi-Fi Taq Polymerase (Invitrogen). Twenty-five microliters of the reaction mixture was removed and stored in an individual 200 µl PCR tube for use as a negative control. Both the reaction mixture and negative controls were stored on ice until needed.

Example 11: Binding Template Species to DNA Capture Beads

Successful clonal DNA amplification for sequencing relates to the delivery of a controlled number of template species to each bead. For the experiments described herein below, the typical target template concentration was determined to be 0.5 template copies per capture bead. At this concentration, Poisson distribution dictates that 61% of the beads have no associated template, 30% have one species of template, and 9% have two or more template species. Delivery of excess species can result in the binding and subsequent amplification of a mixed population (2 or more species) on a single bead, preventing the generation of meaningful sequence data. However, delivery of too few species will result in fewer wells containing template (one species per bead), reducing the extent of sequencing coverage. Consequently, it was deemed that the single-stranded library template concentration was important.

Template nucleic acid molecules were annealed to complimentary primers on the DNA capture beads by the following method, conducted in a UV-treated laminar flow hood. Six hundred thousand DNA capture beads suspended in bead storage buffer (see Example 9, above) were transferred to a 200 µl PCR tube. The tube was centrifuged in a benchtop mini centrifuge for 10 seconds, rotated 180°, and spun for an additional 10 seconds to ensure even pellet formation. The supernatant was removed, and the beads were washed with 200 µl of Annealing Buffer (20 mM Tris, pH 7.5 and 5 mM magnesium acetate). The tube was vortexed for 5 seconds to resuspend the beads, and the beads were pelleted as before. All but approximately 10 µl of the supernatant above the beads was removed, and an additional 200 µl of Annealing Buffer was added. The beads were again vortexed for 5 seconds, allowed to sit for 1 minute, and then pelleted as before. All but 10 µl of supernatant was discarded.

Next, 1.5 µl of 300,000 molecules/µl template library was added to the beads. The tube was vortexed for 5 seconds to mix the contents, and the templates were annealed to the beads in a controlled denaturation/annealing program preformed in an MJ thermocycler. The program allowed incubation for 5 minutes at 80° C., followed by a decrease by 0.1° C./sec to 70° C., incubation for 1 minute at 70° C., decrease by 0.1° C./sec to 60° C., hold at 60° C. for 1 minute, decrease by 0.1° C./sec to 50° C., hold at 50° C. for 1 minute, decrease by 0.1° C./sec to 20° C., hold at 20° C. Following completion of the annealing process, the beads were removed from the thermocycler, centrifuged as before, and the Annealing Buffer was carefully decanted. The capture beads included on average 0.5 copy of single stranded template DNA bound to each bead, and were stored on ice until needed.

Example 12: Emulsification

The emulsification process creates a heat-stable water-in-oil emulsion containing 10,000 discrete PCR microreactors per microliter. This serves as a matrix for single molecule, clonal amplification of the individual molecules of the target library. The reaction mixture and DNA capture beads for a single reaction were emulsified in the following manner. In a UV-treated laminar flow hood, 200 µl of PCR solution (from Example 10) was added to the tube containing the 600,000 DNA capture beads (from Example 11). The beads were resuspended through repeated pipetting. After this, the PCR-bead mixture was incubated at room temperature for at least 2 minutes, allowing the beads to equilibrate with the PCR solution. At the same time, 450 µl of Emulsion Oil (4.5% (w:w) Span 80, 1% (w:w) Atlox 4912 (Uniqema, Delaware) in light mineral oil (Sigma)) was aliquotted into a flat-topped 2 ml centrifuge tube (Dot Scientific) containing a sterile ¼ inch magnetic stir bar (Fischer). This tube was then placed in a custom-made plastic tube holding jig, which was then centered on a Fisher Isotemp digital stirring hotplate (Fisher Scientific) set to 450 RPM.

Figure 4:
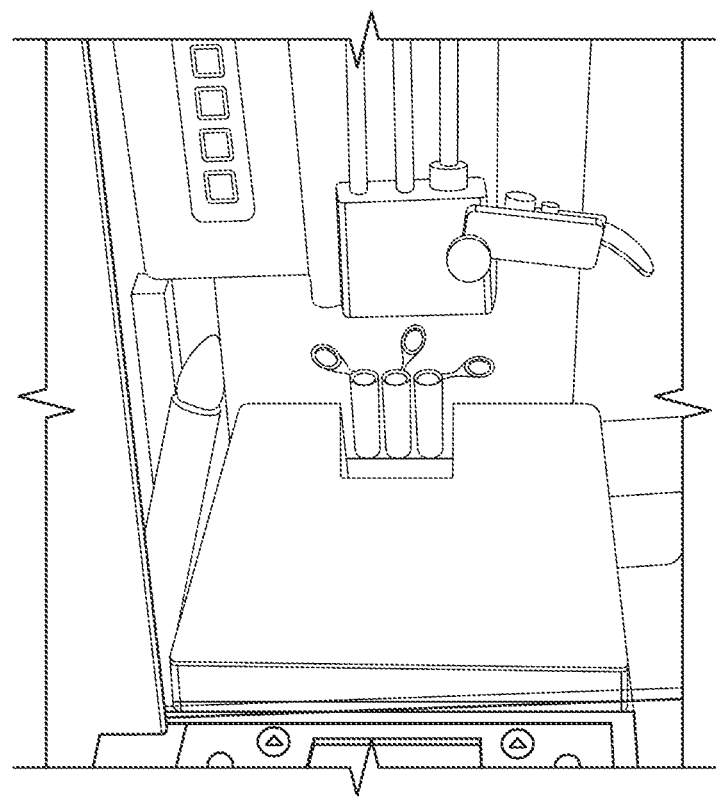
FIG. 4 Depiction of jig used to hold tubes on the stir plate below vertical syringe pump. The jig was modified to hold three sets of bead emulsion amplification reaction mixtures. The syringe was loaded with the PCR reaction mixture and beads.
Figure 5:
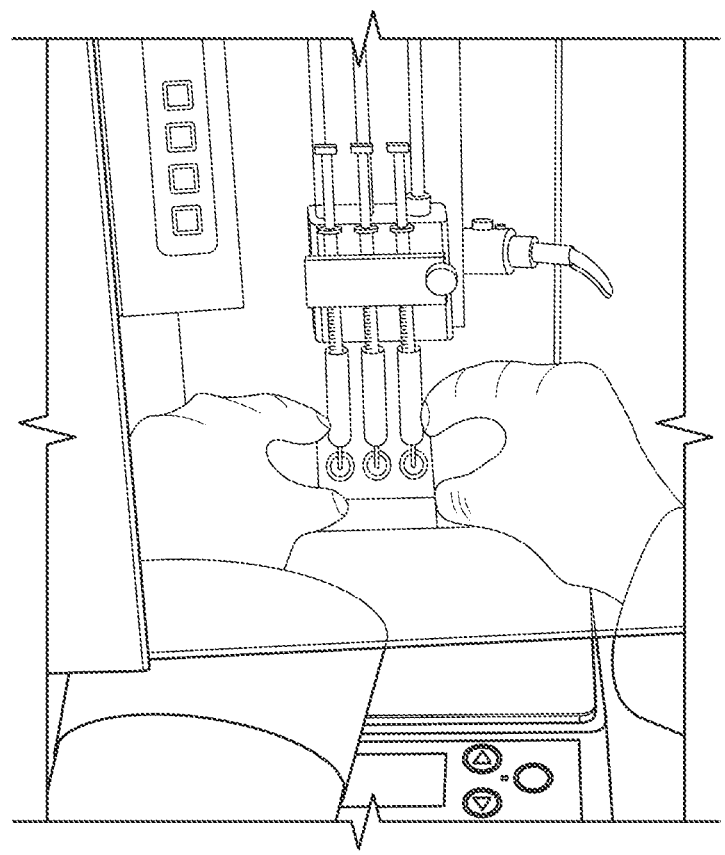
FIG. 5 Depiction of optimal placement of syringes in vertical syringe pump and orientation of emulsion tubes below syringe outlets.
Figure 6:
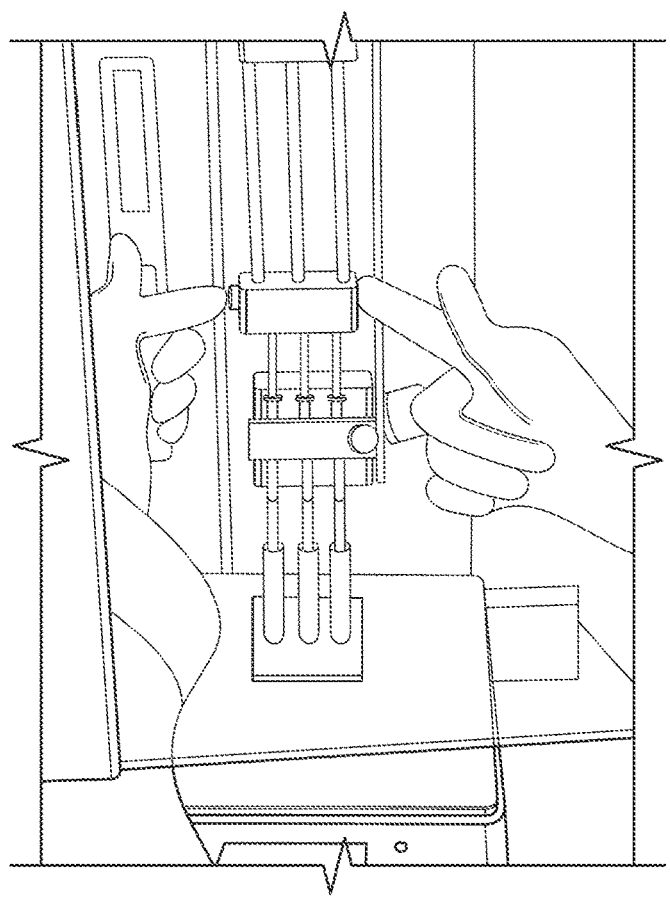
FIG. 6 Depiction of optimal placement of syringe pump pusher block against syringe plungers, and optimal orientation of jig on the stir plate. Using this arrangement, the syringe contents were expelled into the agitated emulsion oil.

The PCR-bead solution was vortexed for 15 seconds to resuspend the beads. The solution was then drawn into a 1 ml disposable plastic syringe (Benton-Dickenson) affixed with a plastic safety syringe needle (Henry Schein). The syringe was placed into a syringe pump (Cole-Parmer) modified with an aluminum base unit orienting the pump vertically rather than horizontally (e.g., FIGS. 4-6). The tube with the emulsion oil was aligned on the stir plate so that it was centered below the plastic syringe needle and the magnetic stir bar was spinning properly. The syringe pump was set to dispense 0.6 ml at 5.5 ml/hr. The PCR-bead solution was added to the emulsion oil in a dropwise fashion. Care was taken to ensure that the droplets did not contact the side of the tube as they fell into the spinning oil.

Once the emulsion was formed, great care was taken to minimize agitation of the emulsion during both the emulsification process and the post-emulsification aliquotting steps. It was found that vortexing, rapid pipetting, or excessive mixing could cause the emulsion to break, destroying the discrete microreactors. In forming the emulsion, the two solutions turned into a homogeneous milky white mixture with the viscosity of mayonnaise. The contents of the syringe were emptied into the spinning oil. Then, the emulsion tube was removed from the holding jig, and gently flicked with a forefinger until any residual oil layer at the top of the emulsion disappeared. The tube was replaced in the holding jig, and stirred with the magnetic stir bar for an additional minute. The stir bar was removed from the emulsion by running a magnetic retrieval tool along the outside of the tube, and the stir bar was discarded.

Figure 7:
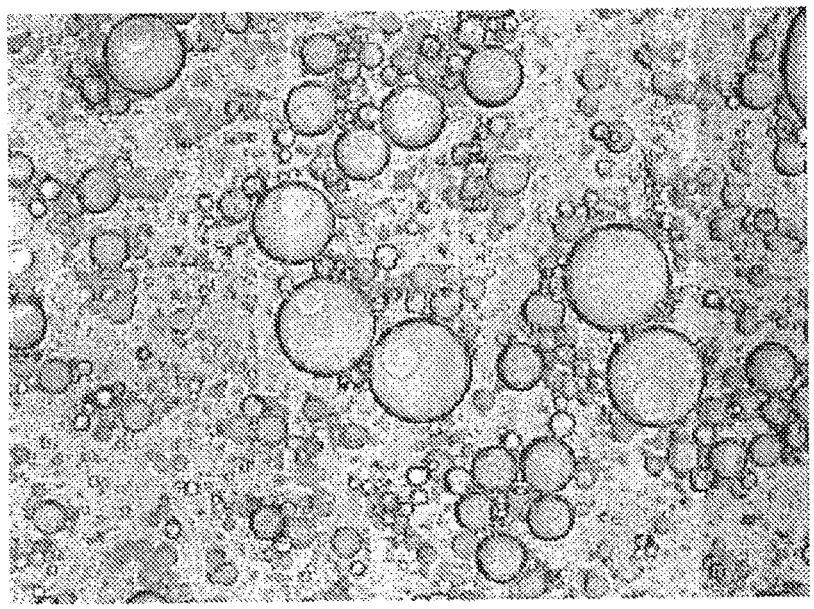
FIG. 7 Depiction of beads (see arrows) suspended in individual microreactors according to the methods of the invention.
Figure 8A:
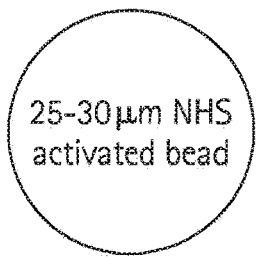
FIGS. 8A-8C Schematic showing the initial stages of bead emulsion amplification used in conjunction with double ended sequencing. The NETS-activated bead (FIG. 8A) is attached with capture primers (FIG. 8B), and encapsulated in a microreactor comprising the DNA capture bead and template (FIG. 8C).
Figure 8B:
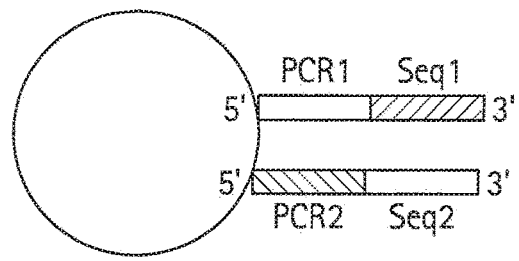
Figure 8C:
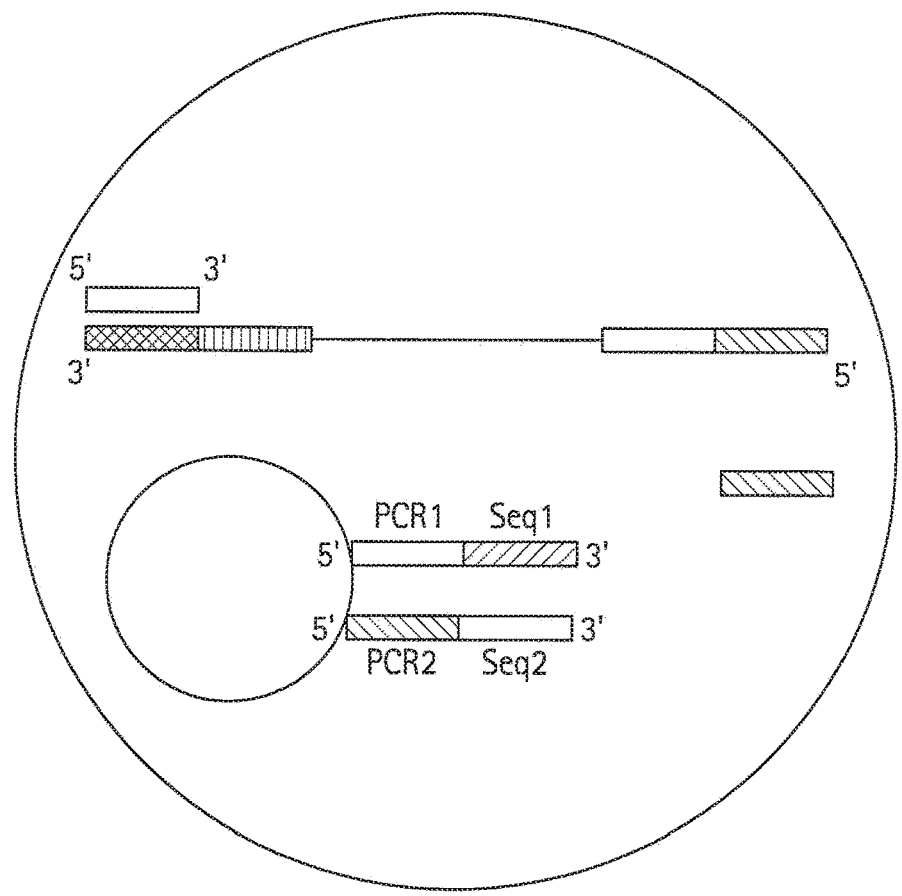
Figure 9:
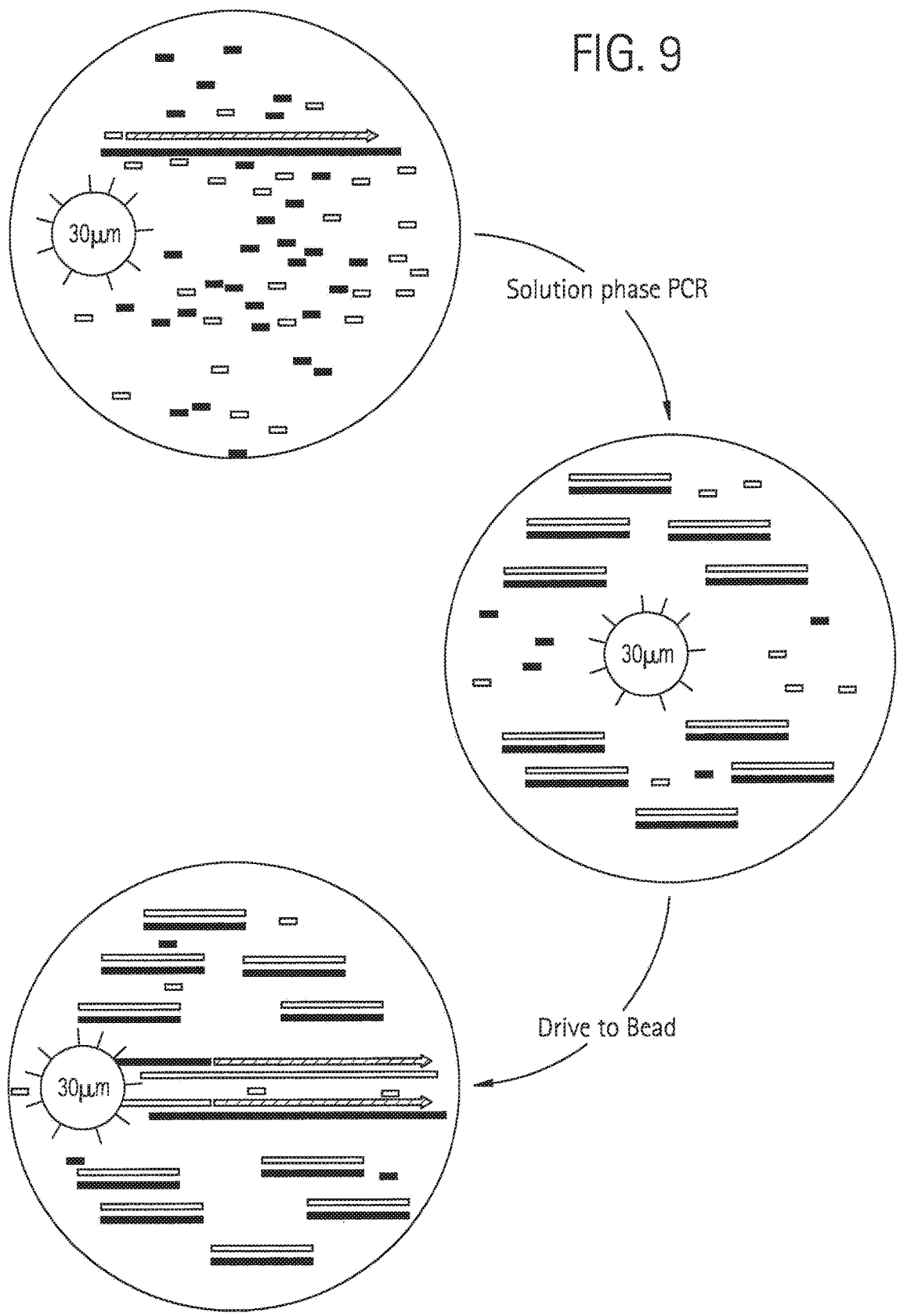
FIG. 9 Schematic showing the amplification and capture stages of bead emulsion amplification used in conjunction with double ended sequencing. The template is amplified by solution phase PCR and the amplification products are attached to the DNA capture bead.
Figure 10A:
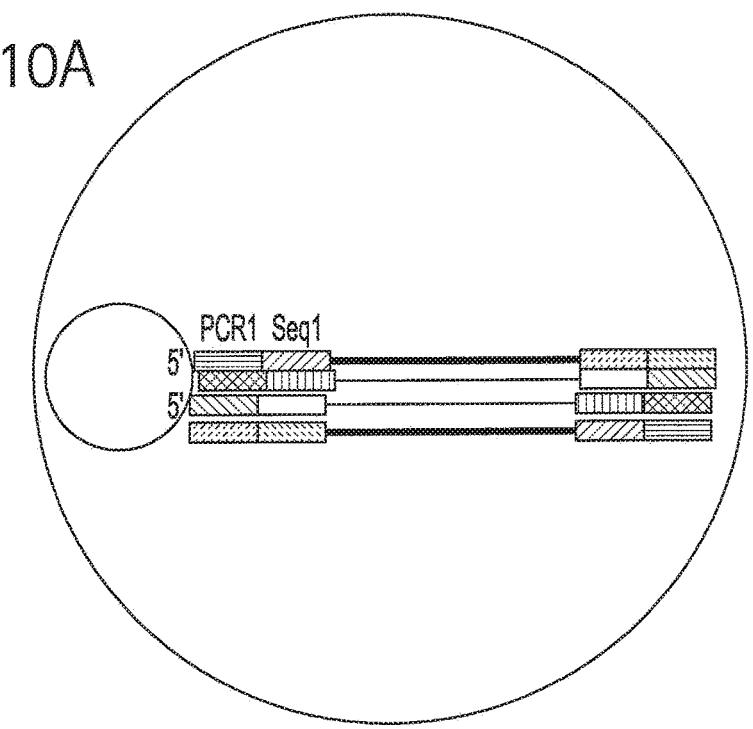
FIGS. 10A-E Schematics showing the later stages of bead emulsion amplification used in conjunction with double ended sequencing. The emulsion is broken down (FIGS. 10A-10B), the second strand of the amplification product is removed and enrichment is used to maximize the number of beads bound with amplification product (FIG. 10C), the sequencing primers are annealed (FIG. 10D), and the first strand is sequenced (FIG. 10E), followed by the second strand.
Figure 10B:
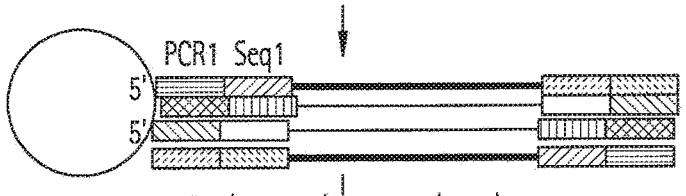
Figure 10C:
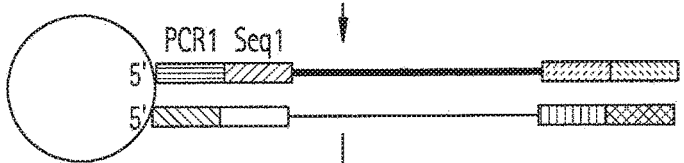
Figure 10D:
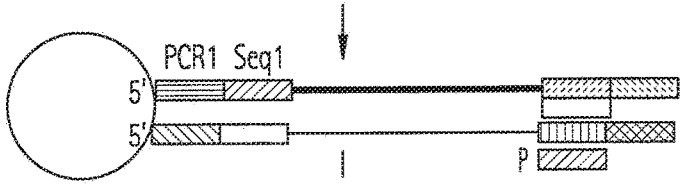
Figure 10E:
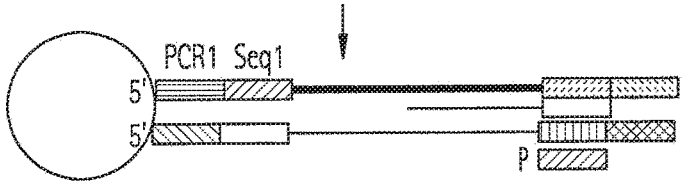

Twenty microliters of the emulsion was taken from the middle of the tube using a P100 pipettor and placed on a microscope slide. The larger pipette tips were used to minimize shear forces. The emulsion was inspected at 50× magnification to ensure that it was comprised predominantly of single beads in 30 to 150 micron diameter microreactors of PCR solution in oil (FIG. 7). After visual examination, the emulsions were immediately amplified.

Example 13: Amplification

The emulsion was aliquotted into 7-8 separate PCR tubes. Each tube included approximately 75 µl of the emulsion. The tubes were sealed and placed in a MJ thermocycler along with the 25 µl negative control described above. The following cycle times were used: 1 cycle of incubation for 4 minutes at 94° C. (Hotstart Initiation), 30 cycles of incubation for 30 seconds at 94° C., and 150 seconds at 68° C. (Amplification), and 40 cycles of incubation for 30 seconds at 94° C., and 360 seconds at 68° C. (Hybridization and Extension). After completion of the PCR program, the tubes were removed and the emulsions were broken immediately or the reactions were stored at 10° C. for up to 16 hours prior to initiating the breaking process.

Example 14: Breaking the Emulsion and Bead Recovery

Following amplification, the emulsifications were examined for breakage (separation of the oil and water phases). Unbroken emulsions were combined into a single 1.5 ml microcentrifuge tube, while the occasional broken emulsion was discarded. As the emulsion samples were quite viscous, significant amounts remained in each PCR tube. The emulsion remaining in the tubes was recovered by adding 75 µl of mineral oil into each PCR tube and pipetting the mixture. This mixture was added to the 1.5 ml tube containing the bulk of the emulsified material. The 1.5 ml tube was then vortexed for 30 seconds. After this, the tube was centrifuged for 20 minutes in the benchtop microcentrifuge at 13.2K rpm (full speed).

After centrifugation, the emulsion separated into two phases with a large white interface. The clear, upper oil phase was discarded, while the cloudy interface material was left in the tube. In a chemical fume hood, 1 ml hexanes was added to the lower phase and interface layer. The mixture was vortexed for 1 minute and centrifuged at full speed for 1 minute in a benchtop microcentrifuge. The top, oil/hexane phase was removed and discarded. After this, 1 ml of 80% Ethanol/1× Annealing Buffer was added to the remaining aqueous phase, interface, and beads. This mixture was vortexed for 1 minute or until the white material from the interface was dissolved. The sample was then centrifuged in a benchtop microcentrifuge for 1 minute at full speed. The tube was rotated 180 degrees, and spun again for an additional minute. The supernatant was then carefully removed without disturbing the bead pellet.

The white bead pellet was washed twice with 1 ml Annealing Buffer containing 0.1% Tween 20. The wash solution was discarded and the beads were pelleted after each wash as described above. The pellet was washed with 1 ml Picopure water. The beads were pelleted with the centrifuge-rotate-centrifuge method used previously. The aqueous phase was carefully removed. The beads were then washed with 1 ml of 1 mM EDTA as before, except that the beads were briefly vortexed at a medium setting for 2 seconds prior to pelleting and supernatant removal.

Amplified DNA, immobilized on the capture beads, was treated to obtain single stranded DNA. The second strand was removed by incubation in a basic melt solution. One ml of Melt Solution (0.125 M NaOH, 0.2 M NaCl) was subsequently added to the beads. The pellet was resuspended by vortexing at a medium setting for 2 seconds, and the tube placed in a Thermolyne LabQuake tube roller for 3 minutes. The beads were then pelleted as above, and the supernatant was carefully removed and discarded. The residual Melt solution was neutralized by the addition of 1 ml Annealing Buffer. After this, the beads were vortexed at medium speed for 2 seconds. The beads were pelleted, and the supernatant was removed as before. The Annealing Buffer wash was repeated, except that only 800 µl of the Annealing Buffer was removed after centrifugation. The beads and remaining Annealing Buffer were transferred to a 0.2 ml PCR tube. The beads were used immediately or stored at 4° C. for up to 48 hours before continuing on to the enrichment process.

Example 15: Bead Enrichment

The bead mass included beads with amplified, immobilized DNA strands, and empty or null beads. As mentioned previously, it was calculated that 61% of the beads lacked template DNA during the amplification process. Enrichment was used to selectively isolate beads with template DNA, thereby maximizing sequencing efficiency. The enrichment process is described in detail below.

The single stranded beads from Example 14 were pelleted with the centrifuge-rotate-centrifuge method, and as much supernatant as possible was removed without disturbing the beads. Fifteen microliters of Annealing Buffer were added to the beads, followed by 2 µl of 100 µM biotinylated, 40 base enrichment primer (5'-Biotin-tetra-ethyleneglycol spacers ccattccccagctcgtcttgccatctgttccctccctgtctcag-3'; SEQ ID NO:5). The primer was complimentary to the combined amplification and sequencing sites (each 20 bases in length) on the 3' end of the bead-immobilized template. The solution was mixed by vortexing at a medium setting for 2 seconds, and the enrichment primers were annealed to the immobilized DNA strands using a controlled denaturation/annealing program in an MJ thermocycler. The program consisted of the following cycle times and temperatures: incubation for 30 seconds at 65° C., decrease by 0.1° C./sec to 58° C., incubation for 90 seconds at 58° C., and hold at 10° C.

While the primers were annealing, Dynal MyOne™ streptavidin beads were resuspend by gentle swirling. Next, 20 µl of the MyOne™ beads were added to a 1.5 ml microcentrifuge tube containing 1 ml of Enhancing fluid (2 M NaCl, 10 mM Tris-HCl, 1 mM EDTA, pH 7.5). The MyOne bead mixture was vortexed for 5 seconds, and the tube was placed in a Dynal MPC-S magnet. The paramagnetic beads were pelleted against the side of the microcentrifuge tube. The supernatant was carefully removed and discarded without disturbing the MyOne™ beads. The tube was removed from the magnet, and 100 µl of enhancing fluid was added. The tube was vortexed for 3 seconds to resuspend the beads, and stored on ice until needed.

Upon completion of the annealing program, 100 µl of annealing buffer was added to the PCR tube containing the DNA capture beads and enrichment primer. The tube vortexed for 5 seconds, and the contents were transferred to a fresh 1.5 ml microcentrifuge tube. The PCR tube in which the enrichment primer was annealed to the capture beads was washed once with 200 µl of annealing buffer, and the wash solution was added to the 1.5 ml tube. The beads were washed three times with 1 ml of annealing buffer, vortexed for 2 seconds, and pelleted as before. The supernatant was carefully removed. After the third wash, the beads were washed twice with 1 ml of ice cold Enhancing fluid. The beads were vortexed, pelleted, and the supernatant was removed as before. The beads were resuspended in 150 µl ice cold Enhancing fluid and the bead solution was added to the washed MyOne™ beads.

The bead mixture was vortexed for 3 seconds and incubated at room temperature for 3 minutes on a LabQuake tube roller. The streptavidin-coated MyOne™ beads were bound to the biotinylated enrichment primers annealed to immobilized templates on the DNA capture beads. The beads were then centrifuged at 2,000 RPM for 3 minutes, after which the beads were vortexed with 2 second pulses until resuspended. The resuspended beads were placed on ice for 5 minutes. Following this, 500 µl of cold Enhancing fluid was added to the beads and the tube was inserted into a Dynal MPC-S magnet. The beads were left undisturbed for 60 seconds to allow pelleting against the magnet. After this, the supernatant with excess MyOne™ and null DNA capture beads was carefully removed and discarded.

The tube was removed from the MPC-S magnet, and 1 ml of cold enhancing fluid added to the beads. The beads were resuspended with gentle finger flicking. It was important not to vortex the beads at this time, as forceful mixing could break the link between the MyOne™ and DNA capture beads. The beads were returned to the magnet, and the supernatant removed. This wash was repeated three additional times to ensure removal of all null capture beads. To remove the annealed enrichment primers and MyOne™ beads, the DNA capture beads were resuspended in 400 µl of melting solution, vortexed for 5 seconds, and pelleted with the magnet. The supernatant with the enriched beads was transferred to a separate 1.5 ml microcentrifuge tube. For maximum recovery of the enriched beads, a second 400 µl aliquot of melting solution was added to the tube containing the MyOne™ beads. The beads were vortexed and pelleted as before. The supernatant from the second wash was removed and combined with the first bolus of enriched beads. The tube of spent MyOne™ beads was discarded.

The microcentrifuge tube of enriched DNA capture beads was placed on the Dynal MPC-S magnet to pellet any residual MyOne™ beads. The enriched beads in the supernatant were transferred to a second 1.5 ml microcentrifuge tube and centrifuged. The supernatant was removed, and the beads were washed 3 times with 1 ml of annealing buffer to neutralize the residual melting solution. After the third wash, 800 µl of the supernatant was removed, and the remaining beads and solution were transferred to a 0.2 ml PCR tube. The enriched beads were centrifuged at 2,000 RPM for 3 minutes and the supernatant decanted. Next, 20 µl of annealing buffer and 3 µl of two different 100 µM sequencing primers (5'-ccatctgttccctccctgtc-3'; SEQ ID NO:6; and 5'-cctatccctgttgcgtgtc-3' phosphate; SEQ ID NO:7) were added. The tube was vortexed for 5 seconds, and placed in an MJ thermocycler for the following 4-stage annealing program: incubation for 5 minutes at 65° C., decrease by 0.1° C./sec to 50° C., incubation for 1 minute at 50° C., decrease by 0.1° C./sec to 40° C., hold at 40° C. for 1 minute, decrease by 0.1° C./sec to 15° C., and hold at 15° C.

Upon completion of the annealing program, the beads were removed from thermocycler and pelleted by centrifugation for 10 seconds. The tube was rotated 180°, and spun for an additional 10 seconds. The supernatant was decanted and discarded, and 200 µl of annealing buffer was added to the tube. The beads were resuspended with a 5 second vortex, and pelleted as before. The supernatant was removed, and the beads resuspended in 100 µl annealing buffer. At this point, the beads were quantitated with a Multisizer 3 Coulter Counter (Beckman Coulter). Beads were stored at 4° C. and were stable for at least 1 week.

Throughout this specification, various patents, published patent applications and scientific references are cited to describe the state and content of the art. Those disclosures, in their entireties, are hereby incorporated into the present specification by reference.

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims.

What is claimed is:

1. A composition comprising a population of nucleic acid template-carrying beads, wherein each bead comprises one or more species of template nucleic acid molecules attached thereto,
   wherein each bead comprises more than 10,000 amplified copies of each of the one or more species of template nucleic acid molecules attached thereto,
   wherein the population of beads are suspended in a microreactor comprising a water-in-oil emulsion, and wherein a plurality of the microreactors includes only one bead.

2. The composition of claim 1, wherein the attachment of each of the amplified copies of the species of template nucleic acid molecules to the bead is mediated by chemical groups or oligonucleotides that are bound to the surface of the bead.

3. The composition of claim 2, wherein the attachment of each of the amplified copies of the species of template nucleic acid molecules is a covalent chemical attachment.

4. The composition of claim 2, wherein the attachment of each of the amplified copies of the species of template nucleic acid molecules is a non-covalent attachment.

5. The composition of claim 1, wherein each bead comprises a single species of template nucleic acid molecules.

6. The composition of claim 1, wherein the beads are made from a material selected from the group consisting of cellulose, cellulose derivatives, acrylic resins, glass, silica gels, polystyrene, gelatin, polyvinyl pyrrolidone, co-polymers of vinyl and acrylamide, polystyrene cross-linked with divinylbenzene, polyacrylamide latex gels, polystyrene, dextran, rubber, silicon, plastics, nitrocellulose, natural sponges, control pore glass, metals, cross-linked dextrans, and agarose gel.

7. The composition of claim 6, wherein each bead is approximately 2 to 100 µm in diameter.

8. The composition of claim 7, wherein each bead is approximately 10 to 80 µm in diameter.

9. The composition of claim 8, wherein each bead is approximately 20 to 40 µm in diameter.

* * * * *

SEQUENCE LISTING

```
<160> NUMBER OF SEQ ID NOS: 7

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 1
gcttacctga ccgacctctg cctatccct gttgcgtgtc                              40

<210> SEQ ID NO 2
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 2
ccattcccca gctcgtcttg ccatctgttc cctccctgtc                             40

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gcttacctga ccgacctctg                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 4
ccattcccca gctcgtcttg                                                20

<210> SEQ ID NO 5
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 5
ccattcccca gctcgtcttg ccatctgttc cctccctgtc tcag                    44

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ccatctgttc cctccctgtc                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
cctatcccct gttgcgtgtc                                                20
```